United States Patent
Good et al.

(10) Patent No.: US 11,732,033 B2
(45) Date of Patent: Aug. 22, 2023

(54) **IMMUNOGENIC PEPTIDE AGAINST GROUP A *STREPTOCOCCUS***

(71) Applicant: GRIFFITH UNIVERSITY, Nathan (AU)

(72) Inventors: Michael F. Good, The Gap (AU); Manisha Pandey, Calamvale (AU); Michael Raymond Batzloff, Holmview (AU)

(73) Assignee: GRIFFITH UNIVERSITY, Nathan (AU)

( * ) Notice: Subject to any disclaimer, the term of this patent is extended or adjusted under 35 U.S.C. 154(b) by 285 days.

(21) Appl. No.: 16/640,819

(22) PCT Filed: Aug. 22, 2018

(86) PCT No.: PCT/AU2018/050893
§ 371 (c)(1),
(2) Date: Feb. 21, 2020

(87) PCT Pub. No.: WO2019/036761
PCT Pub. Date: Feb. 28, 2019

(65) Prior Publication Data
US 2021/0024619 A1    Jan. 28, 2021

(30) Foreign Application Priority Data
Aug. 23, 2017 (NL) .................... 2019439

(51) Int. Cl.
| *A61K 39/09* | (2006.01) |
| *A61K 38/16* | (2006.01) |
| *A61K 39/116* | (2006.01) |
| *A61K 9/00* | (2006.01) |
| *A61K 47/64* | (2017.01) |
| *C07K 14/315* | (2006.01) |
| *C07K 16/12* | (2006.01) |
| *A61K 39/385* | (2006.01) |
| *A61K 39/00* | (2006.01) |

(52) U.S. Cl.
CPC ........ *C07K 16/1271* (2013.01); *A61K 9/0019* (2013.01); *A61K 38/16* (2013.01); *A61K 39/092* (2013.01); *A61K 39/116* (2013.01); *A61K 47/646* (2017.08); *C07K 14/315* (2013.01)

(58) Field of Classification Search
None
See application file for complete search history.

(56) References Cited

U.S. PATENT DOCUMENTS
2009/0162369 A1    6/2009    Nordstrom et al.

FOREIGN PATENT DOCUMENTS
| WO | WO 2015/157820 | 10/2015 |
| WO | WO 2017/070735 | 5/2017 |

OTHER PUBLICATIONS

English translation of Artemuk et al., "Amino acids and proteins," Brest State University Named After A.S. Pushkin, 34, pp. 2010.
English translation of Office Communication issued in Russian Patent Application No. 2020111297, dated Dec. 23, 2021.
PCT International Preliminary Report on Patentability issued in International Application No. PCT/AU2018/050893, dated Dec. 16, 2019.
PCT International Search Report and Written Opinion issued in International Application No. PCT/AU2018/050893, dated Oct. 5, 2018.
Voss et al., "A CD14 Domain with Lipopolysaccharide-Binding and -Neutralizing Activity," ChemBioChem 7:275-786, 2006.
Zaman et al., "Novel platform technology for modular mucosal vaccine that protects against *Streptococcus*," Sci. Rep. 6:39274, 2016.

*Primary Examiner* — S. Devi
(74) *Attorney, Agent, or Firm* — Parker Highlander PLLC

(57) ABSTRACT

A modified p145 peptide having enhanced mucosal immunogenicity for use in eliciting a mucosal immune response to group A Streptococcal bacteria in a mammal such as a human. Intramuscular administration of the modified p145 5 peptide may be particularly efficacious. An S2 peptide or variant may be co-administered with the modified p145 peptide to enhance the immune response.

17 Claims, 21 Drawing Sheets
Specification includes a Sequence Listing.

| Peptide # | N-terminal | 1 (a) | 2 (b) | 3 (c) | 4 (d) | 5 (e) | 6 (f) | 7 (g) | 8 (a) | 9 (b) | 10 (c) | 11 (d) | 12 (e) | C-terminal |
|---|---|---|---|---|---|---|---|---|---|---|---|---|---|---|
| 1 (p145) | LRRDLDA | S | R | E | A | K | K | Q | V | E | K | A | L | E |
| 5 | LRRDLDA | E | R | E | A | K | K | Q | V | E | K | A | L | E |
| 6 | LRRDLDA | V | R | E | A | K | K | Q | V | E | K | A | L | E |
| 11 | LRRDLDA | S | N | E | A | K | K | Q | V | E | K | A | L | E |
| 13 | LRRDLDA | S | D | E | A | K | K | Q | V | E | K | A | L | E |
| 40 | LRRDLDA | S | R | E | A | K | N | Q | V | E | K | A | L | E |
| 66 | LRRDLDA | S | R | E | A | K | K | Q | V | E | R | A | L | E |
| 72 | LRRDLDA | S | R | E | A | K | K | Q | V | E | M | A | L | E |

Figure 1C

**Intramuscular immunisation (x3) with p*17-DT+K4S2-DT/Alum and Intranasal challenge with 5448AP (CovR/S MT strain)**

Immunisation groups
A. p*17-DT/Alum – total 25 µg
B. p*17-DT+K4S2-DT/Alum – 12.5 µg p*17-DT and 12.5 µg K4S2-DT
C. PBS/Alum Immunisation schedule – Intramuscular Day 0 → Day 21 → Day 42 → Day 50 → Day 60

| i.m. | i.m. | i.m. | Serum Saliva | Intranasal Challenge 5448AP |

Figure 9

SEQUENCE LISTING

<160> NUMBER OF SEQ ID NOS: 114

<210> SEQ ID NO 1
<211> LENGTH: 20
<212> TYPE: PRT
<213> ORGANISM: Artificial sequence
<220> FEATURE:
<223> OTHER INFORMATION: Synthetic polypeptide

<400> SEQUENCE: 1

Leu Arg Arg Asp Leu Asp Ala Ser Arg Glu Ala Lys Asn Gln Val Glu
1               5                   10                  15

Arg Ala Leu Glu
            20

<210> SEQ ID NO 2
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 2

Ser Arg Glu Ala Lys Asn Gln Val Glu Arg Ala Leu
1               5                   10

<210> SEQ ID NO 3
<211> LENGTH: 20
<212> TYPE: PRT
<213> ORGANISM: Artificial sequence
<220> FEATURE:
<223> OTHER INFORMATION: Synthetic polypeptide

<400> SEQUENCE: 3

Leu Arg Arg Asp Leu Asp Ala Ser Arg Glu Ala Lys Lys Gln Val Glu
1               5                   10                  15

Lys Ala Leu Glu
            20

<210> SEQ ID NO 4
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 4

Ser Arg Glu Ala Lys Lys Gln Val Glu Lys Ala Leu
1               5                   10

<210> SEQ ID NO 5
<211> LENGTH: 20
<212> TYPE: PRT
<213> ORGANISM: Artificial sequence
<220> FEATURE:
<223> OTHER INFORMATION: Synthetic polypeptide

<400> SEQUENCE: 5

Leu Arg Arg Asp Leu Asp Ala Glu Asn Glu Ala Lys Lys Gln Val Glu
1               5                   10                  15

Lys Ala Leu Glu
            20

<210> SEQ ID NO 6
<211> LENGTH: 20
<212> TYPE: PRT
<213> ORGANISM: Artificial sequence
<220> FEATURE:
<223> OTHER INFORMATION: Synthetic polypeptide

<400> SEQUENCE: 6

Leu Arg Arg Asp Leu Asp Ala Glu Asp Glu Ala Lys Lys Gln Val Glu
1               5                   10                  15

Lys Ala Leu Glu
            20

<210> SEQ ID NO 7
<211> LENGTH: 20
<212> TYPE: PRT
<213> ORGANISM: Artificial sequence
<220> FEATURE:
<223> OTHER INFORMATION: Synthetic polypeptide

<400> SEQUENCE: 7

Leu Arg Arg Asp Leu Asp Ala Glu Arg Glu Ala Lys Asn Gln Val Glu
1               5                   10                  15

Lys Ala Leu Glu
            20

<210> SEQ ID NO 8
<211> LENGTH: 20
<212> TYPE: PRT
<213> ORGANISM: Artificial sequence
<220> FEATURE:
<223> OTHER INFORMATION: Synthetic polypeptide

<400> SEQUENCE: 8

Leu Arg Arg Asp Leu Asp Ala Glu Arg Glu Ala Lys Lys Gln Val Glu
1               5                   10                  15

Arg Ala Leu Glu
            20

<210> SEQ ID NO 9
<211> LENGTH: 20
<212> TYPE: PRT
<213> ORGANISM: Artificial sequence
<220> FEATURE:
<223> OTHER INFORMATION: Synthetic polypeptide

<400> SEQUENCE: 9

Leu Arg Arg Asp Leu Asp Ala Glu Arg Glu Ala Lys Lys Gln Val Glu

```
1               5                   10                  15
Met Ala Leu Glu
        20

<210> SEQ ID NO 10
<211> LENGTH: 20
<212> TYPE: PRT
<213> ORGANISM: Artificial sequence
<220> FEATURE:
<223> OTHER INFORMATION: Synthetic polypeptide

<400> SEQUENCE: 10

Leu Arg Arg Asp Leu Asp Ala Val Asn Glu Ala Lys Lys Gln Val Glu
1               5                   10                  15

Lys Ala Leu Glu
        20

<210> SEQ ID NO 11
<211> LENGTH: 20
<212> TYPE: PRT
<213> ORGANISM: Artificial sequence
<220> FEATURE:
<223> OTHER INFORMATION: Synthetic polypeptide

<400> SEQUENCE: 11

Leu Arg Arg Asp Leu Asp Ala Val Asp Glu Ala Lys Lys Gln Val Glu
1               5                   10                  15

Lys Ala Leu Glu
        20

<210> SEQ ID NO 12
<211> LENGTH: 20
<212> TYPE: PRT
<213> ORGANISM: Artificial sequence
<220> FEATURE:
<223> OTHER INFORMATION: Synthetic polypeptide

<400> SEQUENCE: 12

Leu Arg Arg Asp Leu Asp Ala Val Arg Glu Ala Lys Asn Gln Val Glu
1               5                   10                  15

Lys Ala Leu Glu
        20

<210> SEQ ID NO 13
<211> LENGTH: 20
<212> TYPE: PRT
<213> ORGANISM: Artificial sequence
<220> FEATURE:
<223> OTHER INFORMATION: Synthetic polypeptide

<400> SEQUENCE: 13

Leu Arg Arg Asp Leu Asp Ala Val Arg Glu Ala Lys Lys Gln Val Glu
1               5                   10                  15

Arg Ala Leu Glu
        20

<210> SEQ ID NO 14
<211> LENGTH: 20
<212> TYPE: PRT
<213> ORGANISM: Artificial sequence
<220> FEATURE:
<223> OTHER INFORMATION: Synthetic polypeptide

<400> SEQUENCE: 14
```

```
Leu Arg Arg Asp Leu Asp Ala Val Arg Glu Ala Lys Lys Gln Val Glu
1               5                   10                  15

Met Ala Leu Glu
            20

<210> SEQ ID NO 15
<211> LENGTH: 20
<212> TYPE: PRT
<213> ORGANISM: Artificial sequence
<220> FEATURE:
<223> OTHER INFORMATION: Synthetic polypeptide

<400> SEQUENCE: 15

Leu Arg Arg Asp Leu Asp Ala Ser Asn Glu Ala Lys Asn Gln Val Glu
1               5                   10                  15

Lys Ala Leu Glu
            20

<210> SEQ ID NO 16
<211> LENGTH: 20
<212> TYPE: PRT
<213> ORGANISM: Artificial sequence
<220> FEATURE:
<223> OTHER INFORMATION: Synthetic polypeptide

<400> SEQUENCE: 16

Leu Arg Arg Asp Leu Asp Ala Ser Asn Glu Ala Lys Lys Gln Val Glu
1               5                   10                  15

Arg Ala Leu Glu
            20

<210> SEQ ID NO 17
<211> LENGTH: 20
<212> TYPE: PRT
<213> ORGANISM: Artificial sequence
<220> FEATURE:
<223> OTHER INFORMATION: Synthetic polypeptide

<400> SEQUENCE: 17

Leu Arg Arg Asp Leu Asp Ala Ser Asn Glu Ala Lys Lys Gln Val Glu
1               5                   10                  15

Met Ala Leu Glu
            20

<210> SEQ ID NO 18
<211> LENGTH: 20
<212> TYPE: PRT
<213> ORGANISM: Artificial sequence
<220> FEATURE:
<223> OTHER INFORMATION: Synthetic polypeptide

<400> SEQUENCE: 18

Leu Arg Arg Asp Leu Asp Ala Ser Asp Glu Ala Lys Asn Gln Val Glu
1               5                   10                  15

Lys Ala Leu Glu
            20

<210> SEQ ID NO 19
<211> LENGTH: 20
<212> TYPE: PRT
<213> ORGANISM: Artificial sequence
<220> FEATURE:
<223> OTHER INFORMATION: Synthetic polypeptide

<400> SEQUENCE: 19
```

```
Leu Arg Arg Asp Leu Asp Ala Ser Asp Glu Ala Lys Lys Gln Val Glu
1               5                   10                  15

Arg Ala Leu Glu
            20

<210> SEQ ID NO 20
<211> LENGTH: 20
<212> TYPE: PRT
<213> ORGANISM: Artificial sequence
<220> FEATURE:
<223> OTHER INFORMATION: Synthetic polypeptide

<400> SEQUENCE: 20

Leu Arg Arg Asp Leu Asp Ala Ser Asp Glu Ala Lys Lys Gln Val Glu
1               5                   10                  15

Met Ala Leu Glu
            20

<210> SEQ ID NO 21
<211> LENGTH: 20
<212> TYPE: PRT
<213> ORGANISM: Artificial sequence
<220> FEATURE:
<223> OTHER INFORMATION: Synthetic polypeptide

<400> SEQUENCE: 21

Leu Arg Arg Asp Leu Asp Ala Ser Arg Glu Ala Lys Asn Gln Val Glu
1               5                   10                  15

Met Ala Leu Glu
            20

<210> SEQ ID NO 22
<211> LENGTH: 7
<212> TYPE: PRT
<213> ORGANISM: Artificial sequence
<220> FEATURE:
<223> OTHER INFORMATION: Synthetic polypeptide

<400> SEQUENCE: 22

Leu Arg Arg Asp Leu Asp Ala
1               5

<210> SEQ ID NO 23
<211> LENGTH: 20
<212> TYPE: PRT
<213> ORGANISM: Artificial sequence
<220> FEATURE:
<223> OTHER INFORMATION: Synthetic polypeptide

<400> SEQUENCE: 23

Asn Ser Asp Asn Ile Lys Glu Asn Gln Phe Glu Asp Phe Asp Glu Asp
1               5                   10                  15

Trp Glu Asn Phe
            20

<210> SEQ ID NO 24
<211> LENGTH: 24
<212> TYPE: PRT
<213> ORGANISM: Artificial sequence
<220> FEATURE:
<223> OTHER INFORMATION: Synthetic polypeptide

<400> SEQUENCE: 24

Lys Lys Lys Lys Asn Ser Asp Asn Ile Lys Glu Asn Gln Phe Glu Asp
```

```
Phe Asp Glu Asp Trp Glu Asn Phe
            20

<210> SEQ ID NO 25
<211> LENGTH: 24
<212> TYPE: PRT
<213> ORGANISM: Artificial sequence
<220> FEATURE:
<223> OTHER INFORMATION: Synthetic polypeptide

<400> SEQUENCE: 25

Ser Gly Ser Gly Leu Arg Arg Asp Leu Asp Ala Leu Arg Glu Ala Lys
1               5                   10                  15

Lys Gln Val Glu Lys Ala Leu Glu
            20

<210> SEQ ID NO 26
<211> LENGTH: 24
<212> TYPE: PRT
<213> ORGANISM: Artificial sequence
<220> FEATURE:
<223> OTHER INFORMATION: Synthetic polypeptide

<400> SEQUENCE: 26

Ser Gly Ser Gly Leu Arg Arg Asp Leu Asp Ala Ala Arg Glu Ala Lys
1               5                   10                  15

Lys Gln Val Glu Lys Ala Leu Glu
            20

<210> SEQ ID NO 27
<211> LENGTH: 24
<212> TYPE: PRT
<213> ORGANISM: Artificial sequence
<220> FEATURE:
<223> OTHER INFORMATION: Synthetic polypeptide

<400> SEQUENCE: 27

Ser Gly Ser Gly Leu Arg Arg Asp Leu Asp Ala Tyr Arg Glu Ala Lys
1               5                   10                  15

Lys Gln Val Glu Lys Ala Leu Glu
            20

<210> SEQ ID NO 28
<211> LENGTH: 24
<212> TYPE: PRT
<213> ORGANISM: Artificial sequence
<220> FEATURE:
<223> OTHER INFORMATION: Synthetic polypeptide

<400> SEQUENCE: 28

Ser Gly Ser Gly Leu Arg Arg Asp Leu Asp Ala Met Arg Glu Ala Lys
1               5                   10                  15

Lys Gln Val Glu Lys Ala Leu Glu
            20

<210> SEQ ID NO 29
<211> LENGTH: 24
<212> TYPE: PRT
<213> ORGANISM: Artificial sequence
<220> FEATURE:
<223> OTHER INFORMATION: Synthetic polypeptide

<400> SEQUENCE: 29
```

Ser Gly Ser Gly Leu Arg Arg Asp Leu Asp Ala Glu Arg Glu Ala Lys
1               5                   10                  15

Lys Gln Val Glu Lys Ala Leu Glu
            20

<210> SEQ ID NO 30
<211> LENGTH: 24
<212> TYPE: PRT
<213> ORGANISM: Artificial sequence
<220> FEATURE:
<223> OTHER INFORMATION: Synthetic polypeptide

<400> SEQUENCE: 30

Ser Gly Ser Gly Leu Arg Arg Asp Leu Asp Ala Val Arg Glu Ala Lys
1               5                   10                  15

Lys Gln Val Glu Lys Ala Leu Glu
            20

<210> SEQ ID NO 31
<211> LENGTH: 24
<212> TYPE: PRT
<213> ORGANISM: Artificial sequence
<220> FEATURE:
<223> OTHER INFORMATION: Synthetic polypeptide

<400> SEQUENCE: 31

Ser Gly Ser Gly Leu Arg Arg Asp Leu Asp Ala Ile Arg Glu Ala Lys
1               5                   10                  15

Lys Gln Val Glu Lys Ala Leu Glu
            20

<210> SEQ ID NO 32
<211> LENGTH: 24
<212> TYPE: PRT
<213> ORGANISM: Artificial sequence
<220> FEATURE:
<223> OTHER INFORMATION: Synthetic polypeptide

<400> SEQUENCE: 32

Ser Gly Ser Gly Leu Arg Arg Asp Leu Asp Ala Ser Glu Glu Ala Lys
1               5                   10                  15

Lys Gln Val Glu Lys Ala Leu Glu
            20

<210> SEQ ID NO 33
<211> LENGTH: 24
<212> TYPE: PRT
<213> ORGANISM: Artificial sequence
<220> FEATURE:
<223> OTHER INFORMATION: Synthetic polypeptide

<400> SEQUENCE: 33

Ser Gly Ser Gly Leu Arg Arg Asp Leu Asp Ala Ser Gln Glu Ala Lys
1               5                   10                  15

Lys Gln Val Glu Lys Ala Leu Glu
            20

<210> SEQ ID NO 34
<211> LENGTH: 24
<212> TYPE: PRT
<213> ORGANISM: Artificial sequence
<220> FEATURE:
<223> OTHER INFORMATION: Synthetic polypeptide

<400> SEQUENCE: 34

```
Ser Gly Ser Gly Leu Arg Arg Asp Leu Asp Ala Ser Lys Glu Ala Lys
1               5                   10                  15

Lys Gln Val Glu Lys Ala Leu Glu
            20
```

<210> SEQ ID NO 35
<211> LENGTH: 24
<212> TYPE: PRT
<213> ORGANISM: Artificial sequence
<220> FEATURE:
<223> OTHER INFORMATION: Synthetic polypeptide

<400> SEQUENCE: 35

```
Ser Gly Ser Gly Leu Arg Arg Asp Leu Asp Ala Ser Asn Glu Ala Lys
1               5                   10                  15

Lys Gln Val Glu Lys Ala Leu Glu
            20
```

<210> SEQ ID NO 36
<211> LENGTH: 24
<212> TYPE: PRT
<213> ORGANISM: Artificial sequence
<220> FEATURE:
<223> OTHER INFORMATION: Synthetic polypeptide

<400> SEQUENCE: 36

```
Ser Gly Ser Gly Leu Arg Arg Asp Leu Asp Ala Ser Thr Glu Ala Lys
1               5                   10                  15

Lys Gln Val Glu Lys Ala Leu Glu
            20
```

<210> SEQ ID NO 37
<211> LENGTH: 24
<212> TYPE: PRT
<213> ORGANISM: Artificial sequence
<220> FEATURE:
<223> OTHER INFORMATION: Synthetic polypeptide

<400> SEQUENCE: 37

```
Ser Gly Ser Gly Leu Arg Arg Asp Leu Asp Ala Ser Asp Glu Ala Lys
1               5                   10                  15

Lys Gln Val Glu Lys Ala Leu Glu
            20
```

<210> SEQ ID NO 38
<211> LENGTH: 24
<212> TYPE: PRT
<213> ORGANISM: Artificial sequence
<220> FEATURE:
<223> OTHER INFORMATION: Synthetic polypeptide

<400> SEQUENCE: 38

```
Ser Gly Ser Gly Leu Arg Arg Asp Leu Asp Ala Ser Arg Asn Ala Lys
1               5                   10                  15

Lys Gln Val Glu Lys Ala Leu Glu
            20
```

<210> SEQ ID NO 39
<211> LENGTH: 24
<212> TYPE: PRT
<213> ORGANISM: Artificial sequence
<220> FEATURE:
<223> OTHER INFORMATION: Synthetic polypeptide

```
<400> SEQUENCE: 39

Ser Gly Ser Gly Leu Arg Arg Asp Leu Asp Ala Ser Arg Lys Ala Lys
1               5                   10                  15

Lys Gln Val Glu Lys Ala Leu Glu
            20

<210> SEQ ID NO 40
<211> LENGTH: 24
<212> TYPE: PRT
<213> ORGANISM: Artificial sequence
<220> FEATURE:
<223> OTHER INFORMATION: Synthetic polypeptide

<400> SEQUENCE: 40

Ser Gly Ser Gly Leu Arg Arg Asp Leu Asp Ala Ser Arg Arg Ala Lys
1               5                   10                  15

Lys Gln Val Glu Lys Ala Leu Glu
            20

<210> SEQ ID NO 41
<211> LENGTH: 24
<212> TYPE: PRT
<213> ORGANISM: Artificial sequence
<220> FEATURE:
<223> OTHER INFORMATION: Synthetic polypeptide

<400> SEQUENCE: 41

Ser Gly Ser Gly Leu Arg Arg Asp Leu Asp Ala Ser Arg Asp Ala Lys
1               5                   10                  15

Lys Gln Val Glu Lys Ala Leu Glu
            20

<210> SEQ ID NO 42
<211> LENGTH: 24
<212> TYPE: PRT
<213> ORGANISM: Artificial sequence
<220> FEATURE:
<223> OTHER INFORMATION: Synthetic polypeptide

<400> SEQUENCE: 42

Ser Gly Ser Gly Leu Arg Arg Asp Leu Asp Ala Ser Arg Gln Ala Lys
1               5                   10                  15

Lys Gln Val Glu Lys Ala Leu Glu
            20

<210> SEQ ID NO 43
<211> LENGTH: 24
<212> TYPE: PRT
<213> ORGANISM: Artificial sequence
<220> FEATURE:
<223> OTHER INFORMATION: Synthetic polypeptide

<400> SEQUENCE: 43

Ser Gly Ser Gly Leu Arg Arg Asp Leu Asp Ala Ser Arg Ala Ala Lys
1               5                   10                  15

Lys Gln Val Glu Lys Ala Leu Glu
            20

<210> SEQ ID NO 44
<211> LENGTH: 24
<212> TYPE: PRT
<213> ORGANISM: Artificial sequence
<220> FEATURE:
<223> OTHER INFORMATION: Synthetic polypeptide
```

<400> SEQUENCE: 44

Ser Gly Ser Gly Leu Arg Arg Asp Leu Asp Ala Ser Arg Ser Ala Lys
1               5                   10                  15

Lys Gln Val Glu Lys Ala Leu Glu
            20

<210> SEQ ID NO 45
<211> LENGTH: 24
<212> TYPE: PRT
<213> ORGANISM: Artificial sequence
<220> FEATURE:
<223> OTHER INFORMATION: Synthetic polypeptide

<400> SEQUENCE: 45

Ser Gly Ser Gly Leu Arg Arg Asp Leu Asp Ala Ser Arg Thr Ala Lys
1               5                   10                  15

Lys Gln Val Glu Lys Ala Leu Glu
            20

<210> SEQ ID NO 46
<211> LENGTH: 24
<212> TYPE: PRT
<213> ORGANISM: Artificial sequence
<220> FEATURE:
<223> OTHER INFORMATION: Synthetic polypeptide

<400> SEQUENCE: 46

Ser Gly Ser Gly Leu Arg Arg Asp Leu Asp Ala Ser Arg Glu Glu Lys
1               5                   10                  15

Lys Gln Val Glu Lys Ala Leu Glu
            20

<210> SEQ ID NO 47
<211> LENGTH: 24
<212> TYPE: PRT
<213> ORGANISM: Artificial sequence
<220> FEATURE:
<223> OTHER INFORMATION: Synthetic polypeptide

<400> SEQUENCE: 47

Ser Gly Ser Gly Leu Arg Arg Asp Leu Asp Ala Ser Arg Glu Lys Lys
1               5                   10                  15

Lys Gln Val Glu Lys Ala Leu Glu
            20

<210> SEQ ID NO 48
<211> LENGTH: 24
<212> TYPE: PRT
<213> ORGANISM: Artificial sequence
<220> FEATURE:
<223> OTHER INFORMATION: Synthetic polypeptide

<400> SEQUENCE: 48

Ser Gly Ser Gly Leu Arg Arg Asp Leu Asp Ala Ser Arg Glu Gln Lys
1               5                   10                  15

Lys Gln Val Glu Lys Ala Leu Glu
            20

<210> SEQ ID NO 49
<211> LENGTH: 24
<212> TYPE: PRT
<213> ORGANISM: Artificial sequence
<220> FEATURE:

<223> OTHER INFORMATION: Synthetic polypeptide

<400> SEQUENCE: 49

Ser Gly Ser Gly Leu Arg Arg Asp Leu Asp Ala Ser Arg Glu Asn Lys
1               5                   10                  15

Lys Gln Val Glu Lys Ala Leu Glu
            20

<210> SEQ ID NO 50
<211> LENGTH: 24
<212> TYPE: PRT
<213> ORGANISM: Artificial sequence
<220> FEATURE:
<223> OTHER INFORMATION: Synthetic polypeptide

<400> SEQUENCE: 50

Ser Gly Ser Gly Leu Arg Arg Asp Leu Asp Ala Ser Arg Glu Arg Lys
1               5                   10                  15

Lys Gln Val Glu Lys Ala Leu Glu
            20

<210> SEQ ID NO 51
<211> LENGTH: 24
<212> TYPE: PRT
<213> ORGANISM: Artificial sequence
<220> FEATURE:
<223> OTHER INFORMATION: Synthetic polypeptide

<400> SEQUENCE: 51

Ser Gly Ser Gly Leu Arg Arg Asp Leu Asp Ala Ser Arg Glu Asp Lys
1               5                   10                  15

Lys Gln Val Glu Lys Ala Leu Glu
            20

<210> SEQ ID NO 52
<211> LENGTH: 24
<212> TYPE: PRT
<213> ORGANISM: Artificial sequence
<220> FEATURE:
<223> OTHER INFORMATION: Synthetic polypeptide

<400> SEQUENCE: 52

Ser Gly Ser Gly Leu Arg Arg Asp Leu Asp Ala Ser Arg Glu Ala Leu
1               5                   10                  15

Lys Gln Val Glu Lys Ala Leu Glu
            20

<210> SEQ ID NO 53
<211> LENGTH: 24
<212> TYPE: PRT
<213> ORGANISM: Artificial sequence
<220> FEATURE:
<223> OTHER INFORMATION: Synthetic polypeptide

<400> SEQUENCE: 53

Ser Gly Ser Gly Leu Arg Arg Asp Leu Asp Ala Ser Arg Glu Ala Ile
1               5                   10                  15

Lys Gln Val Glu Lys Ala Leu Glu
            20

<210> SEQ ID NO 54
<211> LENGTH: 24
<212> TYPE: PRT
<213> ORGANISM: Artificial sequence

```
<220> FEATURE:
<223> OTHER INFORMATION: Synthetic polypeptide

<400> SEQUENCE: 54

Ser Gly Ser Gly Leu Arg Arg Asp Leu Asp Ala Ser Arg Glu Ala Met
1               5                   10                  15

Lys Gln Val Glu Lys Ala Leu Glu
            20

<210> SEQ ID NO 55
<211> LENGTH: 24
<212> TYPE: PRT
<213> ORGANISM: Artificial sequence
<220> FEATURE:
<223> OTHER INFORMATION: Synthetic polypeptide

<400> SEQUENCE: 55

Ser Gly Ser Gly Leu Arg Arg Asp Leu Asp Ala Ser Arg Glu Ala Val
1               5                   10                  15

Lys Gln Val Glu Lys Ala Leu Glu
            20

<210> SEQ ID NO 56
<211> LENGTH: 24
<212> TYPE: PRT
<213> ORGANISM: Artificial sequence
<220> FEATURE:
<223> OTHER INFORMATION: Synthetic polypeptide

<400> SEQUENCE: 56

Ser Gly Ser Gly Leu Arg Arg Asp Leu Asp Ala Ser Arg Glu Ala Tyr
1               5                   10                  15

Lys Gln Val Glu Lys Ala Leu Glu
            20

<210> SEQ ID NO 57
<211> LENGTH: 24
<212> TYPE: PRT
<213> ORGANISM: Artificial sequence
<220> FEATURE:
<223> OTHER INFORMATION: Synthetic polypeptide

<400> SEQUENCE: 57

Ser Gly Ser Gly Leu Arg Arg Asp Leu Asp Ala Ser Arg Glu Ala Ala
1               5                   10                  15

Lys Gln Val Glu Lys Ala Leu Glu
            20

<210> SEQ ID NO 58
<211> LENGTH: 24
<212> TYPE: PRT
<213> ORGANISM: Artificial sequence
<220> FEATURE:
<223> OTHER INFORMATION: Synthetic polypeptide

<400> SEQUENCE: 58

Ser Gly Ser Gly Leu Arg Arg Asp Leu Asp Ala Ser Arg Glu Ala Asn
1               5                   10                  15

Lys Gln Val Glu Lys Ala Leu Glu
            20

<210> SEQ ID NO 59
<211> LENGTH: 24
<212> TYPE: PRT
```

```
<213> ORGANISM: Artificial sequence
<220> FEATURE:
<223> OTHER INFORMATION: Synthetic polypeptide

<400> SEQUENCE: 59

Ser Gly Ser Gly Leu Arg Arg Asp Leu Asp Ala Ser Arg Glu Ala Arg
1               5                   10                  15

Lys Gln Val Glu Lys Ala Leu Glu
            20

<210> SEQ ID NO 60
<211> LENGTH: 24
<212> TYPE: PRT
<213> ORGANISM: Artificial sequence
<220> FEATURE:
<223> OTHER INFORMATION: Synthetic polypeptide

<400> SEQUENCE: 60

Ser Gly Ser Gly Leu Arg Arg Asp Leu Asp Ala Ser Arg Glu Ala Lys
1               5                   10                  15

Glu Gln Val Glu Lys Ala Leu Glu
            20

<210> SEQ ID NO 61
<211> LENGTH: 24
<212> TYPE: PRT
<213> ORGANISM: Artificial sequence
<220> FEATURE:
<223> OTHER INFORMATION: Synthetic polypeptide

<400> SEQUENCE: 61

Ser Gly Ser Gly Leu Arg Arg Asp Leu Asp Ala Ser Arg Glu Ala Lys
1               5                   10                  15

Asp Gln Val Glu Lys Ala Leu Glu
            20

<210> SEQ ID NO 62
<211> LENGTH: 24
<212> TYPE: PRT
<213> ORGANISM: Artificial sequence
<220> FEATURE:
<223> OTHER INFORMATION: Synthetic polypeptide

<400> SEQUENCE: 62

Ser Gly Ser Gly Leu Arg Arg Asp Leu Asp Ala Ser Arg Glu Ala Lys
1               5                   10                  15

Gln Gln Val Glu Lys Ala Leu Glu
            20

<210> SEQ ID NO 63
<211> LENGTH: 24
<212> TYPE: PRT
<213> ORGANISM: Artificial sequence
<220> FEATURE:
<223> OTHER INFORMATION: Synthetic polypeptide

<400> SEQUENCE: 63

Ser Gly Ser Gly Leu Arg Arg Asp Leu Asp Ala Ser Arg Glu Ala Lys
1               5                   10                  15

Ala Gln Val Glu Lys Ala Leu Glu
            20

<210> SEQ ID NO 64
<211> LENGTH: 24
```

```
<212> TYPE: PRT
<213> ORGANISM: Artificial sequence
<220> FEATURE:
<223> OTHER INFORMATION: Synthetic polypeptide

<400> SEQUENCE: 64

Ser Gly Ser Gly Leu Arg Arg Asp Leu Asp Ala Ser Arg Glu Ala Lys
1               5                   10                  15
Asn Gln Val Glu Lys Ala Leu Glu
            20

<210> SEQ ID NO 65
<211> LENGTH: 24
<212> TYPE: PRT
<213> ORGANISM: Artificial sequence
<220> FEATURE:
<223> OTHER INFORMATION: Synthetic polypeptide

<400> SEQUENCE: 65

Ser Gly Ser Gly Leu Arg Arg Asp Leu Asp Ala Ser Arg Glu Ala Lys
1               5                   10                  15
Arg Gln Val Glu Lys Ala Leu Glu
            20

<210> SEQ ID NO 66
<211> LENGTH: 24
<212> TYPE: PRT
<213> ORGANISM: Artificial sequence
<220> FEATURE:
<223> OTHER INFORMATION: Synthetic polypeptide

<400> SEQUENCE: 66

Ser Gly Ser Gly Leu Arg Arg Asp Leu Asp Ala Ser Arg Glu Ala Lys
1               5                   10                  15
Thr Gln Val Glu Lys Ala Leu Glu
            20

<210> SEQ ID NO 67
<211> LENGTH: 24
<212> TYPE: PRT
<213> ORGANISM: Artificial sequence
<220> FEATURE:
<223> OTHER INFORMATION: Synthetic polypeptide

<400> SEQUENCE: 67

Ser Gly Ser Gly Leu Arg Arg Asp Leu Asp Ala Ser Arg Glu Ala Lys
1               5                   10                  15
Lys Glu Val Glu Lys Ala Leu Glu
            20

<210> SEQ ID NO 68
<211> LENGTH: 24
<212> TYPE: PRT
<213> ORGANISM: Artificial sequence
<220> FEATURE:
<223> OTHER INFORMATION: Synthetic polypeptide

<400> SEQUENCE: 68

Ser Gly Ser Gly Leu Arg Arg Asp Leu Asp Ala Ser Arg Glu Ala Lys
1               5                   10                  15
Lys Asp Val Glu Lys Ala Leu Glu
            20

<210> SEQ ID NO 69
```

```
<211> LENGTH: 24
<212> TYPE: PRT
<213> ORGANISM: Artificial sequence
<220> FEATURE:
<223> OTHER INFORMATION: Synthetic polypeptide

<400> SEQUENCE: 69

Ser Gly Ser Gly Leu Arg Arg Asp Leu Asp Ala Ser Arg Glu Ala Lys
1               5                   10                  15

Lys Lys Val Glu Lys Ala Leu Glu
            20

<210> SEQ ID NO 70
<211> LENGTH: 24
<212> TYPE: PRT
<213> ORGANISM: Artificial sequence
<220> FEATURE:
<223> OTHER INFORMATION: Synthetic polypeptide

<400> SEQUENCE: 70

Ser Gly Ser Gly Leu Arg Arg Asp Leu Asp Ala Ser Arg Glu Ala Lys
1               5                   10                  15

Lys Asn Val Glu Lys Ala Leu Glu
            20

<210> SEQ ID NO 71
<211> LENGTH: 24
<212> TYPE: PRT
<213> ORGANISM: Artificial sequence
<220> FEATURE:
<223> OTHER INFORMATION: Synthetic polypeptide

<400> SEQUENCE: 71

Ser Gly Ser Gly Leu Arg Arg Asp Leu Asp Ala Ser Arg Glu Ala Lys
1               5                   10                  15

Lys Arg Val Glu Lys Ala Leu Glu
            20

<210> SEQ ID NO 72
<211> LENGTH: 24
<212> TYPE: PRT
<213> ORGANISM: Artificial sequence
<220> FEATURE:
<223> OTHER INFORMATION: Synthetic polypeptide

<400> SEQUENCE: 72

Ser Gly Ser Gly Leu Arg Arg Asp Leu Asp Ala Ser Arg Glu Ala Lys
1               5                   10                  15

Lys Ala Val Glu Lys Ala Leu Glu
            20

<210> SEQ ID NO 73
<211> LENGTH: 24
<212> TYPE: PRT
<213> ORGANISM: Artificial sequence
<220> FEATURE:
<223> OTHER INFORMATION: Synthetic polypeptide

<400> SEQUENCE: 73

Ser Gly Ser Gly Leu Arg Arg Asp Leu Asp Ala Ser Arg Glu Ala Lys
1               5                   10                  15

Lys Ser Val Glu Lys Ala Leu Glu
            20
```

```
<210> SEQ ID NO 74
<211> LENGTH: 24
<212> TYPE: PRT
<213> ORGANISM: Artificial sequence
<220> FEATURE:
<223> OTHER INFORMATION: Synthetic polypeptide

<400> SEQUENCE: 74

Ser Gly Ser Gly Leu Arg Arg Asp Leu Asp Ala Ser Arg Glu Ala Lys
1               5                   10                  15

Lys Thr Val Glu Lys Ala Leu Glu
            20

<210> SEQ ID NO 75
<211> LENGTH: 24
<212> TYPE: PRT
<213> ORGANISM: Artificial sequence
<220> FEATURE:
<223> OTHER INFORMATION: Synthetic polypeptide

<400> SEQUENCE: 75

Ser Gly Ser Gly Leu Arg Arg Asp Leu Asp Ala Ser Arg Glu Ala Lys
1               5                   10                  15

Lys His Val Glu Lys Ala Leu Glu
            20

<210> SEQ ID NO 76
<211> LENGTH: 24
<212> TYPE: PRT
<213> ORGANISM: Artificial sequence
<220> FEATURE:
<223> OTHER INFORMATION: Synthetic polypeptide

<400> SEQUENCE: 76

Ser Gly Ser Gly Leu Arg Arg Asp Leu Asp Ala Ser Arg Glu Ala Lys
1               5                   10                  15

Lys Gln Leu Glu Lys Ala Leu Glu
            20

<210> SEQ ID NO 77
<211> LENGTH: 24
<212> TYPE: PRT
<213> ORGANISM: Artificial sequence
<220> FEATURE:
<223> OTHER INFORMATION: Synthetic polypeptide

<400> SEQUENCE: 77

Ser Gly Ser Gly Leu Arg Arg Asp Leu Asp Ala Ser Arg Glu Ala Lys
1               5                   10                  15

Lys Gln Ala Glu Lys Ala Leu Glu
            20

<210> SEQ ID NO 78
<211> LENGTH: 24
<212> TYPE: PRT
<213> ORGANISM: Artificial sequence
<220> FEATURE:
<223> OTHER INFORMATION: Synthetic polypeptide

<400> SEQUENCE: 78

Ser Gly Ser Gly Leu Arg Arg Asp Leu Asp Ala Ser Arg Glu Ala Lys
1               5                   10                  15

Lys Gln Tyr Glu Lys Ala Leu Glu
            20
```

<210> SEQ ID NO 79
<211> LENGTH: 24
<212> TYPE: PRT
<213> ORGANISM: Artificial sequence
<220> FEATURE:
<223> OTHER INFORMATION: Synthetic polypeptide

<400> SEQUENCE: 79

Ser Gly Ser Gly Leu Arg Arg Asp Leu Asp Ala Ser Arg Glu Ala Lys
1               5                   10                  15

Lys Gln Met Glu Lys Ala Leu Glu
            20

<210> SEQ ID NO 80
<211> LENGTH: 24
<212> TYPE: PRT
<213> ORGANISM: Artificial sequence
<220> FEATURE:
<223> OTHER INFORMATION: Synthetic polypeptide

<400> SEQUENCE: 80

Ser Gly Ser Gly Leu Arg Arg Asp Leu Asp Ala Ser Arg Glu Ala Lys
1               5                   10                  15

Lys Gln Glu Glu Lys Ala Leu Glu
            20

<210> SEQ ID NO 81
<211> LENGTH: 24
<212> TYPE: PRT
<213> ORGANISM: Artificial sequence
<220> FEATURE:
<223> OTHER INFORMATION: Synthetic polypeptide

<400> SEQUENCE: 81

Ser Gly Ser Gly Leu Arg Arg Asp Leu Asp Ala Ser Arg Glu Ala Lys
1               5                   10                  15

Lys Gln Ile Glu Lys Ala Leu Glu
            20

<210> SEQ ID NO 82
<211> LENGTH: 24
<212> TYPE: PRT
<213> ORGANISM: Artificial sequence
<220> FEATURE:
<223> OTHER INFORMATION: Synthetic polypeptide

<400> SEQUENCE: 82

Ser Gly Ser Gly Leu Arg Arg Asp Leu Asp Ala Ser Arg Glu Ala Lys
1               5                   10                  15

Lys Gln Val Gln Lys Ala Leu Glu
            20

<210> SEQ ID NO 83
<211> LENGTH: 24
<212> TYPE: PRT
<213> ORGANISM: Artificial sequence
<220> FEATURE:
<223> OTHER INFORMATION: Synthetic polypeptide

<400> SEQUENCE: 83

Ser Gly Ser Gly Leu Arg Arg Asp Leu Asp Ala Ser Arg Glu Ala Lys
1               5                   10                  15

Lys Gln Val Lys Lys Ala Leu Glu
            20

<210> SEQ ID NO 84
<211> LENGTH: 24
<212> TYPE: PRT
<213> ORGANISM: Artificial sequence
<220> FEATURE:
<223> OTHER INFORMATION: Synthetic polypeptide

<400> SEQUENCE: 84

Ser Gly Ser Gly Leu Arg Arg Asp Leu Asp Ala Ser Arg Glu Ala Lys
1               5                   10                  15

Lys Gln Val Asn Lys Ala Leu Glu
            20

<210> SEQ ID NO 85
<211> LENGTH: 24
<212> TYPE: PRT
<213> ORGANISM: Artificial sequence
<220> FEATURE:
<223> OTHER INFORMATION: Synthetic polypeptide

<400> SEQUENCE: 85

Ser Gly Ser Gly Leu Arg Arg Asp Leu Asp Ala Ser Arg Glu Ala Lys
1               5                   10                  15

Lys Gln Val Arg Lys Ala Leu Glu
            20

<210> SEQ ID NO 86
<211> LENGTH: 24
<212> TYPE: PRT
<213> ORGANISM: Artificial sequence
<220> FEATURE:
<223> OTHER INFORMATION: Synthetic polypeptide

<400> SEQUENCE: 86

Ser Gly Ser Gly Leu Arg Arg Asp Leu Asp Ala Ser Arg Glu Ala Lys
1               5                   10                  15

Lys Gln Val Thr Lys Ala Leu Glu
            20

<210> SEQ ID NO 87
<211> LENGTH: 24
<212> TYPE: PRT
<213> ORGANISM: Artificial sequence
<220> FEATURE:
<223> OTHER INFORMATION: Synthetic polypeptide

<400> SEQUENCE: 87

Ser Gly Ser Gly Leu Arg Arg Asp Leu Asp Ala Ser Arg Glu Ala Lys
1               5                   10                  15

Lys Gln Val Asp Lys Ala Leu Glu
            20

<210> SEQ ID NO 88
<211> LENGTH: 24
<212> TYPE: PRT
<213> ORGANISM: Artificial sequence
<220> FEATURE:
<223> OTHER INFORMATION: Synthetic polypeptide

<400> SEQUENCE: 88

Ser Gly Ser Gly Leu Arg Arg Asp Leu Asp Ala Ser Arg Glu Ala Lys
1               5                   10                  15

Lys Gln Val Glu Glu Ala Leu Glu

20

<210> SEQ ID NO 89
<211> LENGTH: 24
<212> TYPE: PRT
<213> ORGANISM: Artificial sequence
<220> FEATURE:
<223> OTHER INFORMATION: Synthetic polypeptide

<400> SEQUENCE: 89

Ser Gly Ser Gly Leu Arg Arg Asp Leu Asp Ala Ser Arg Glu Ala Lys
1               5                   10                  15

Lys Gln Val Glu Asn Ala Leu Glu
            20

<210> SEQ ID NO 90
<211> LENGTH: 24
<212> TYPE: PRT
<213> ORGANISM: Artificial sequence
<220> FEATURE:
<223> OTHER INFORMATION: Synthetic polypeptide

<400> SEQUENCE: 90

Ser Gly Ser Gly Leu Arg Arg Asp Leu Asp Ala Ser Arg Glu Ala Lys
1               5                   10                  15

Lys Gln Val Glu Arg Ala Leu Glu
            20

<210> SEQ ID NO 91
<211> LENGTH: 24
<212> TYPE: PRT
<213> ORGANISM: Artificial sequence
<220> FEATURE:
<223> OTHER INFORMATION: Synthetic polypeptide

<400> SEQUENCE: 91

Ser Gly Ser Gly Leu Arg Arg Asp Leu Asp Ala Ser Arg Glu Ala Lys
1               5                   10                  15

Lys Gln Val Glu Asp Ala Leu Glu
            20

<210> SEQ ID NO 92
<211> LENGTH: 24
<212> TYPE: PRT
<213> ORGANISM: Artificial sequence
<220> FEATURE:
<223> OTHER INFORMATION: Synthetic polypeptide

<400> SEQUENCE: 92

Ser Gly Ser Gly Leu Arg Arg Asp Leu Asp Ala Ser Arg Glu Ala Lys
1               5                   10                  15

Lys Gln Val Glu Gln Ala Leu Glu
            20

<210> SEQ ID NO 93
<211> LENGTH: 24
<212> TYPE: PRT
<213> ORGANISM: Artificial sequence
<220> FEATURE:
<223> OTHER INFORMATION: Synthetic polypeptide

<400> SEQUENCE: 93

Ser Gly Ser Gly Leu Arg Arg Asp Leu Asp Ala Ser Arg Glu Ala Lys
1               5                   10                  15

Lys Gln Val Glu Ala Ala Leu Glu
            20

<210> SEQ ID NO 94
<211> LENGTH: 24
<212> TYPE: PRT
<213> ORGANISM: Artificial sequence
<220> FEATURE:
<223> OTHER INFORMATION: Synthetic polypeptide

<400> SEQUENCE: 94

Ser Gly Ser Gly Leu Arg Arg Asp Leu Asp Ala Ser Arg Glu Ala Lys
1               5                   10                  15

Lys Gln Val Glu Ser Ala Leu Glu
            20

<210> SEQ ID NO 95
<211> LENGTH: 24
<212> TYPE: PRT
<213> ORGANISM: Artificial sequence
<220> FEATURE:
<223> OTHER INFORMATION: Synthetic polypeptide

<400> SEQUENCE: 95

Ser Gly Ser Gly Leu Arg Arg Asp Leu Asp Ala Ser Arg Glu Ala Lys
1               5                   10                  15

Lys Gln Val Glu Thr Ala Leu Glu
            20

<210> SEQ ID NO 96
<211> LENGTH: 24
<212> TYPE: PRT
<213> ORGANISM: Artificial sequence
<220> FEATURE:
<223> OTHER INFORMATION: Synthetic polypeptide

<400> SEQUENCE: 96

Ser Gly Ser Gly Leu Arg Arg Asp Leu Asp Ala Ser Arg Glu Ala Lys
1               5                   10                  15

Lys Gln Val Glu Met Ala Leu Glu
            20

<210> SEQ ID NO 97
<211> LENGTH: 24
<212> TYPE: PRT
<213> ORGANISM: Artificial sequence
<220> FEATURE:
<223> OTHER INFORMATION: Synthetic polypeptide

<400> SEQUENCE: 97

Ser Gly Ser Gly Leu Arg Arg Asp Leu Asp Ala Ser Arg Glu Ala Lys
1               5                   10                  15

Lys Gln Val Glu Lys Glu Leu Glu
            20

<210> SEQ ID NO 98
<211> LENGTH: 24
<212> TYPE: PRT
<213> ORGANISM: Artificial sequence
<220> FEATURE:
<223> OTHER INFORMATION: Synthetic polypeptide

<400> SEQUENCE: 98

Ser Gly Ser Gly Leu Arg Arg Asp Leu Asp Ala Ser Arg Glu Ala Lys
1               5                   10                  15

-continued

Lys Gln Val Glu Lys Lys Leu Glu
            20

<210> SEQ ID NO 99
<211> LENGTH: 24
<212> TYPE: PRT
<213> ORGANISM: Artificial sequence
<220> FEATURE:
<223> OTHER INFORMATION: Synthetic polypeptide

<400> SEQUENCE: 99

Ser Gly Ser Gly Leu Arg Arg Asp Leu Asp Ala Ser Arg Glu Ala Lys
1               5                   10                  15

Lys Gln Val Glu Lys Gln Leu Glu
            20

<210> SEQ ID NO 100
<211> LENGTH: 24
<212> TYPE: PRT
<213> ORGANISM: Artificial sequence
<220> FEATURE:
<223> OTHER INFORMATION: Synthetic polypeptide

<400> SEQUENCE: 100

Ser Gly Ser Gly Leu Arg Arg Asp Leu Asp Ala Ser Arg Glu Ala Lys
1               5                   10                  15

Lys Gln Val Glu Lys Asn Leu Glu
            20

<210> SEQ ID NO 101
<211> LENGTH: 24
<212> TYPE: PRT
<213> ORGANISM: Artificial sequence
<220> FEATURE:
<223> OTHER INFORMATION: Synthetic polypeptide

<400> SEQUENCE: 101

Ser Gly Ser Gly Leu Arg Arg Asp Leu Asp Ala Ser Arg Glu Ala Lys
1               5                   10                  15

Lys Gln Val Glu Lys Arg Leu Glu
            20

<210> SEQ ID NO 102
<211> LENGTH: 24
<212> TYPE: PRT
<213> ORGANISM: Artificial sequence
<220> FEATURE:
<223> OTHER INFORMATION: Synthetic polypeptide

<400> SEQUENCE: 102

Ser Gly Ser Gly Leu Arg Arg Asp Leu Asp Ala Ser Arg Glu Ala Lys
1               5                   10                  15

Lys Gln Val Glu Lys Asp Leu Glu
            20

<210> SEQ ID NO 103
<211> LENGTH: 24
<212> TYPE: PRT
<213> ORGANISM: Artificial sequence
<220> FEATURE:
<223> OTHER INFORMATION: Synthetic polypeptide

<400> SEQUENCE: 103

Ser Gly Ser Gly Leu Arg Arg Asp Leu Asp Ala Ser Arg Glu Ala Lys

```
                1               5                   10                  15

Lys Gln Val Glu Lys Ala Ile Glu
            20

<210> SEQ ID NO 104
<211> LENGTH: 24
<212> TYPE: PRT
<213> ORGANISM: Artificial sequence
<220> FEATURE:
<223> OTHER INFORMATION: Synthetic polypeptide

<400> SEQUENCE: 104

Ser Gly Ser Gly Leu Arg Arg Asp Leu Asp Ala Ser Arg Glu Ala Lys
1               5                   10                  15

Lys Gln Val Glu Lys Ala Met Glu
            20

<210> SEQ ID NO 105
<211> LENGTH: 24
<212> TYPE: PRT
<213> ORGANISM: Artificial sequence
<220> FEATURE:
<223> OTHER INFORMATION: Synthetic polypeptide

<400> SEQUENCE: 105

Ser Gly Ser Gly Leu Arg Arg Asp Leu Asp Ala Ser Arg Glu Ala Lys
1               5                   10                  15

Lys Gln Val Glu Lys Ala Val Glu
            20

<210> SEQ ID NO 106
<211> LENGTH: 24
<212> TYPE: PRT
<213> ORGANISM: Artificial sequence
<220> FEATURE:
<223> OTHER INFORMATION: Synthetic polypeptide

<400> SEQUENCE: 106

Ser Gly Ser Gly Leu Arg Arg Asp Leu Asp Ala Ser Arg Glu Ala Lys
1               5                   10                  15

Lys Gln Val Glu Lys Ala Tyr Glu
            20

<210> SEQ ID NO 107
<211> LENGTH: 24
<212> TYPE: PRT
<213> ORGANISM: Artificial sequence
<220> FEATURE:
<223> OTHER INFORMATION: Synthetic polypeptide

<400> SEQUENCE: 107

Ser Gly Ser Gly Leu Arg Arg Asp Leu Asp Ala Ser Arg Glu Ala Lys
1               5                   10                  15

Lys Gln Val Glu Lys Ala Lys Glu
            20

<210> SEQ ID NO 108
<211> LENGTH: 24
<212> TYPE: PRT
<213> ORGANISM: Artificial sequence
<220> FEATURE:
<223> OTHER INFORMATION: Synthetic polypeptide

<400> SEQUENCE: 108
```

```
Ser Gly Ser Gly Leu Arg Arg Asp Leu Asp Ala Ser Arg Glu Ala Lys
1               5                   10                  15

Lys Gln Val Glu Lys Ala Ala Glu
            20
```

<210> SEQ ID NO 109
<211> LENGTH: 24
<212> TYPE: PRT
<213> ORGANISM: Artificial sequence
<220> FEATURE:
<223> OTHER INFORMATION: Synthetic polypeptide

<400> SEQUENCE: 109

```
Ser Gly Ser Gly Leu Arg Arg Asp Leu Asp Ala Ser Arg Glu Ala Lys
1               5                   10                  15

Lys Gln Val Glu Lys Ala Asn Glu
            20
```

<210> SEQ ID NO 110
<211> LENGTH: 24
<212> TYPE: PRT
<213> ORGANISM: Artificial sequence
<220> FEATURE:
<223> OTHER INFORMATION: Synthetic polypeptide

<400> SEQUENCE: 110

```
Ser Gly Ser Gly Leu Arg Arg Asp Leu Asp Ala Ser Arg Glu Ala Lys
1               5                   10                  15

Lys Gln Val Glu Lys Ala Arg Glu
            20
```

<210> SEQ ID NO 111
<211> LENGTH: 24
<212> TYPE: PRT
<213> ORGANISM: Artificial sequence
<220> FEATURE:
<223> OTHER INFORMATION: Synthetic polypeptide

<400> SEQUENCE: 111

```
Ser Gly Ser Gly Glu Gly Lys Val Ser Thr Leu Pro Leu Asp Ile Gln
1               5                   10                  15

Ile Ile Ala Ala Thr Met Ser Lys
            20
```

<210> SEQ ID NO 112
<211> LENGTH: 24
<212> TYPE: PRT
<213> ORGANISM: Artificial sequence
<220> FEATURE:
<223> OTHER INFORMATION: Synthetic polypeptide

<400> SEQUENCE: 112

```
Ser Gly Ser Gly Leu Arg Arg Asp Leu Asp Ala Ser Arg Glu Ala Lys
1               5                   10                  15

Lys Gln Val Glu Lys Ala Leu Glu
            20
```

<210> SEQ ID NO 113
<211> LENGTH: 24
<212> TYPE: PRT
<213> ORGANISM: Artificial sequence
<220> FEATURE:
<223> OTHER INFORMATION: Synthetic polypeptide

<400> SEQUENCE: 113

```
Ser Gly Ser Gly Leu Arg Arg Asp Leu Asp Ala Ser Arg Glu Ala Lys
1               5                   10                  15

Lys Gln Val Glu Lys Ala Leu Glu
            20

<210> SEQ ID NO 114
<211> LENGTH: 4
<212> TYPE: PRT
<213> ORGANISM: Artificial sequence
<220> FEATURE:
<223> OTHER INFORMATION: Synthetic polypeptide

<400> SEQUENCE: 114

Ser Gly Ser Gly
1
```

IMMUNOGENIC PEPTIDE AGAINST GROUP A *STREPTOCOCCUS*

This application is a national phase application under 35 U.S.C. § 371 of International Application No. PCT/AU2018/050893, filed Aug. 22, 2018, which claims the benefit of Netherlands Patent Application No. 2019439, filed Aug. 23, 2017, the entirety of each of which is incorporated herein by reference.

Pursuant to 37 C.F.R. 1.821(c), a sequence listing is submitted herewith as an ASCII compliant text file named "FBRIP0002US_ST25.txt", created on Dec. 12, 2022 and having a size of ~36 kilobytes. The content of the aforementioned file is hereby incorporated by reference in its entirety.

TECHNICAL FIELD

THIS INVENTION relates to an immunogenic peptide for prevention and treatment of group A *streptococcus* streptococcus-associated diseases and conditions.

BACKGROUND

Synthetic and recombinant peptides are being developed as vaccines to prevent and protect against numerous infectious as well as non-infectious diseases. Their utility resides in their ability to mimic native epitopes on foreign or host proteins and to specifically activate or modulate protective or harmful immune responses. Significant progress has been made for many non-infectious diseases including cancer, allergies, multiple sclerosis and chronic diseases such as hypertension, diabetes and Alzheimer's disease (1). However, their greatest promise lies in vaccines to prevent infectious diseases. Here, their small size greatly facilitates the design of multi-component vaccines incorporating epitopes from multiple target antigens (2), vaccines that can prevent infections with organisms that exist in multiple allelic forms (3), and vaccines that can target hidden or cryptic epitopes resulting in the production of immune responses that are not induced naturally by the organism but which are lethal to the organism once induced by the vaccine (4).

Epitopes recognized by B and T cells are small and can, due to their size, be easily and inexpensively synthesized. However, because they are small the repertoire of B or T cells that they stimulate is very limited and it is primarily for this reason that no peptide-based vaccines have yet been developed and licensed for human use.

Vaccines against *Streptococcus pyogenes* (the Lancefield group A *streptococcus*; GAS) have long been sought due to the debilitating diseases caused by the bacterium, particularly rheumatic fever and rheumatic heart disease. Rheumatic fever is an uncommon disease today in most developed countries but it remains the major cause of acquired heart disease in children, adolescents and young adults in the developing world. In addition, invasive GAS disease is a frequent cause of sepsis in children and adults and has a high-case fatality rate. Further adding to the burden of GAS disease is post-streptococcal glomerulonephritis, which likely contributes to the high rates of end-stage renal failure in many GAS endemic regions. GAS pharyngitis and impetigo are responsible for the greatest absolute number of GAS infections each year. GAS pharyngitis affects approximately 8%-15% of school-aged children per year and GAS impetigo is a very common infection in children prevalence of 10-50%. Not only are severe GAS-associated diseases a problem in developing countries, but even in developed countries particularly virulent GAS strains have emerged that are resistant to standard antibiotic therapies and cause debilitating diseases such as severe necrotizing fasciitis.

Peptide-based vaccines against group A *streptococcus* have focused on M protein-derived peptides such as p145, J8 and J14 peptides. Currently, J8 peptide which comprises a twelve amino acid minimal epitope within p145 in embedded in a yeast-derived helical peptide (GCN4) amino acid sequence is a leading vaccine candidate (12). The GCN4 amino acid sequence assists maintenance of peptide helicity so as to optimize display of the minimal epitope to the immune system. This vaccine candidate also requires three doses to induce protection against skin disease (19).

SUMMARY

Surprisingly, the present inventors have discovered that the immunogenicity of a p145 peptide can be substantially increased by targeted modification of the amino acid sequence of p145 Immunization with a single dose of the modified p145 peptide, rather than multiple immunizations, can protect against group A *streptococcus* infection even by hypervirulent strains such as the CovR/S mutant strain. Unexpectedly, the modified p145 peptide, fragment or variant elicits a mucosal immune response upon administration to the mammal The mucosal immune response is characterized by the production of IgG, while IgA production is substantially absent or at a relatively reduced level compared to the level of IgG produced.

The invention is broadly directed to a p145 peptide comprising one or more amino acid sequence modifications that substantially improve or enhance immunogenicity, particularly for eliciting mucosal immune responses. In a preferred form, the peptide comprises the amino acid sequence set forth in SEQ ID NO:1.

An aspect of the invention provides a method of eliciting an immune response to group A streptococcal bacteria in a mammal, said method including the step of administering: an isolated protein comprising a modified p145 peptide amino acid sequence comprising an amino acid substitution of residues 13 and 17 of SEQ ID NO:3; an antibody or antibody fragment that binds or is raised against the isolated protein or fragment or variant thereof; or an isolated nucleic acid encoding the isolated protein or fragment or variant thereof; to the mammal to thereby elicit the immune response.

Another aspect of the invention provides a method of inducing immunity against a group A streptococcal bacterial infection in a mammal, said method including the step of administering: an isolated protein comprising a modified p145 peptide amino acid sequence comprising an amino acid substitution of residues 13 and 17 of SEQ ID NO:3; an antibody or antibody fragment that binds or is raised against the isolated protein or fragment or variant thereof; or an isolated nucleic acid encoding the isolated protein or fragment or variant thereof; to the mammal to thereby induce immunity against the group A streptococcal bacterial infection in the mammal.

A further aspect of the invention provides a method of treating or preventing a group A streptococcal bacterial infection in a mammal, said method including the step of administering: an isolated protein comprising a modified p145 peptide amino acid sequence comprising an amino acid substitution of residues 13 and 17 of SEQ ID NO:3; an antibody or antibody fragment that binds or is raised against the isolated protein or fragment or variant thereof; or an isolated nucleic acid encoding the isolated protein or fragment or variant thereof; to the mammal to thereby prevent or treat the group A streptococcal bacterial infection in the mammal.

The modified p145 peptide, fragment or variant suitably comprises an asparagine (N) amino acid at residue 13 and an arginine (R) amino acid at residue 17.

In an embodiment, the modified p145 peptide, fragment or variant of comprises the amino acid sequence set forth in SEQ ID NO:1

In an embodiment, the modified p145 peptide fragment comprises the amino acid sequence set forth in SEQ ID NO:2.

Preferably, the modified p145 peptide, fragment or variant elicits a mucosal immune response upon administration to the mammal.

Suitably, the mucosal immune response is characterized by the production of IgG. Typically, IgA production is substantially absent or at a relatively reduced level compared to the level of IgG produced.

Preferably, the modified p145 peptide, fragment or variant elicits a mucosal immune response upon intramuscular administration to the mammal.

Preferably, the mammal of the aforementioned aspects is a human.

In a particular embodiment of the aforementioned aspects, the modified p145 peptide, fragment or variant may be administered in combination with an immunogenic fragment of a SpyCEP protein. Preferably, the fragment of SpyCEP is, or comprises an S2 peptide (SEQ ID NO:23) or a variant such as a K4S2 peptide (SEQ ID NO:24).

A related aspect of the invention therefore provides a composition comprising: an isolated protein comprising a modified p145 peptide amino acid sequence comprising an amino acid substitution of residues 13 and 17 of SEQ ID NO:3, a fragment or variant thereof, an antibody or antibody fragment that binds or is raised against the isolated protein or fragment or variant thereof or an isolated nucleic acid encoding the isolated protein or fragment or variant thereof; and an immunogenic fragment of a SpyCEP protein or variant thereof, an antibody or antibody fragment that binds or is raised against the SpyCEP immunogenic fragment or variant thereof or an isolated nucleic acid that encodes the SpyCEP immunogenic fragment or variant thereof.

Suitably, the modified p145 peptide amino acid sequence comprises an asparagine (N) amino acid at residue 13 and an arginine (R) amino acid at residue 17, preferably comprising the amino acid sequence set forth in SEQ ID NO: 1. Preferably, the fragment of the modified p145 peptide comprises the amino acid sequence set forth in SEQ ID NO:2.

In a preferred embodiment, the fragment of SpyCEP is, or comprises an S2 peptide comprising the amino acid sequence set forth in SEQ ID NO:23, or a variant thereof. The variant may be a K4S2 peptide comprising the amino acid sequence set forth in SEQ ID NO:24.

As used herein, the indefinite articles 'a' and 'an' are used here to refer to or encompass singular or plural elements or features and should not be taken as meaning or defining "one" or a "single" element or feature.

Unless the context requires otherwise, the terms "comprise", "comprises" and "comprising", or similar terms are intended to mean a non-exclusive inclusion, such that a recited list of elements or features does not include those stated or listed elements solely, but may include other elements or features that are not listed or stated.

By "consisting essentially of" in the context of an amino acid sequence is meant the recited amino acid sequence together with an additional one, two or three amino acids at the N- or C-terminus.

The horizontal line in the figure denotes relative binding of various peptide-specific IgG to p145 in comparison to p145 IgG. ANOVA with the Tukey's post hoc method was used to determine the significance in comparison to p145. (C) Representative histograms demonstrating binding of p*17-specific IgG to GAS 2031, 88/30 and JRS145 (an M-negative GAS strain) are shown.

Figure 4:
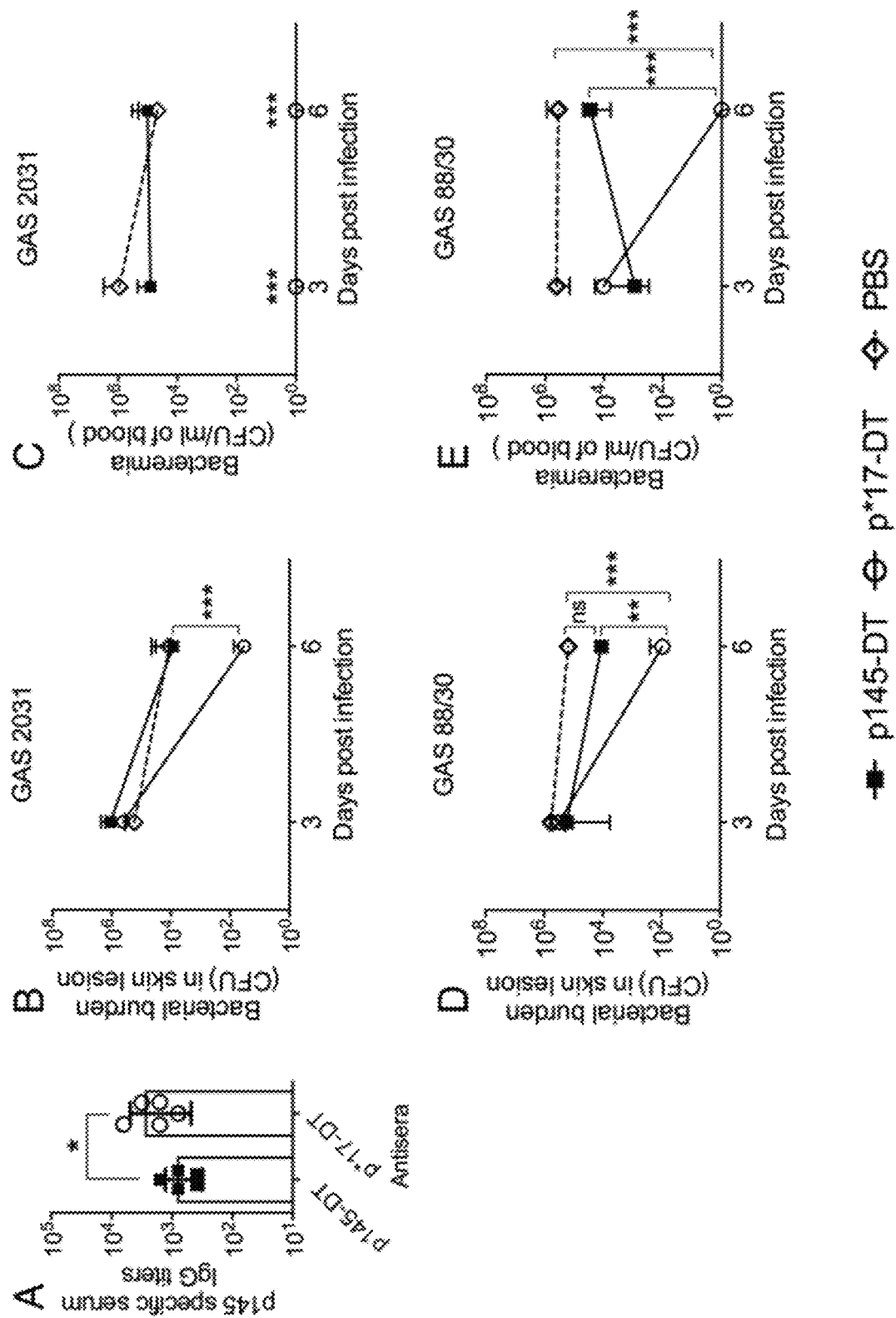

FIG. 4: Immunogenicity and protective efficacy of p145-DT and its variant p*17-DT in protection against superficial skin infection with various GAS strains: Cohorts of BALB/c mice (n=10 mice each) were immunized subcutaneously with 30 μg of p145-DT or p*17-DT or PBS—Alum formulations on day 0. Serum samples were collected at 1 day 20 post-immunisation to assess p145 specific IgG response. Data from some representative mice (n=5) are shown (A). On day 21, the mice were challenged via the skin route of infection with GAS 2031 (B and C) or GAS 88/30 (D and E). On day 3 and 6 post-infection, 5 mice/group were sacrificed and samples collected to determine GAS bacterial burden in the skin (B and D) and the blood (C and E). The results are shown as mean±SEM for 5 mice in each group at each time point. ANOVA with the Tukey's post hoc method was used to determine the significance between all the treated and control cohorts at each time point. $*p<0.05$, $***p<0.001$.

Figure 5A:
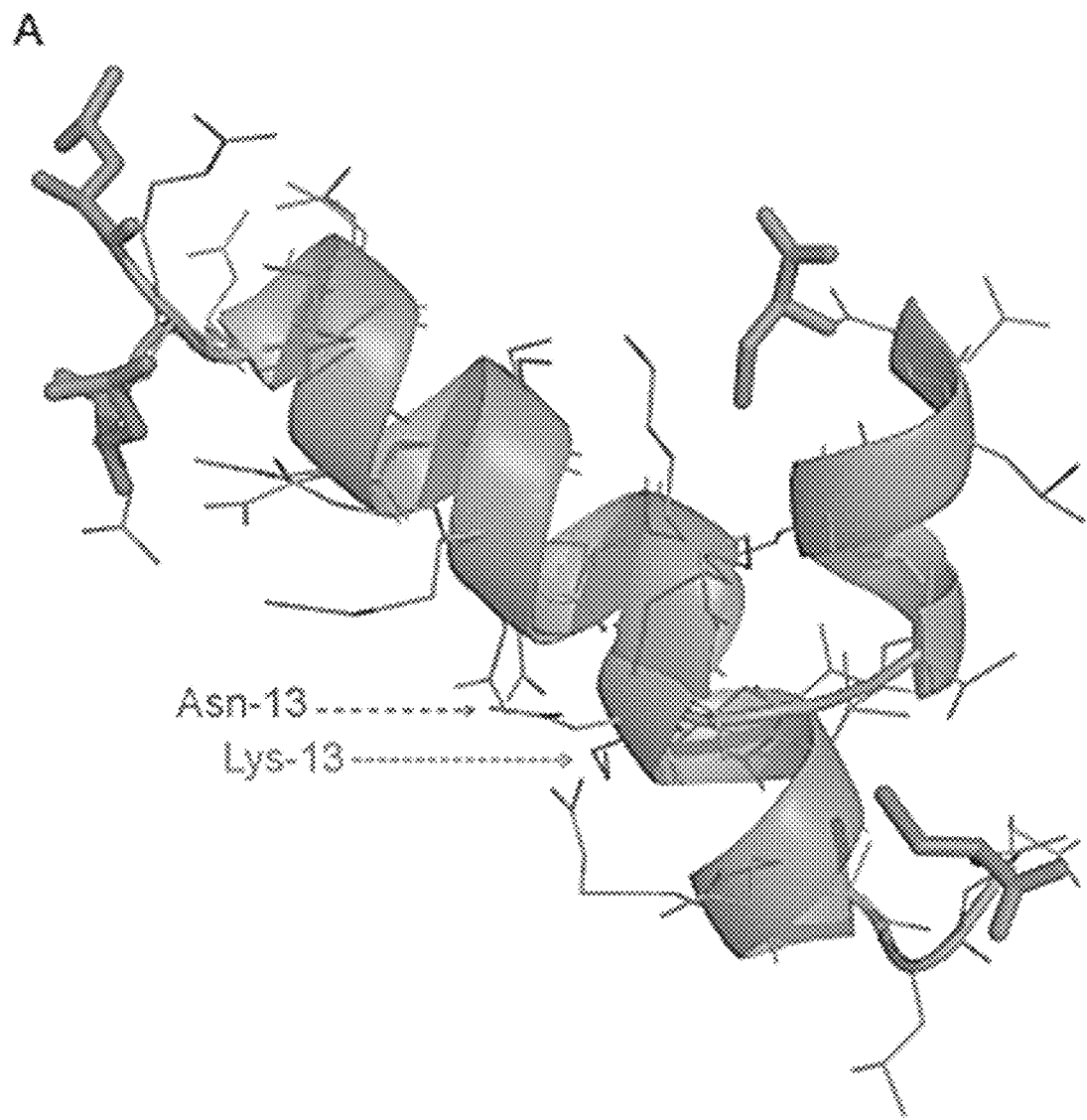
Figure 5B:
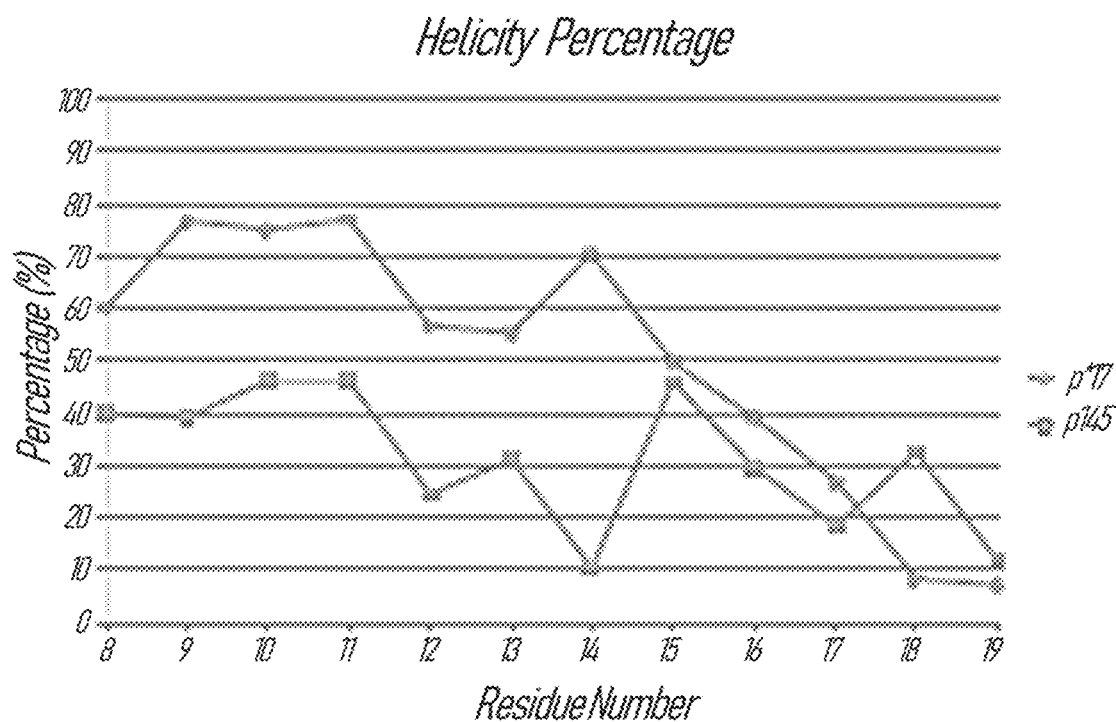
Figure 5C:
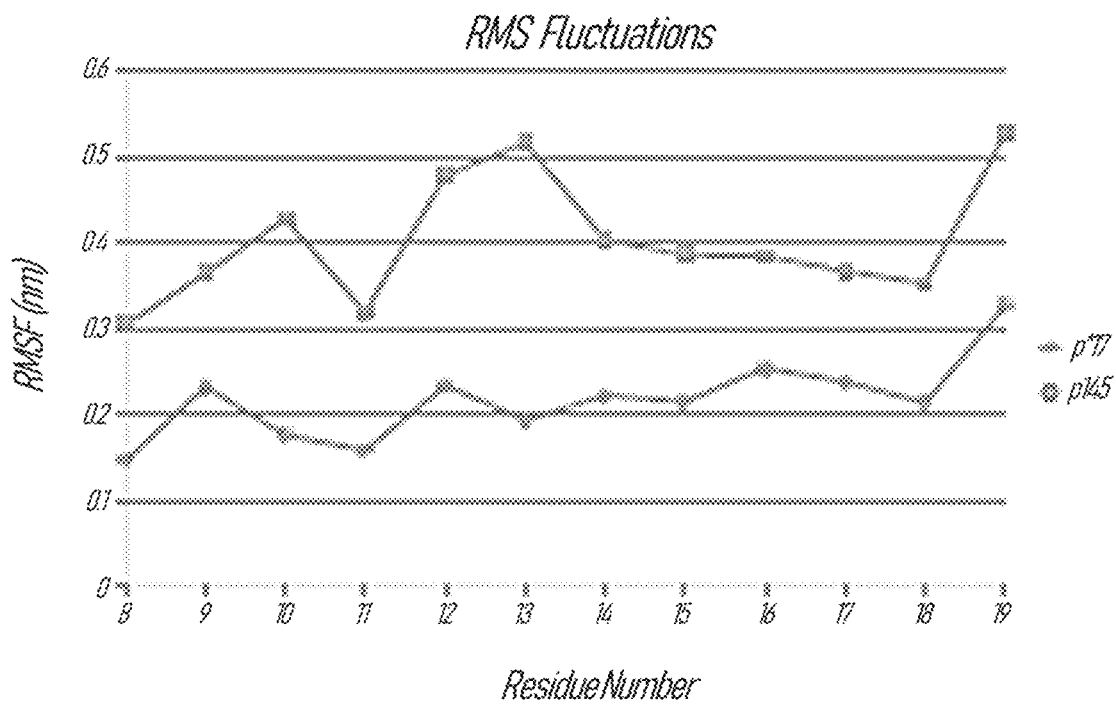

FIG. 5: Structures of p145 and p*17 peptides: Overlay of representative structures of p145 (magenta) and p*17 (green) obtained from 50 ns MD simulations with alignment based on CA of residues 3 to 13 (C-terminal amino acids shown in red, N-terminal amino acids in blue (A). Lys-13 13 breaks the helical character in p145. The probability of the peptides to adopt a helical conformation are shown in (B) revealing that p145 is significantly less likely to form a helical conformation compared to p*17. Root mean square fluctuations (RMSF) of p145, and p*17 in comparison are shown in (C). p145 shows significantly higher fluctuations compared to p*17. The largest difference in flexibility can be seen for Lys-13 in p145 compared to Asn-13 in p*17.

Figure 6:
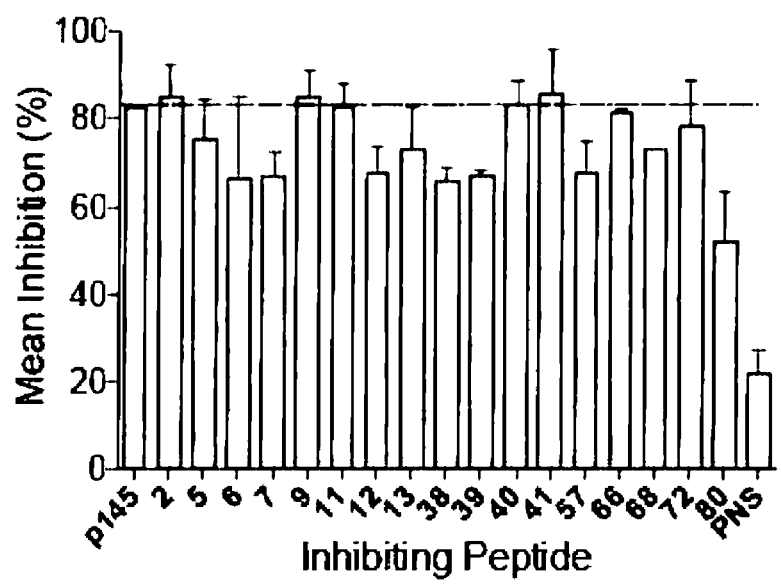

FIG. 6: Identification of immunodominant peptides within the p145 variants library: Peptide-inhibition ELISAs were performed to identify the immunodominant peptides within the pool of p145 variants. Selected peptides at a concentration of 2.5 μg/ml were incubated with p145 antisera. The serum was then used in an ELISA against immobilised p145. Antigen (p145)-specific serum was collected from hyper-immunised B10.D2 mice. Data for each bar are means±SEM.

Figure 7:
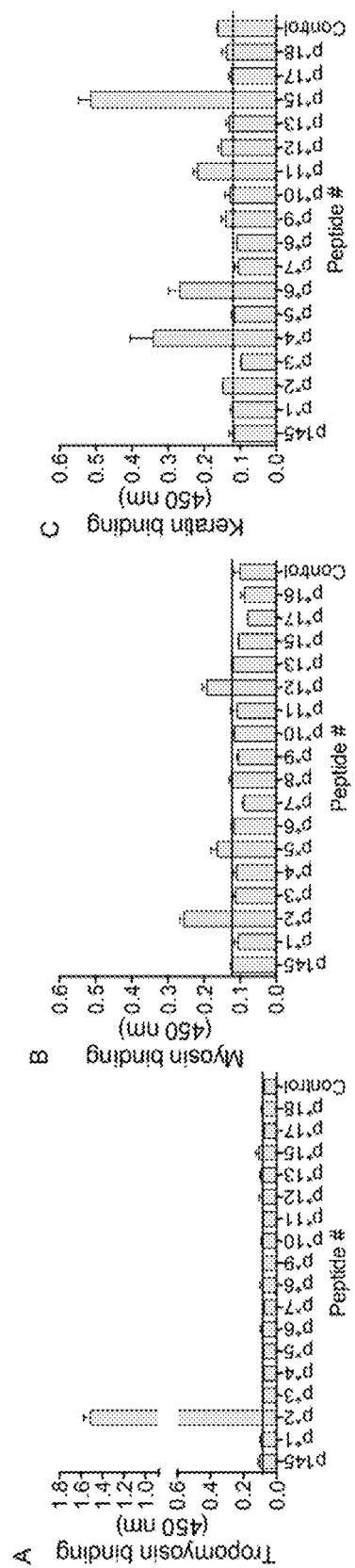

FIG. 7: Cross-reactivity of peptide antisera with human proteins: ELISA was used to determine cross-reactivity of the doubly mutated peptide (L2) anti-sera to human derived proteins (a) tropomyosin, (b) myosin and (c) keratin. Mean absorbance (450 nm)±SEM shown.

Figure 8:
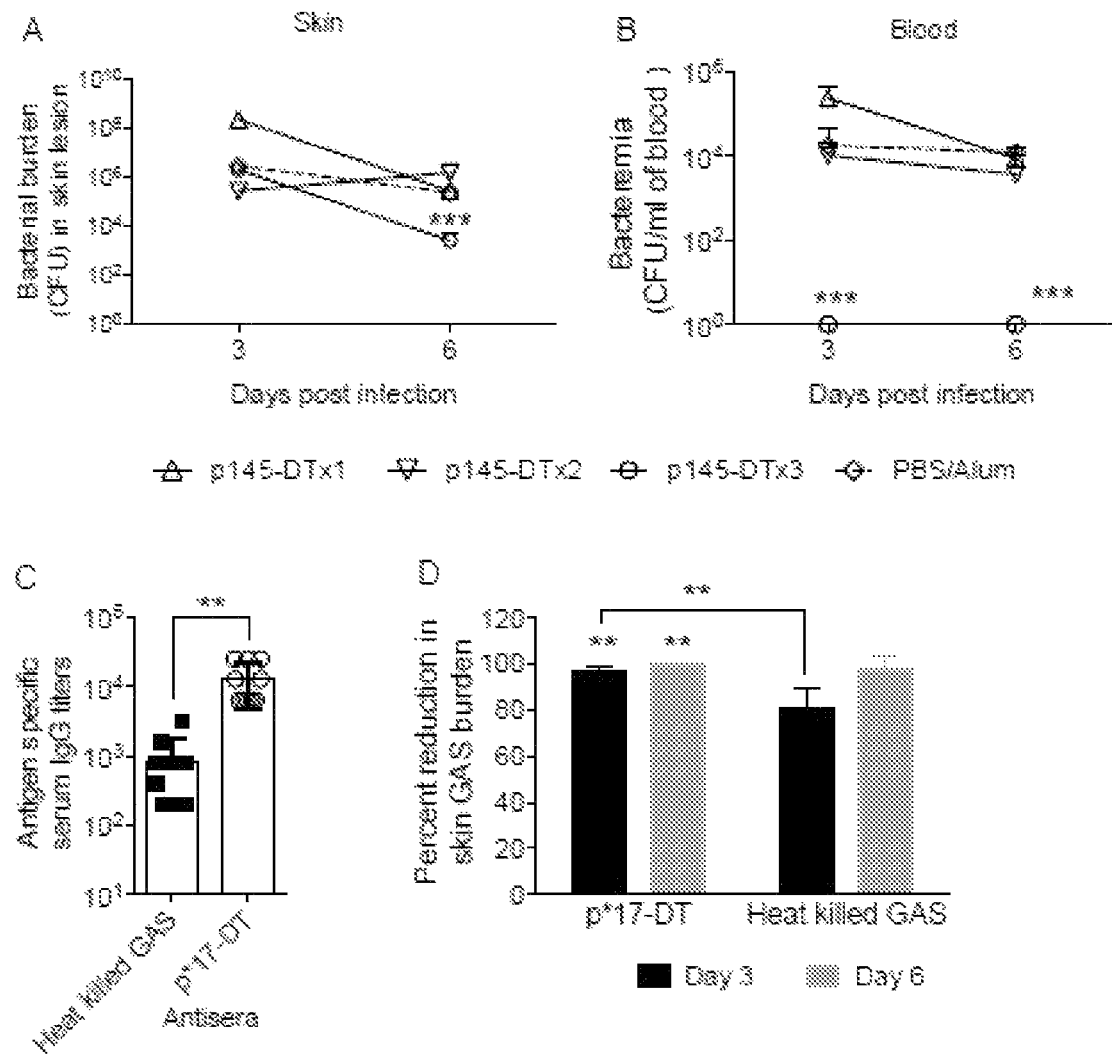

FIG. 8: Protective efficacy of p145-DT in BALB/c mice following 1, 2 or 3 immunisations: Cohorts of BALB/c mice (10 mice/group) received 1, 2 or 3 subcutaneous injections of p145-DT or PBS with adjuvant on days 0, 21 and 28. Efficacy of the vaccine following skin challenge with 88/30 GAS was assessed. Bacterial burden in skin (A) and blood (B) for days 3 and 6 post-infection respectively for cohorts of mice is shown. Protective efficacy of p*17-DT following single immunisation: (C) Cohorts of BALB/c mice (10 mice/group) received a single immunisation with p*17-DT, heat killed GAS (2031) or PBS with adjuvant on days 0. The antigen-specific IgG titers were determined on day-20 post-immunisation. The titers for mice immunised with heat-killed GAS 1 were tested against recombinant M1 protein immobilised on ELISA plate. Mann-Whitney test was used to determine significance between the two vaccinated groups where $**p<0.01$. (D) On day 21 post immunisation, mice were challenged with CovR/S mutant 5448AP GAS via the skin route of infection. The skin samples were assessed for bacterial burden on day-3 and -6 post infection. Percent reduction in bacterial counts in p*17-DT or heat killed GAS immunised cohort in comparison to PBS control cohort are shown. ANOVA with the Tukey's post hoc method was used to determine the significance between all the vaccinated and control cohorts at each time point. $p<0.01$, $*p<0.001$.

FIG. 9: Intramuscular immunization schedule. Mice were immunized three (3) times with p*17-DT+K4S2-DT/Alum and intranasal challenge with 5448AP (CovR/S MT strain).

Figure 10:
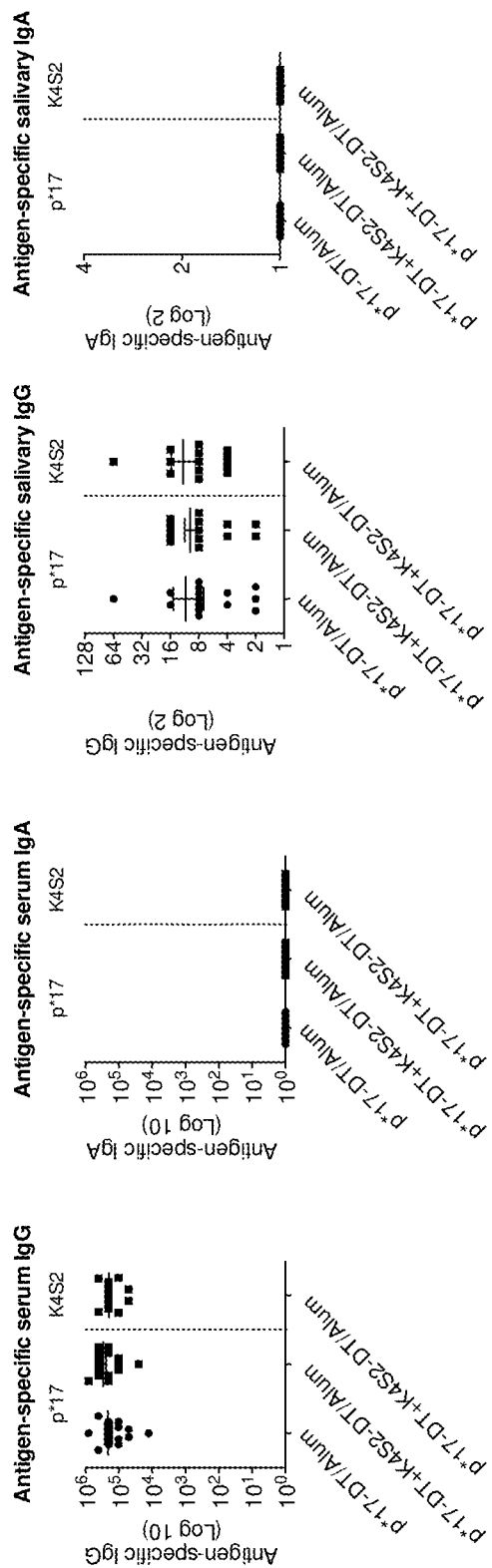

FIG. 10: Immunogenicity following i.m. immunisation with p*17-based vaccines. BALB/c mice (n=15/group; female, 4-6 weeks old) were immunised i.m. with p*17-DT/Alum, p*17-DT+K4S2-DT/Alum and PBS/Alum on days 0, 21 and 42. One week post last boost serum and saliva samples were collected and p*17-specific IgG (A & C) and IgA (B & D) antibody responses were measured by ELISA and are represented as mean±SEM. The titers are in comparison to the control cohort that received only PBS/Alum.

Figure 11:
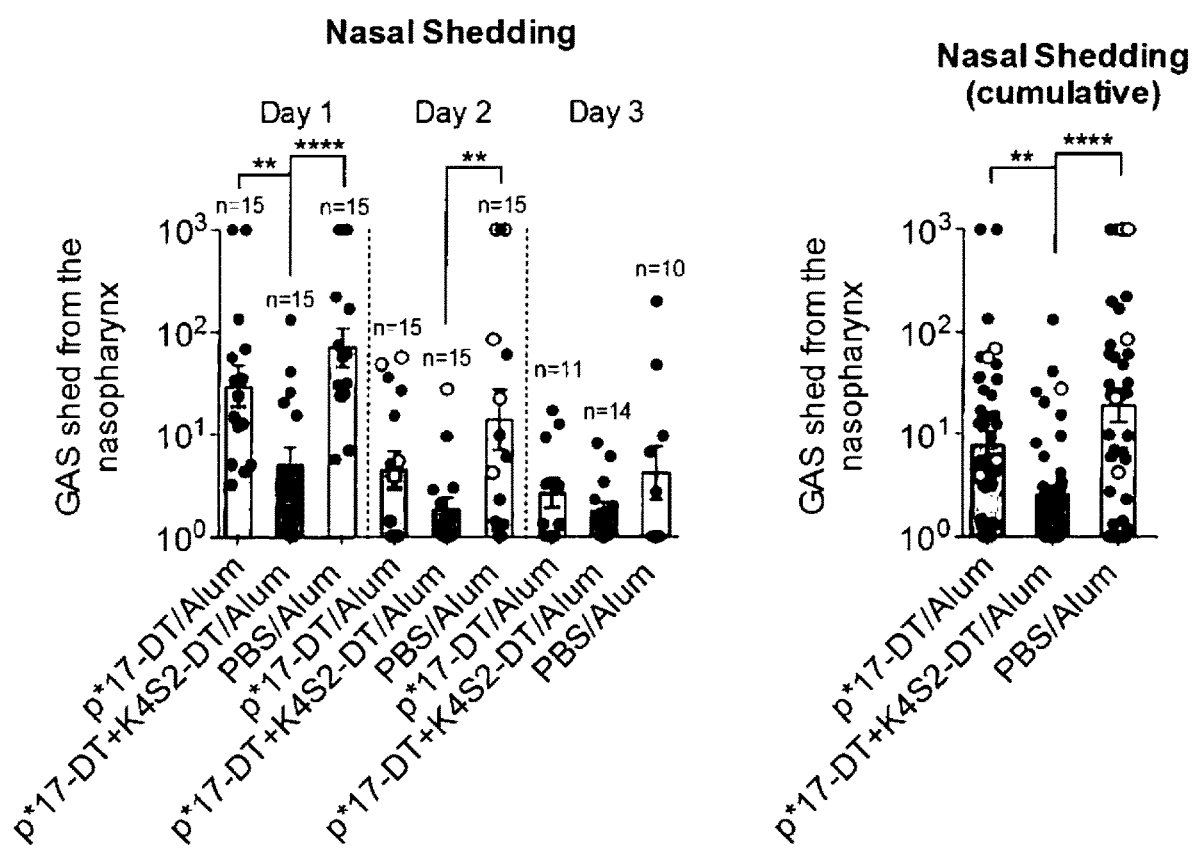

FIG. 11: Protection following intranasal infection. Two weeks after last vaccine boost, the mice were infected intranasally with covR/S mutant GAS (5448AP). On days 1-3 nasal shedding (NS) were collected. Bacterial burden in NS were determined by pressing the nares of each mouse onto columbia blood agar (CBA) plates containing 5% defibrinated horse-blood and exhaled particles were streaked out. On days 1-3 NS were collected and represented as the log transformed mean±SEM from each individual day (A) and as cumulative CFUs from all three days combined (B). o indicates mice culled on day 2 after 15% or more weight loss.

Figure 12:
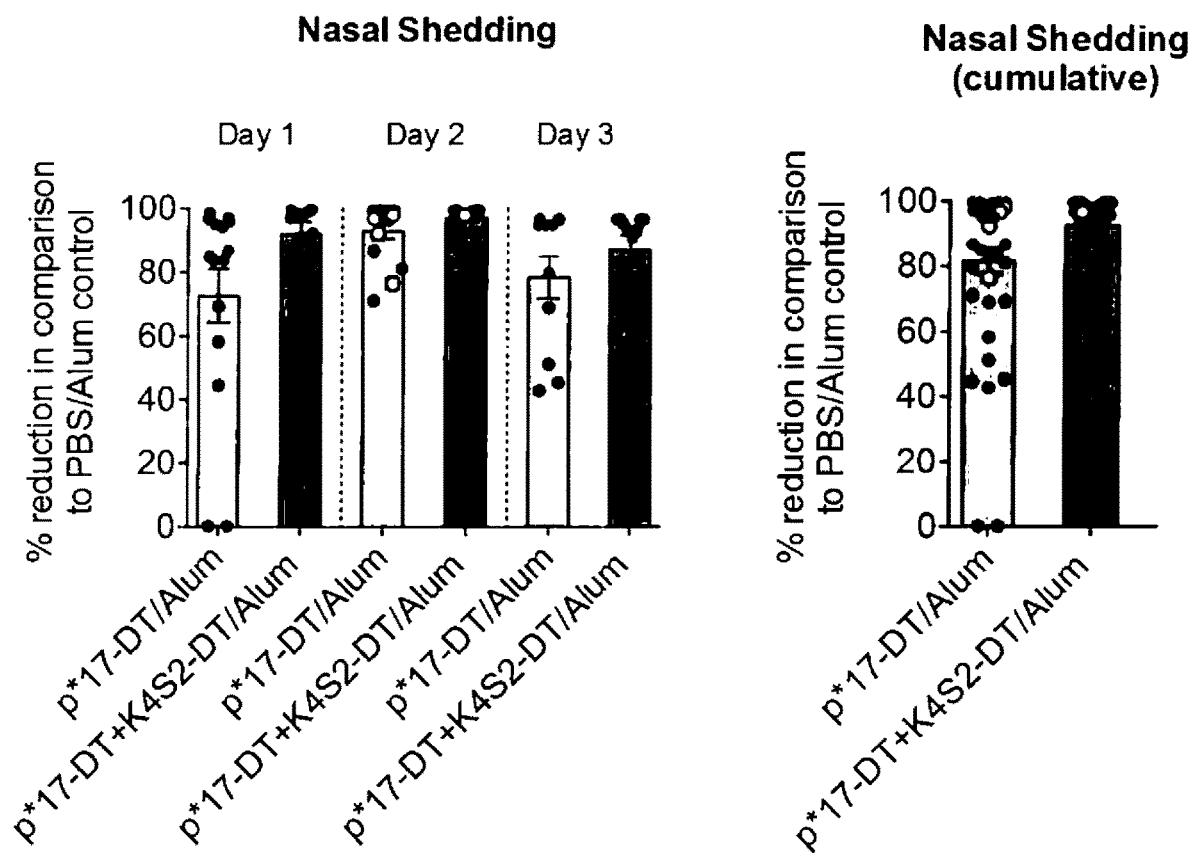

FIG. 12: Percent reduction in bacterial burden the nasal shedding. Percent reduction was calculated in comparison to total mean of the PBS/Alum control from each individual day (A) and as cumulative reduction from all three days combined (B). o indicates mice culled on day 2 after 15% or more weight loss.

Figure 13:
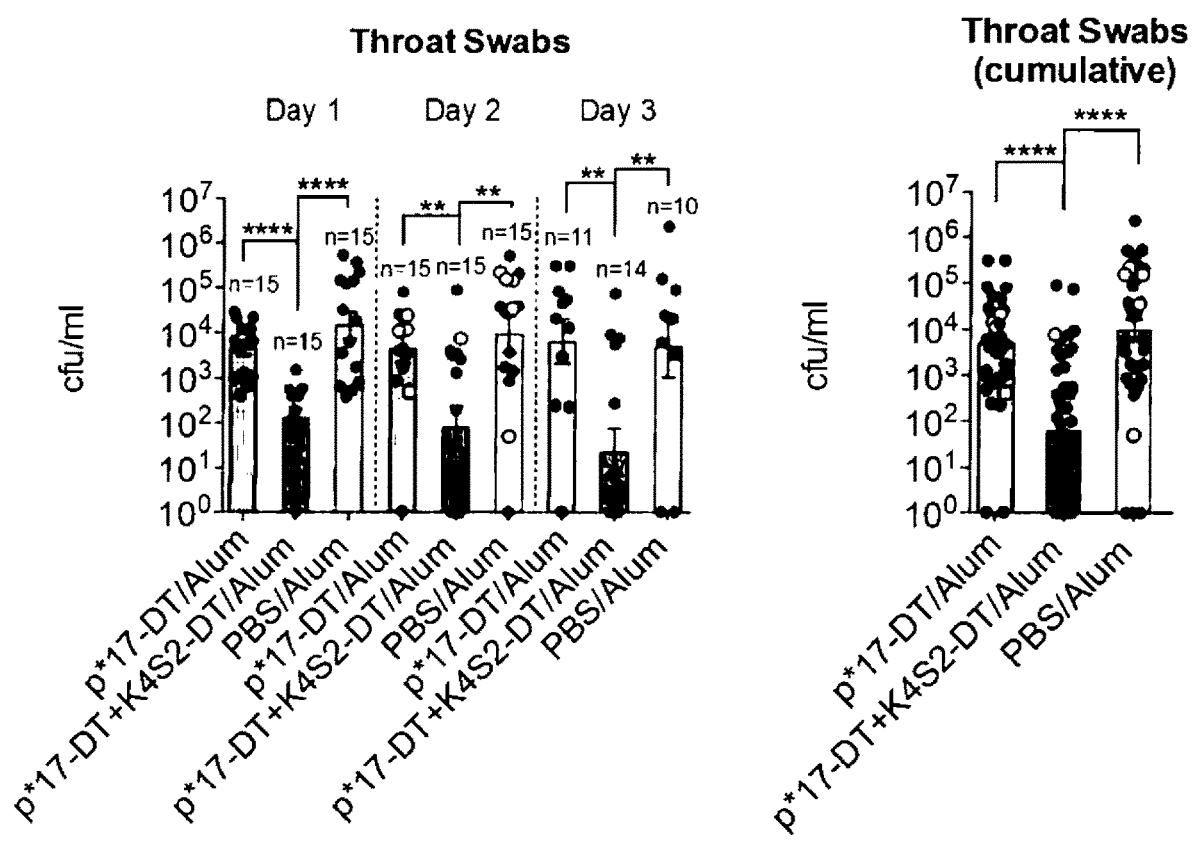

FIG. 13: Protection following intranasal infection. In addition to NS on days 1-3 throat swabs (TS) were collected. For throat swabs, swab applicators were placed in sterile PBS to dampen, mice were then immobilized and throats were swabbed. Swab applicator was then suspended in PBS, serially diluted and dot-plated in duplicate on CBA plates containing 5% defibrinated horse-blood. On days 1-3 NS were collected and represented as the log transformed mean cfu/ml±SEM from each individual day (A) and as cumulative CFUs from all three days combined (B). o indicates mice culled on day 2 after 15% or more weight loss.

Figure 14:
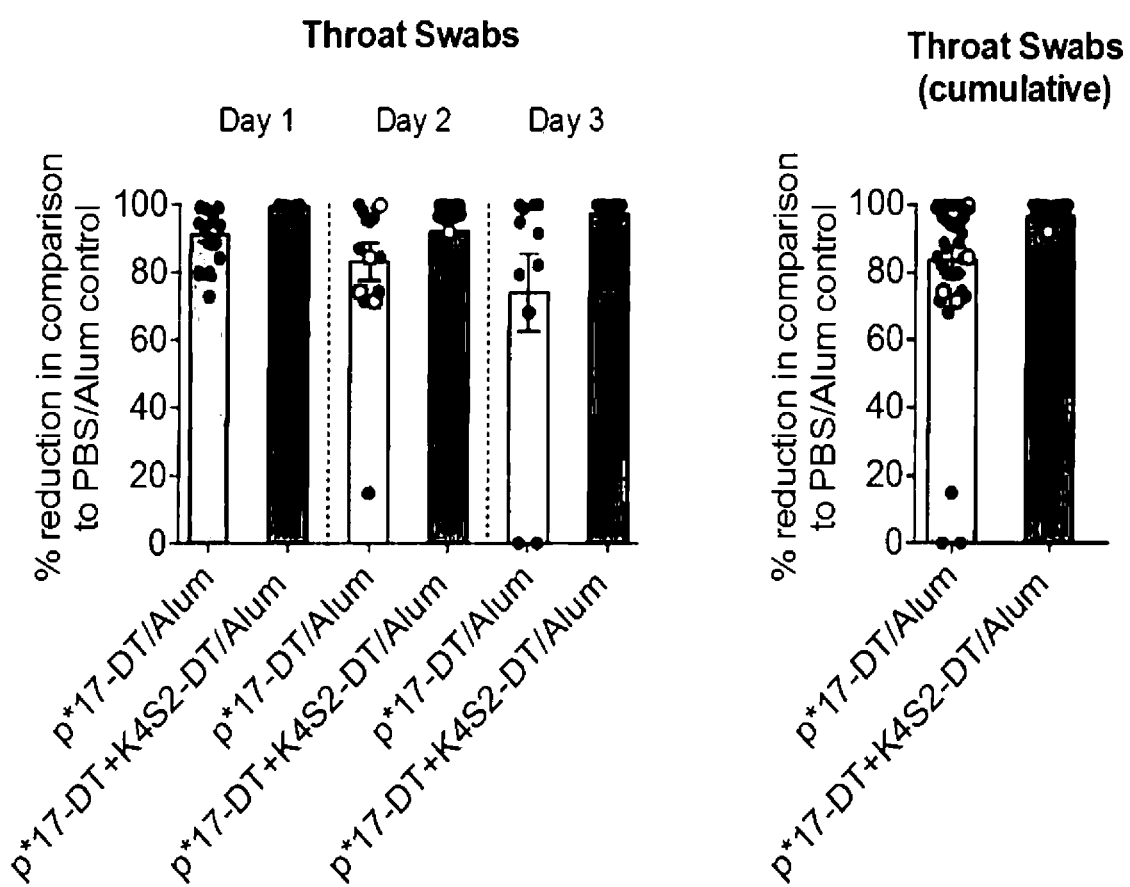

FIG. 14: Percent reduction in bacterial burden in throat swabs. Percent reduction was calculated in comparison to total mean of the PBS/Alum control from each individual day (A) and as cumulative reduction from all three days combined (B). o indicates mice culled on day 2 after 15% or more weight loss.

Figure 15:
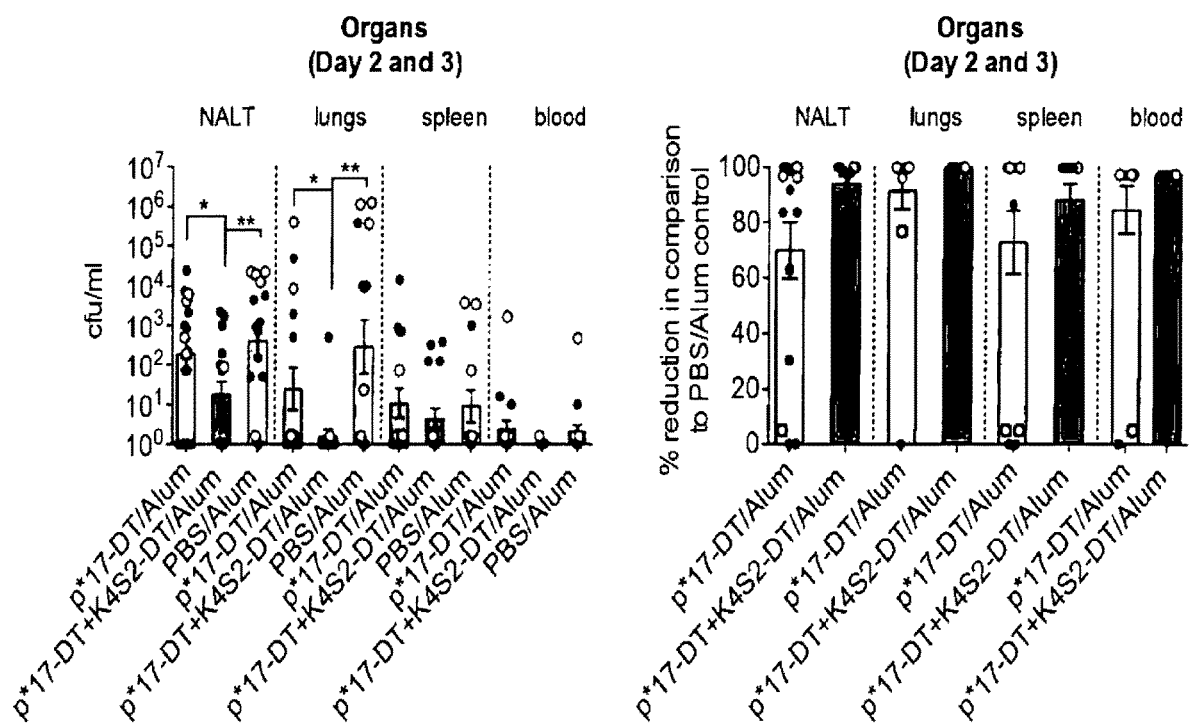

FIG. 15: Protection following intranasal infection. On day 3 post-infection all surviving mice were euthanised and NALT, lungs, spleen and blood samples were collected to determine GAS bacterial burden, data represented as the log transformed mean cfu/ml±SEM (A) and as percent reduction in comparison to PBS/Alum control (B). o indicates mice culled on day 2 after 15% or more weight loss.

Figure 16A:
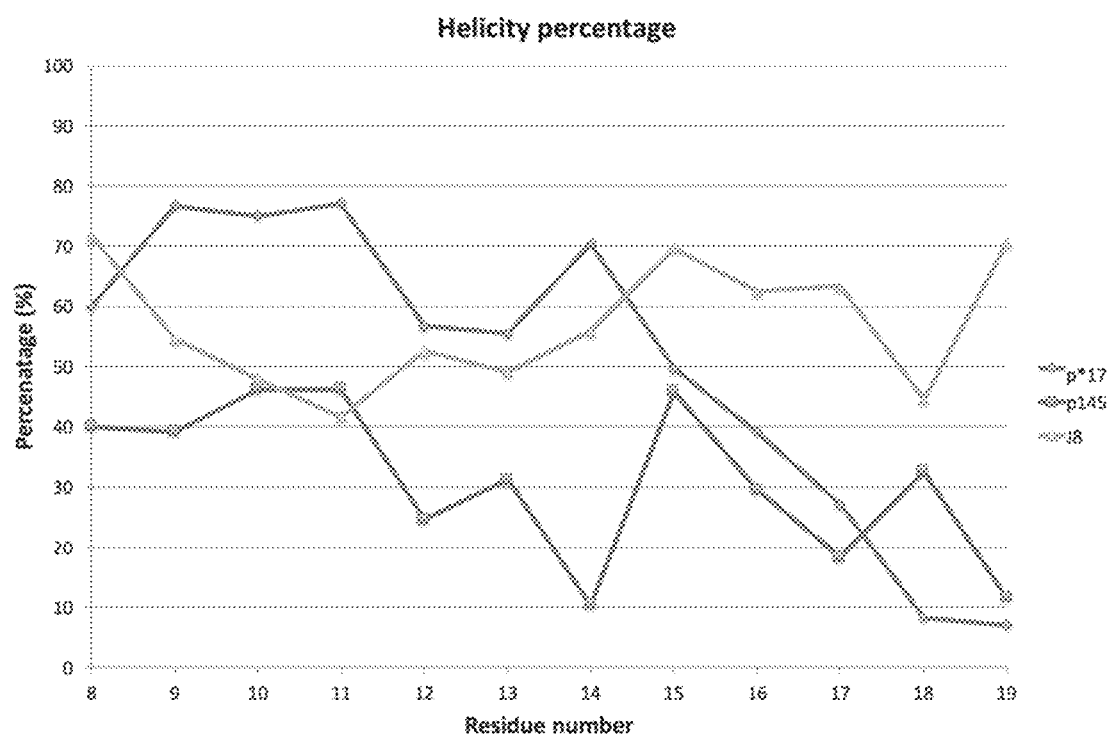
Figure 16B:
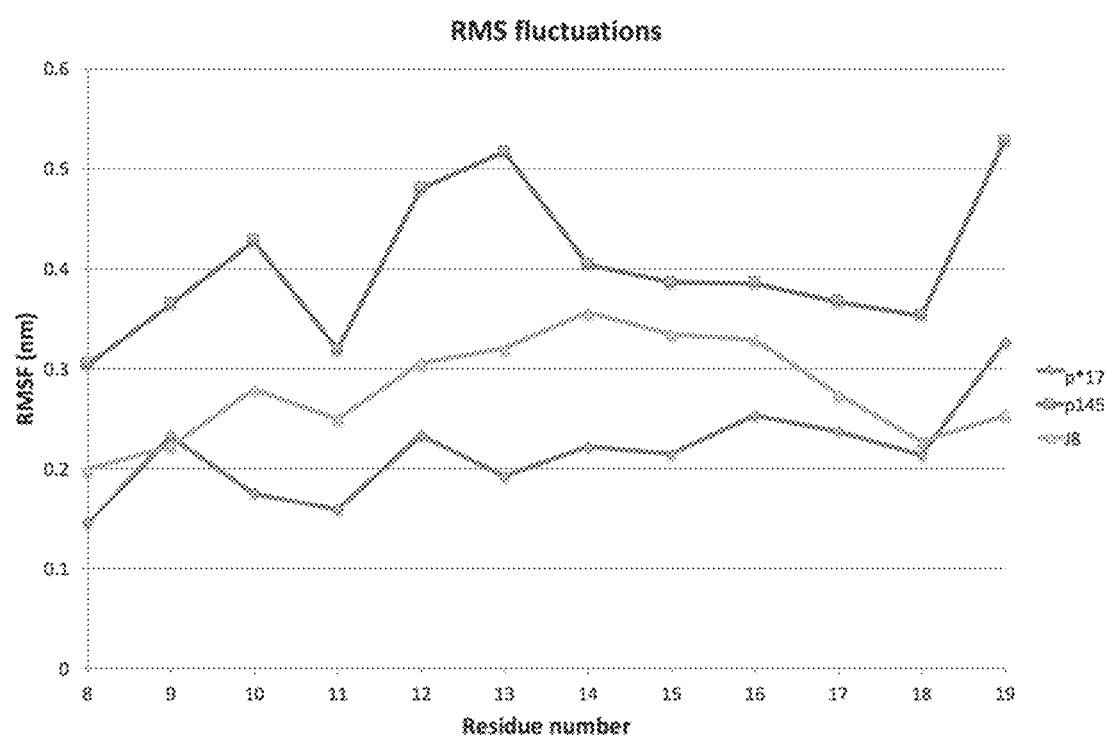

FIG. 16: Structural comparisons of J8 peptide, p145 and p*17. MD simulations comparing the structure of p*17 and J8 peptide in terms of (A) helicity percentage and (B) RMS fluctuation.

ID NO:1, referred to herein as a "p*17 peptide" for inducing or eliciting immunity to group A streptococcal bacterial infection. Preferably, the isolated peptide induces mucosal immunity to group A streptococcal bacterial infection.

| BRIEF DESCRIPTION OF THE SEQUENCES | |
|---|---|
| SEQ ID NO: 1 | LRRDLDASREAKNQVERALE |
| SEQ ID NO: 2 | SREAKNQVERAL |
| SEQ ID NO: 3 | LRRDLDASREAKKQVEKALE |
| SEQ ID NO: 4 | SREAKKQVEKAL |
| SEQ ID NO: 5 | LRRDLDAENEAKKQVEKALE |
| SEQ ID NO: 6 | LRRDLDAEDEAKKQVEKALE |
| SEQ ID NO: 7 | LRRDLDAEREAKNQVEKALE |
| SEQ ID NO: 8 | LRRDLDAEREAKKQVERALE |
| SEQ ID NO: 9 | LRRDLDAEREAKKQVEMALE |
| SEQ ID NO: 10 | LRRDLDAVNEAKKQVEKALE |
| SEQ ID NO: 11 | LRRDLDAVDEAKKQVEKALE |
| SEQ ID NO: 12 | LRRDLDAVREAKNQVEKALE |
| SEQ ID NO: 13 | LRRDLDAVREAKKQVERALE |
| SEQ ID NO: 14 | LRRDLDAVREAKKQVEMALE |
| SEQ ID NO: 15 | LRRDLDASNEAKNQVEKALE |
| SEQ ID NO: 16 | LRRDLDASNEAKKQVERALE |
| SEQ ID NO: 17 | LRRDLDASNEAKKQVEMALE |
| SEQ ID NO: 18 | LRRDLDASDEAKNQVEKALE |
| SEQ ID NO: 19 | LRRDLDASDEAKKQVERALE |
| SEQ ID NO: 20 | LRRDLDASDEAKKQVEMALE |
| SEQ ID NO: 21 | LRRDLDASREAKNQVEMALE |
| SEQ ID NO: 22 | LRRDLDA |
| SEQ ID NO: 23 | NSDNIKENQFEDFDEDWENF |
| SEQ ID NO: 24 | KKKKNSDNIKENQFEDFDEDWENF |
| SEQ ID NOS: 25-111 | Table 3 peptide library in descending numerical order from peptide 1 to peptide 87, respectively. |
| SEQ ID NO: 112: | SGSGLRRDLDASREAKKQVEKALE |

DETAILED DESCRIPTION

The present invention is at least partly predicated on the discovery that particular amino acids of the p145 peptide may be modified to substantially improve immunogenicity against group A streptococci. A single immunization with the modified p145 peptide, rather than multiple immunizations, van protect against group A *streptococcus* infection even by hypervirulent strains such as the CovR/S mutant strain. More specifically, the modified p145 peptide can induce mucosal immunity, characterized by production of IgG rather than IgA. Mucosal immunity may be elicited after intramuscular administration of the peptide.

A broad aspect of the invention is directed to use of an isolated peptide comprising the amino acid sequence of SEQ In some embodiments, the p*17 peptide may be administered in combination with a fragment of a SpyCEP protein. The SpyCEP fragment may be an "S2" peptide, such as comprising the amino acid sequence of SEQ ID NO:23, or a variant comprising an amino acid sequence such as set forth in SEQ ID NO:24, as will be described in more detail hereinafter.

As used herein the terms "group A *streptococcus*", "Group A Streptococci", "Group A Streptococcal", "Group A Strep" and the abbreviation "GAS" refer to streptococcal bacteria of Lancefield serogroup A which are gram positive β-hemolytic bacteria of the species *Streptococcus pyogenes*. An important virulence factor of GAS is M protein, which is strongly anti-phagocytic and binds to serum factor H, destroying C3-convertase and preventing opsonization by C3b. These also include virulent "mutants" such as CovR/S or CovRS mutants such as described in Graham et al., 2002, PNAS USA 99 13855, although without limitation thereto.

Diseases and conditions caused by group A streptococci include cellulitis, erysipelas, impetigo, scarlet fever, throat infections such as acute pharyngitis ("strep throat"), bacteremia, toxic shock syndrome, necrotizing fasciitis, acute rheumatic fever and acute glomerulonephritis, although without limitation thereto.

For the purposes of this invention, by "isolated" is meant material that has been removed from its natural state or otherwise been subjected to human manipulation. Isolated material may be substantially or essentially free from components that normally accompany it in its natural state, or may be manipulated so as to be in an artificial state together with components that normally accompany it in its natural state. Isolated material may be in native, chemical synthetic or recombinant form.

By "protein" is meant an amino acid polymer. The amino acids may be natural or non-natural amino acids, D- or L-amino acids as are well understood in the art.

The term "protein" includes and encompasses "peptide", which is typically used to describe a protein having no more than fifty (50) amino acids and "polypeptide", which is typically used to describe a protein having more than fifty (50) amino acids.

The inventors have shown that modification of a "wild-type" or "unmodified" p145 peptide amino acid sequence substantially improves or enhances the immunogenicity of the peptide. Typically, modification includes substitution of one or more amino acids of a p145 peptide.

This obviates the need to add a heterologous GCN4 amino acid sequence to the p145 peptide to maintain a desired alpha-helical structure of the peptide. Although not wishing to be bound by theory, molecular dynamic simulation shows that a modified p145 peptide disclosed herein does not have a "kink" in its structure, as opposed to wild-type or unmodified p145, which may be at least partly responsible for its improved immunogenicity.

Suitably, a "wild-type" or unmodified p145 peptide comprises the amino acid sequence LRRDLDASREAKKQVEKALE (SEQ ID NO:3). A minimal P145 epitope sequence is SREAKKQVEKAL (SEQ ID NO:4).

Preferably, a modified p145 peptide comprises an N residue corresponding to residue 13 of SEQ ID NO:3 and an R amino acid at residue 17 of SEQ ID NO:3.

Preferably, a modified p145 minimal epitope comprises an N residue corresponding to residue 6 of SEQ ID NO:1 and an R amino acid at residue 10 of SEQ ID NO:1.

In one embodiment, a p*17 peptide comprises the amino acid sequence LRRDLDASREAKNQVERALE (SEQ ID NO:1).

In one embodiment, a modified minimal epitope of p*17 comprises the amino acid sequence SREAKNQVERAL (SEQ ID NO:2).

The invention also provides a fragment of a modified p145 peptide disclosed herein.

A "fragment" is a segment, domain, portion or region of a protein or peptide (such as SEQ ID NO:1, SEQ ID NO:2, SpyCEP, SEQ ID NO: 23 or SEQ ID NO:24) which constitutes less than 100% of the amino acid sequence of the protein. It will be appreciated that the fragment may be a single fragment or may be repeated alone or with other fragments.

In general, fragments may comprise, consist essentially of or consist of up to 5, 6, 7, 8, 9, 10, 11, 12, 13, 14, 15, 16, 17, 18 or 19 contiguous amino acids (such as of SEQ ID NO:1, SEQ ID NO:2, SpyCEP, SEQ ID NO:23 or SEQ ID NO: 24). In one embodiment, the fragment comprises an N residue corresponding to residue 13 of SEQ ID NO:1 and an R amino acid at residue 17 of SEQ ID NO:1. A non-limiting example of a fragment comprises the amino acid sequence SREAKNQVERAL (SEQ ID NO:2).

Suitably, the fragment is an immunogenic fragment. In the context of the present invention, the term "immunogenic" as used herein indicates the ability or potential to generate or elicit an immune response, such as to Group A strep or molecular components thereof, such as M protein or an M protein epitope corresponding to p145, upon administration of the immunogenic fragment to a mammal. Preferably, the immune response elicited by the immunogenic fragment is a mucosal immune response.

By "elicit an immune response" is meant generate or stimulate the production or activity of one or more elements of the immune system inclusive of the cellular immune system, antibodies and/or the native immune system. Suitably, the one or more elements of the immune system include B lymphocytes, antibodies and neutrophils. Preferably, the immune response is a mucosal immune response. Typically, mucosal immune responses are characterized by the production of IgA, with minimal production of other antibody isotypes such as IgG. Surprisingly, the mucosal immune response elicited by the p*17 peptide disclosed herein is characterized by the production of IgG. IgA production is relatively reduced compared to IgG production, or is substantially absent.

As used herein, a protein "variant" shares a definable nucleotide or amino acid sequence relationship with a reference amino acid sequence. The reference amino acid sequence may be the amino acid sequence of SEQ ID NO:1 or SEQ ID NO:2 or SEQ ID NO:23, for example. The "variant" protein may have one or a plurality of amino acids of the reference amino acid sequence deleted or substituted by different amino acids. It is well understood in the art that some amino acids may be substituted or deleted without changing the activity of the immunogenic fragment and/or protein (conservative substitutions). Preferably, protein variants share at least 70% or 75%, preferably at least 80% or 85% or more preferably at least 90%, 91%, 92%, 93%, 94%, 95%, 96%, 97%, 98% or 99% sequence identity with a reference amino acid sequence.

In particular embodiments, the variant may comprise: an N residue corresponding to residue 13 of SEQ ID NO:1 and an R amino acid corresponding to residue 17 of SEQ ID NO:1; or an N residue corresponding to residue 6 of SEQ ID NO:2 and an R amino acid corresponding to residue 10 of SEQ ID NO:2. Accordingly, one or more of the other residues of SEQ ID NO:1 or SEQ ID NO: 2 may be conservatively modified (e.g by amino acid substitution or deletion) so that the variant substantially retains the immunogenicity of SEQ ID NO:1 or SEQ ID NO:2. In this regard, reference is made to Table 2 and the Examples which describe modifications of amino acids other than residues 13 and 17 of SEQ ID NO:1 and their effects upon immunogenicity.

In one particular embodiment, a variant protein or peptide may comprise one or a plurality of lysine residues at an N and/or C-terminus thereof. The plurality of lysine residues (e.g polylysine) may be a linear sequence of lysine residues or may be branched chain sequences of lysine residues. These additional lysine residues may facilitate increased peptide solubility. A non-limiting example of such a variant is designated "K452" (SEQ ID NO:24).

Terms used generally herein to describe sequence relationships between respective proteins and nucleic acids include "comparison window", "sequence identity", "percentage of sequence identity" and "substantial identity". Because respective nucleic acids/proteins may each comprise (1) only one or more portions of a complete nucleic acid/protein sequence that are shared by the nucleic acids/proteins, and (2) one or more portions which are divergent between the nucleic acids/proteins, sequence comparisons are typically performed by comparing sequences over a "comparison window" to identify and compare local regions of sequence similarity. A "comparison window" refers to a conceptual segment of typically 6, 9 or 12 contiguous residues that is compared to a reference sequence. The comparison window may comprise additions or deletions (i.e., gaps) of about 20% or less as compared to the reference sequence for optimal alignment of the respective sequences. Optimal alignment of sequences for aligning a comparison window may be conducted by computerised implementations of algorithms (Geneworks program by Intelligenetics; GAP, BESTFIT, FASTA, and TFASTA in the Wisconsin Genetics Software Package Release 7.0, Genetics Computer Group, 575 Science Drive Madison, Wis., USA, incorporated herein by reference) or by inspection and the best alignment (i.e. resulting in the highest percentage homology over the comparison window) generated by any of the various methods selected. Reference also may be made to the BLAST family of programs as for example disclosed by Altschul et al., 1997, Nucl. Acids Res. 25 3389, which is incorporated herein by reference. A detailed discussion of sequence analysis can be found in Unit 19.3 of CURRENT PROTOCOLS IN MOLECULAR BIOLOGY Eds. Ausubel et al. (John Wiley & Sons Inc NY, 1995-1999).

The term "sequence identity" is used herein in its broadest sense to include the number of exact nucleotide or amino acid matches having regard to an appropriate alignment using a standard algorithm, having regard to the extent that sequences are identical over a window of comparison. Thus, a "percentage of sequence identity" is calculated by comparing two optimally aligned sequences over the window of comparison, determining the number of positions at which the identical nucleic acid base (e.g., A, T, C, G, I) occurs in both sequences to yield the number of matched positions, dividing the number of matched positions by the total number of positions in the window of comparison (i.e., the window size), and multiplying the result by 100 to yield the percentage of sequence identity. For example, "sequence identity" may be understood to mean the "match percentage" calculated by the DNASIS computer program (Version 2.5 for windows; available from Hitachi Software engineering Co., Ltd., South San Francisco, Calif., USA).

The invention also provides a derivative of a modified p145 peptide disclosed herein. Suitably, the modified p145 peptide comprises an amino acid sequence set forth in SEQ ID NO:1 or SEQ ID NO:2.

As used herein, "derivatives" are molecules such as proteins, fragments or variants thereof that have been altered, for example by conjugation or complexing with other chemical moieties, by post-translational modification (e.g. phosphorylation, acetylation and the like), modification of glycosylation (e.g. adding, removing or altering glycosylation), lipidation and/or inclusion of additional amino acid sequences as would be understood in the art. In one particular embodiment, an additional amino acid sequence may comprise one or a plurality of lysine residues at an N and/or C-terminus thereof. The plurality of lysine residues (e.g polylysine) may be a linear sequence of lysine residues or may be branched chain sequences of lysine residues. These additional lysine residues may facilitate increased peptide solubility. Another particular derivative is by conjugation of the peptide to diphtheria toxin (DT). This may be facilitated by addition of a C-terminal cysteine residue.

Additional amino acid sequences may include fusion partner amino acid sequences which create a fusion protein. By way of example, fusion partner amino acid sequences may assist in detection and/or purification of the isolated fusion protein. Non-limiting examples include metal-binding (e.g. polyhistidine) fusion partners, maltose binding protein (MBP), Protein A, glutathione S-transferase (GST), fluorescent protein sequences (e.g. GFP), epitope tags such as myc, FLAG and haemagglutinin tags.

Other additional amino acid sequences may be of carrier proteins such as diphtheria toxoid (DT) or a fragment thereof, or a CRM protein fragment such as described in International Publication WO2017/070735.

Other derivatives contemplated by the invention include, but are not limited to, modification to side chains, incorporation of unnatural amino acids and/or their derivatives during peptide, or protein synthesis and the use of cross-linkers and other methods which impose conformational constraints on the immunogenic proteins, fragments and variants of the invention.

In this regard, the skilled person is referred to Chapter 15 of CURRENT PROTOCOLS IN PROTEIN SCIENCE, Eds. Coligan et al. (John Wiley & Sons NY 1995-2008) for more extensive methodology relating to chemical modification of proteins.

The isolated immunogenic proteins, fragments and/or derivatives of the present invention may be produced by any means known in the art, including but not limited to, chemical synthesis, recombinant DNA technology and proteolytic cleavage to produce peptide fragments.

Chemical synthesis is inclusive of solid phase and solution phase synthesis. Such methods are well known in the art, although reference is made to examples of chemical synthesis techniques as provided in Chapter 9 of SYNTHETIC VACCINES Ed. Nicholson (Blackwell Scientific Publications) and Chapter 15 of CURRENT PROTOCOLS IN PROTEIN SCIENCE Eds. Coligan et al., (John Wiley & Sons, Inc. NY USA 1995-2008). In this regard, reference is also made to International Publication WO 99/02550 and International Publication WO 97/45444.

Recombinant proteins may be conveniently prepared by a person skilled in the art using standard protocols as for example described in Sambrook et al., MOLECULAR CLONING. A Laboratory Manual (Cold Spring Harbor Press, 1989), in particular Sections 16 and 17; CURRENT PROTOCOLS IN MOLECULAR BIOLOGY Eds. Ausubel et al., (John Wiley & Sons, Inc. NY USA 1995-2008), in particular Chapters 10 and 16; and CURRENT PROTOCOLS IN PROTEIN SCIENCE Eds. Coligan et al., (John Wiley & Sons, Inc. NY USA 1995-2008), in particular Chapters 1, 5 and 6. Typically, recombinant protein preparation includes expression of a nucleic acid encoding the protein in a suitable host cell.

A further aspect of the invention provides an antibody or antibody fragment that binds, or is raised against, an isolated immunogenic peptide comprising the amino acid sequence set forth in SEQ ID NO:1, or a fragment, variant or derivative thereof.

Suitably, the antibody or antibody fragment specifically binds an isolated immunogenic peptide comprising the amino acid sequence set forth in SEQ ID NO:1 or a fragment comprising the amino acid sequence of SEQ ID NO:2. In some embodiments, the antibody or antibody fragment binds a p145 peptide or minimal epitope sequence such as that set forth in SEQ ID NO:3 or SEQ ID NO:4, with a substantially higher affinity than an antibody raised against the p145 peptide. In this context, by "substantially higher affinity" is meant an affinity at least 2, 3, 4, 5, 6, 7, 8, 9 or 10 fold higher at a particular concentration of p145 peptide.

Antibodies and antibody fragments may be polyclonal or monoclonal, native or recombinant. Antibody fragments include Fc, Fab or F(ab)2 fragments and/or may comprise single chain Fv antibodies (scFvs). Such scFvs may be prepared, for example, in accordance with the methods described respectively in U.S. Pat. No. 5,091,513, European Patent No 239,400 or the article by Winter & Milstein, 1991, Nature 349:293. Antibodies may also include multivalent recombinant antibody fragments, such as diabodies, triabodies and/or tetrabodies, comprising a plurality of scFvs, as well as dimerisation-activated demibodies (e.g. WO/2007/062466). By way of example, such antibodies may be prepared in accordance with the methods described in Holliger et al., 1993 Proc Natl Acad Sci USA 90 6444; or in Kipriyanov, 2009 Methods Mol Biol 562 177. Well-known protocols applicable to antibody production, purification and use may be found, for example, in Chapter 2 of Coligan et al., CURRENT PROTOCOLS IN IMMUNOLOGY (John Wiley & Sons NY, 1991-1994) and Harlow, E. & Lane, D. *Antibodies: A Laboratory Manual*, Cold Spring Harbour, Cold Spring Harbour Laboratory, 1988.

Methods of producing polyclonal antibodies are well known to those skilled in the art. Exemplary protocols which may be used are described for example in Coligan et al., CURRENT PROTOCOLS IN IMMUNOLOGY, supra, and in Harlow & Lane, 1988, supra. In a particular embodiment, anti-SpyCEP polyclonal antibodies may be obtained or purified from human sera from individuals exposed to, or infected by, Group A strep. Alternatively, polyclonal antibodies may be raised against purified or recombinant SpyCEP, or an immunogenic fragment thereof, in production species such as horses and then subsequently purified prior to administration.

Monoclonal antibodies may be produced using the standard method as for example, originally described in an article by Köhler & Milstein, 1975, Nature 256, 495, or by more recent modifications thereof as for example, described in Coligan et al., CURRENT PROTOCOLS IN IMMUNOLOGY, supra by immortalizing spleen or other antibody producing cells derived from a production species which has been inoculated with one or more of the isolated proteins, fragments, variants or derivatives of the invention. In certain embodiments, the monoclonal antibody or fragment thereof may be in recombinant form. This may be particularly advantageous for "humanizing" the monoclonal antibody or fragment if the monoclonal antibody is initially produced by spleen cells of a non-human mammal.

In some embodiments, the antibody or antibody fragment may be administered to a mammal to provide "passive" immunity to group A streptococcal infection.

Certain further aspects and embodiments of the invention relate to administration of one or more nucleic acids encoding an isolated immunogenic peptide comprising the amino acid sequence set forth in SEQ ID NO:1, or a fragment, variant or derivative thereof for:
  (i) eliciting an immune response to group A streptococcal bacteria in a mammal;
  (ii) immunizing a mammal against group A streptococcal bacteria; and/or
  (iii) treating or preventing a group A streptococcal bacterial infection in a mammal.

The term "nucleic acid" as used herein designates single- or double-stranded DNA and RNA. DNA includes genomic DNA and cDNA. RNA includes mRNA, RNA, RNAi, siRNA, cRNA and autocatalytic RNA. Nucleic acids may also be DNA-RNA hybrids. A nucleic acid comprises a nucleotide sequence which typically includes nucleotides that comprise an A, G, C, T or U base. However, nucleotide sequences may include other bases such as modified purines (for example inosine, methylinosine and methyladenosine) and modified pyrimidines (for example thiouridine and methylcytosine).

In a preferred form, the isolated nucleic acid encoding the immunogenic peptide, fragment, variant or derivative thereof is in the form of a genetic construct suitable for administration to a mammal such as a human. In a preferred for, the genetic construct is suitable for DNA vaccination of a mammal such as a human.

Suitably, the genetic construct is in the form of, or comprises genetic components of, a plasmid, bacteriophage, a cosmid, a yeast or bacterial artificial chromosome as are well understood in the art. Genetic constructs may also be suitable for maintenance and propagation of the isolated nucleic acid in bacteria or other host cells, for manipulation by recombinant DNA technology.

For the purposes of protein expression, the genetic construct is an expression construct. Suitably, the expression construct comprises the one or more nucleic acids operably linked to one or more additional sequences in an expression vector. An "expression vector" may be either a self-replicating extra-chromosomal vector such as a plasmid, or a vector that integrates into a host genome.

By "operably linked or connected" is meant that said additional nucleotide sequence(s) is/are positioned relative to the nucleic acid of the invention preferably to initiate, regulate or otherwise control transcription.

Regulatory nucleotide sequences will generally be appropriate for the host cell or tissue where expression is required. Numerous types of appropriate expression vectors and suitable regulatory sequences are known in the art for a variety of host cells.

Typically, said one or more regulatory nucleotide sequences may include, but are not limited to, promoter sequences, leader or signal sequences, ribosomal binding sites, transcriptional start and termination sequences, translational start and termination sequences, and enhancer or activator sequences. Constitutive or inducible promoters as known in the art are contemplated by the invention. The expression construct may also include an additional nucleotide sequence encoding a fusion partner (typically provided by the expression vector) so that the recombinant protein of the invention is expressed as a fusion protein, as hereinbefore described.

Suitably, DNA vaccination is by way of one or more plasmid DNA expression constructs. Plasmids typically comprise a viral promoter (such as SV40, RSV or CMV promoters). Intron A may be included to improve mRNA stability and thereby increase protein expression. Plasmids may further include a multiple cloning site, a strong polyadenylation/transcription termination signal, such as bovine growth hormone or rabbit beta-globulin polyadenylation sequences. The plasmid may further comprise Mason-Pfizer monkey virus cis-acting transcriptional elements (MPV-CTE) with or without HIV rev increased envelope expression. Additional modifications that may improve expression include the insertion of enhancer sequences, synthetic introns, adenovirus tripartite leader (TPL) sequences and/or modifications to polyadenylation and/or transcription termination sequences. A non-limiting example of a DNA vaccine plasmid is pVAC which is commercially available from Invivogen.

A useful reference describing DNA vaccinology is DNA Vaccines, Methods and Protocols, Second Edition (Volume 127 of Methods in Molecular Medicine series, Humana Press, 2006).

As hereinbefore described, the invention provides compositions, vaccines and/or methods of immunizing against, preventing or treating a Group A Strep-associated disease, disorder or condition in a mammal Suitably, the compositions, vaccines and/or methods of immunizing against, preventing or treating a Group A Strep-associated disease, disorder or condition elicit a mucosal immune response upon administration to a mammal. Preferably, the mucosal immune response is characterized by the production of IgG compared to a lower level of, or absent IgA.

As generally used herein the terms "immunize", "vaccinate" and "vaccine" refer to methods and/or compositions that elicit a protective immune response against Group A Strep, whereby subsequent infection by Group A Strep is at least partly prevented or minimized.

As used herein, "treating", "treat" or "treatment" refers to a therapeutic intervention that at least partly ameliorates, eliminates or reduces a symptom or pathological sign of a Group A strep-associated disease, disorder or condition after it has begun to develop. Treatment need not be absolute to be beneficial to the subject. The beneficial effect can be determined using any methods or standards known to the ordinarily skilled artisan.

As used herein, "preventing", "prevent" or "prevention" refers to a course of action initiated prior to infection by, or exposure to, group A strep and/or before the onset of a symptom or pathological sign of a Group A strep-associated disease, disorder or condition, so as to prevent infection and/or reduce the symptom or pathological sign. It is to be understood that such preventing need not be absolute to be beneficial to a subject. A "prophylactic" treatment is a treatment administered to a subject who does not exhibit signs of a group A strep-associated disease, disorder or condition, or exhibits only early signs for the purpose of decreasing the risk of developing a symptom or pathological sign of a Group A strep-associated disease, disorder or condition.

In the context of the present invention, by "group A-strep-associated disease, disorder or condition" is meant any clinical pathology resulting from infection by group A strep and includes cellulitis, erysipelas, impetigo, scarlet fever, throat infections such as acute pharyngitis ("strep throat"), bacteremia, toxic shock syndrome, necrotizing fasciitis, acute rheumatic fever and acute glomerulonephritis, although without limitation thereto.

In certain aspects and embodiments, the p*17 peptide, fragment, variant or derivative, isolated nucleic acids, genetic constructs, antibodies and/or antibody fragments as disclosed herein, may be administered to a mammal separately, or in combination, in the form of a composition.

In a preferred form, the composition comprises an acceptable carrier, diluent or excipient.

By "acceptable carrier, diluent or excipient" is meant a solid or liquid filler, diluent or encapsulating substance that may be safely used in systemic administration. Depending upon the particular route of administration, a variety of carriers, diluent and excipients well known in the art may be used. These may be selected from a group including sugars, starches, cellulose and its derivatives, malt, gelatine, talc, calcium sulfate, vegetable oils, synthetic oils, polyols, alginic acid, phosphate buffered solutions, emulsifiers, isotonic saline and salts such as mineral acid salts including hydrochlorides, bromides and sulfates, organic acids such as acetates, propionates and malonates, water and pyrogen-free water.

A useful reference describing acceptable carriers, diluents and excipients is Remington's Pharmaceutical Sciences (Mack Publishing Co. N.J. USA, 1991) which is incorporated herein by reference.

Preferably, for the purposes of eliciting an immune response, certain immunological agents may be used in combination with the p*17 peptide, fragment, variant or derivative.

The term "immunological agent" includes within its scope carriers, delivery agents, immunostimulants and/or adjuvants as are well known in the art. As will be understood in the art, immunostimulants and adjuvants refer to or include one or more substances that enhance the immunogenicity and/or efficacy of a composition. Non-limiting examples of suitable immunostimulants and adjuvants include squalane and squalene (or other oils of plant or animal origin); block copolymers; detergents such as TWEEN®-80; Quil® A, mineral oils such as DRAKEOL® or MARCOL®, vegetable oils such as peanut oil; *Corynebacterium*-derived adjuvants such as *Corynebacterium parvum; Propionibacterium*-derived adjuvants such as *Propionibacterium* acne; *Mycobacterium bovis* (Bacille Calmette and Guerin or BCG); *Bordetella pertussis* antigens; tetanus toxoid; diphtheria toxoid; surface active substances such as hexadecylamine, octadecylamine, octadecyl amino acid esters, lysolecithin, dimethyldioctadecylammonium bromide, N,N-dicoctadecyl-N', N'bis(2-hydroxyethyl-propanediamine), methoxyhexadecylglycerol, and pluronic polyols; polyamines such as pyran, dextransulfate, poly IC carbopol; peptides such as muramyl dipeptide and derivatives, dimethylglycine, tuftsin; oil emulsions; and mineral gels such as aluminium phosphate, aluminium hydroxide or alum; interleukins such as interleukin 2 and interleukin 12; monokines such as interleukin 1; tumour necrosis factor; interferons such as gamma interferon; immunostimulatory DNA such as CpG DNA, combinations such as saponin-aluminium hydroxide or Quil-A aluminium hydroxide; liposomes (e.g see International Publication WO2017/070735); ISCOM® and ISCOMATRIX® adjuvant; mycobacterial cell wall extract; synthetic glycopeptides such as muramyl dipeptides or other derivatives; Avridine; Lipid A derivatives; dextran sulfate; DEAE-Dextran alone or with aluminium phosphate; carboxypolymethylene such as CARBOPOL® EMA; acrylic copolymer emulsions such as NEOCRYL® A640 (e.g. U.S. Pat. No. 5,047,238); water in oil emulsifiers such as MONTANIDE® ISA 720; poliovirus, vaccinia or animal poxvirus proteins; or mixtures thereof.

Immunological agents may include carriers such as thyroglobulin and diphtheria toxoid (DT); albumins such as human serum albumin; toxins, toxoids or any mutant cross-reactive material (CRM) of the toxin from tetanus, diphtheria, pertussis, *Pseudomonas, E. coli, Staphylococcus,* and *Streptococcus*; polyamino acids such as poly(lysine:glutamic acid); influenza; Rotavirus VP6, Parvovirus VP1 and VP2; hepatitis B virus core protein; hepatitis B virus recombinant vaccine and the like. Alternatively, a fragment or epitope of a carrier protein or other immunogenic protein may be used. For example, a T cell epitope of a bacterial toxin, toxoid or CRM may be used. In this regard, reference may be made to U.S. Pat. No. 5,785,973 which is incorporated herein by reference. Other immunological agents may include immunogenic peptides from Group A strep proteins other than M protein, for example a SpyCEP peptide as described in International Publication WO2015/157820.

Any suitable procedure is contemplated for producing vaccine compositions. Exemplary procedures include, for example, those described in New Generation Vaccines (1997, Levine et al., Marcel Dekker, Inc. New York, Basel, Hong Kong), which is incorporated herein by reference.

In some embodiments, compositions and vaccines may be administered to mammals in the form of attenuated or inactivated bacteria that may be genetically modified to express the p*17 peptide, fragment, variant or derivative and/or the agent that facilitates restoring or enhancing neutrophil activity. Non-limiting examples of attenuated bacteria include *Salmonella* species, for example *Salmonella enterica* var. *Typhimurium* or *Salmonella typhi*. Alternatively, other enteric pathogens such as *Shigella* species or *E. coli* may be used in attenuated form. Attenuated *Salmonella* strains have been constructed by inactivating genes in the aromatic amino acid biosynthetic pathway (Alderton et al., Avian Diseases 35 435), by introducing mutations into two genes in the aromatic amino acid biosynthetic pathway (such as described in U.S. Pat. No. 5,770,214) or in other genes such as htrA (such as described in U.S. Pat. No. 5,980,907) or in genes encoding outer membrane proteins, such as ompR (such as described in U.S. Pat. No. 5,851,519).

Any safe route of administration may be employed, including oral, rectal, parenteral, sublingual, buccal, intravenous, intra-articular, intra-muscular, intra-dermal, subcutaneous, inhalational, intraocular, intraperitoneal, intracerebroventricular, topical, mucosal and transdermal administration, although without limitation thereto.

In one particular embodiment, administration is intramuscular such as by way of one or more intramuscular injections. Typically, intranasal administration is considered to be optimal for inducing mucosal immunity. Surprisingly, intramuscular administration of p*17 peptide elicits a mucosal immune response to group A streptococcal bacteria.

Dosage forms include tablets, dispersions, suspensions, injections, solutions, syrups, troches, capsules, nasal sprays, suppositories, aerosols, transdermal patches and the like. These dosage forms may also include injecting or implanting controlled releasing devices designed specifically for this purpose or other forms of implants modified to act additionally in this fashion. Controlled release may be effected by coating with hydrophobic polymers including acrylic resins, waxes, higher aliphatic alcohols, polylactic and polyglycolic acids and certain cellulose derivatives such as hydroxypropylmethyl cellulose. In addition, the controlled release may be effected by using other polymer matrices, liposomes and/or microspheres.

Compositions may be presented as discrete units such as capsules, sachets, functional foods/feeds or tablets each containing a pre-determined amount of one or more therapeutic agents of the invention, as a powder or granules or as a solution or a suspension in an aqueous liquid, a non-aqueous liquid, an oil-in-water emulsion or a water-in-oil liquid emulsion. Such compositions may be prepared by any of the methods of pharmacy but all methods include the step of bringing into association one or more agents as described above with the carrier which constitutes one or more necessary ingredients. In general, the compositions are prepared by uniformly and intimately admixing the agents of the invention with liquid carriers or finely divided solid carriers or both, and then, if necessary, shaping the product into the desired presentation.

The above compositions may be administered in a manner compatible with the dosage formulation, and in such amount as effective. The dose administered to a patient, in the context of the present invention, should be sufficient to effect a beneficial response in a patient over an appropriate period of time. The quantity of agent(s) to be administered may depend on the subject to be treated inclusive of the age, sex, weight and general health condition thereof, factors that will depend on the judgement of the practitioner.

In a particular embodiment of the aforementioned methods and compositions, the modified p145 peptide, fragment or variant may be administered in combination with an immunogenic fragment of a SpyCEP protein. It will be appreciated that the SpyCEP protein fragment may act as an agent that facilitates restores or enhances neutrophil activity, by directly or indirectly at least partly increasing enhancing or restoring the production, migration and/or chemotaxis of neutrophils and/or one or more immunological activities of neutrophils. Typically, the SpyCEP fragment elicits an inhibitory immune response to the SpyCEP serine protease that proteolytically cleaves interleukin 8. SpyCEP is a 170-kDa multidomain serine protease expressed on the surface of the human pathogen *Streptococcus pyogenes*, which plays an important role in infection by catalyzing cleavage and inactivation of the neutrophil chemoattractant interleukin-8. Non-limiting examples of SpyCEP amino acid sequences may be found under accession numbers YP597949.1 and (*S. pyogenes* MGAS10270) and YP596076.1 (*S. pyogenes* MGAS9429). Preferably, the fragment of SpyCEP is, or comprises an S2 peptide (SEQ ID NO:23) or a variant such as a K4S2 peptide (SEQ ID NO:24).

In some embodiments, the modified p145 peptide, fragment or variant and the S2 peptide, fragment or variant may be provided as a single, chimeric peptide. In this embodiment, the modified p145 peptide may be N-terminal or C-terminal of the S2 peptide.

As generally used herein, the terms "patient", "individual" and "subject" are used in the context of any mammalian recipient of a treatment or composition disclosed herein. Accordingly, the methods and compositions disclosed herein may have medical and/or veterinary applications. In a preferred form, the mammal is a human.

So that the invention may be fully understood and put into practical effect, reference is made to the following non-limiting Examples.

EXAMPLES

Introduction

The ability to enhance the immunogenicity of small peptide epitopes would greatly facilitate vaccine development. The approaches that have been undertaken so far to improve immunogenicity for antibody production have centred on novel folding technologies that result in the epitope more closely resembling native structure (e.g. (5)) or strategies to incorporate additional molecules with the peptide that will activate antigen presenting cells (e.g. (6, 7)) or helper T cells (8, 9).

Approaches to alter the sequence of the peptide to improve its immunogenicity are also being considered. Heteroclitic peptides have been tested for enhancing immunogenicity for T cells (10). However, nearly all vaccines are reliant on the production of protective antibodies and here modified peptides have been largely ignored, but amino acid modifications outside of a minimal 4-amino acid epitope were shown to be able to improve peptide recognition by a monoclonal antibody suggesting that this approach may be useful for vaccine development (11). Sequence modifications of complex epitopes and modifications within minimal epitopes to improve immunogenicity have not been tested as a mode to enhance efficacy.

A conserved peptide epitope from the M protein of *Streptococcus pyogenes* provides an ideal focus and opportunity to develop a strategy to rationally design and test an enhanced complex peptide immunogen for inducing protective antibodies. The M protein has a conserved carboxyl terminal region and a 20-amino acid peptide, 'p145', which has an alpha helical structure, was described that can induce broad strain-protective antibodies (reviewed in (12)). A minimal B cell epitope of 12 amino acids exists within p145. However, the entire 20 amino acids are required to maintain the helical folding of the minimal epitope. This epitope is cryptic for the organism.

Exposure to *S. pyogenes* does not usually result in the production of antibodies to p145 (13), (14); however, antibodies induced to the minimal epitope by vaccination can kill the organism Immunity requires multiple rounds of vaccination and protection correlates with the magnitude of the immune response (15).

In the present study, iterative rounds of targeted amino acid substitutions within the minimal B cell epitope were performed to create p145 variants. As a result the immunogenicity and ability of the peptide-antisera to bind p145 and streptococci were significantly increased and vaccine efficacy was enhanced such that only a single immunization was 1 required to induce immunity. We observed a 10,000-fold enhanced level of protection from invasive streptococcal disease compared to control mice vaccinated with the parent peptide.

Materials & Methods

Peptides

The peptides were obtained from Mimotopes Pty Ltd (Victoria, Australia).

The peptide library (87 peptides including p145) was purchased as a cleaved PepSet with a biotin coupled to the N5 terminus and a linker of four amino acids (SGSG; SEQ ID NO: 114) was added between the peptide and the biotin. The peptides were biotinylated via the N-terminus to minimize interference with the ligand binding. The p*1-p*18 peptides were obtained as custom peptides with minimal purity of >90%. An additional cysteine residue was added in the N-terminal end to each peptide to enable coupling to Gel Spin columns (see below). The p145 used for coating in ELISA was synthesized at the QIMR Berghofer Medical Research Institute, DNA and Peptide Unit or at China peptides. The p*17 peptide with C-terminal cysteine residue, was synthesized at China peptides and conjugated to DT as described elsewhere (16).

Antisera

Antisera used for peptide screening were from J8-immunised B10.BR, J8-DT-immunised BALB/c, or p145-immunised BALB/c, Quackenbush and B10.D2 mice.

Bacteria

GAS strains, 2031 (emm1) is an isolate from Prague reference center and 8830 (emm97) is a clinical isolate from the Northern Territory of Australia (17). Both strains were obtained from Menzies School of Health Research (MSHR); mouse-adapted for in vivo studies and made streptomycin resistant (200 µg/mL). JRS145 is an M-protein negative mutant.

Enzyme-Linked Immunosorbent Assay (ELISA)

ELISA with biotinylated peptides was performed as recommended by the manufacture (Mimotopes, Australia). Briefly, 100 µl aliquots of streptavidin (Sigma-Aldrich, Australia) at a final concentration of 5 µg/ml in water were added to Oltrack activated 96-well microtiter plates Concentrack, Netherlands) and incubated at 37° C. overnight. The wells were blocked for 1 hr at RT with 200 µl PBS, pH 7.2, containing 0.05% TWEEN® 20 and 1% Sodium caseinate and thereafter washed with PBS/TWEEN® 20. The peptides were diluted in PBS/TWEEN®20 with 0.1% sodium azide to a working concentration of 20 µg/ml and 100 µl of each was added to the wells and incubated for 1 h at RT. After thorough washings, murine p145 or J8 antisera were added. The plates were incubated for 1 h at RT, washed and HRP-conjugated goat anti-mouse-IgG (Bio-Rad, Australia) (1/3000) was added for another 20 min at RT. After additional washings, OPD substrate (Sigma-Aldrich) was added and measured at $OD^{450}$. Titre was defined as the highest dilution that gave an optical density (OD) reading of more than three standard deviations (SD) above the mean OD of control wells containing normal mouse sera at the same dilution (19).

For the inhibition assays, the microtiter plates were coated with 100 µl of purified p145 at a final concentration of 5 µg/ml in 75 mM sodium carbonate, pH 9.6, at 4° C. overnight. Plates were washed with washing buffer (PBS with 0.05% TWEEN® 20, pH 7.2) and blocked for 90 min at 37° C. with washing buffer supplied with 5% skim milk (blocking buffer). Anti-p145 sera were incubated with varying concentrations (0.25 µg/ml-2.5 µg/ml) of selected peptides from the peptide library for 30 min at RT. Test antisera were thereafter added to the blocked plates and incubated for 90 min at 37° C. The plates were washed four times and HRP-conjugated goat anti-mouse IgG (Biorad, Australia) (1/3000) was added and incubated for another 90 min at 37° C. After additional washing, the plates were developed as above and measured at $OD^{450}$.

In the analysis for cross-reactivity with human heart proteins, 5 µg/ml of tropomyosin, myosin or keratin (Sigma-Aldrich, Australia) were immobilised in microtiter plates. After blocking and washings as above, the plates were incubated for 90 min at 37° C. with triplets of anti-peptide (p*1-p*18) sera (1/100), respectively. Thereafter, the secondary antibody and the substrate were added as above.

Immunization of Mice

All protocols were approved by the QIMR Berghofer Medical Research Institute's Animal Ethics Committee, in compliance with Australian National Health and Medical Research (NHMRC) guidelines. On day 0, Quackenbush mice (Animal Resources Centre, Australia) (n=3 per group) were inoculated subcutaneously (s.c.) at the tail base with 30 µg of the different peptides emulsified 1:1 with complete Freund's adjuvant (CFA) in a total volume of 50 µl. Control mice received sterile-filtered PBS in CFA. Three weeks after primary immunization, mice received 2 booster immunizations of immunogen (30 µg each in sterile-filtered PBS) given at weekly intervals (days 21 and 28). Groups of mice with antibody titers of less than 1000 received a third boost emulsified 1:1 with incomplete Freund's adjuvant. Heat-killed GAS 2031 (emm1) was prepared as previously described (18). For the skin challenge studies, BALB/c mice (n=10/group) were immunised s.c. once at the tail base with 30 µg of p145-DT or p*17-DT or heat killed 2031 GAS preparation formulated in Alum. For the p145 dose-ranging study, following primary immunisation with p145-DT/Alum on day 0, specific cohorts were administered 1 or 2 boosts on days 21 and 28. Control mice received adjuvant alone. Blood was collected from each mouse 1-day prior to boosts and one week after the final immunization. The blood was allowed to clot at 4° C. for at least 4 h and serum was collected after centrifugation at 1000 g for 10 minutes. Sera were stored at −20° C.

Affinity Purification of Sera

For purification of the peptide specific sera, Microlink peptide coupling kit (Pierce, USA) was used according to the manufacturer's instructions. Briefly, each peptide was diluted to 0.6 mg/ml in coupling buffer and immobilised to an Ultralink iodoacetyl gel spin column (Pierce, USA). The columns were thoroughly washed with coupling buffer and blocked with L-Cysteine HCl (10 mg/ml). Thereafter, the columns were washed with wash buffer followed by PBS. For affinity purification, 300 µl of the different Quackenbush sera were added to the respective columns and incubated end over end at 4° C. overnight. The columns were washed three times with PBS and antibodies were eluted with 100 µl elution buffer. Thereafter, the columns were washed and blocked again as above and additional sera were added. The eluted immunoglobulin (Ig) concentrations were estimated by using the Nanodrop (Thermo Scientific, USA). The purified IgG preparations at a concentration 5 µg/ml, followed by two-fold serial dilutions, were assessed for their binding to varying concentration of p145.

Flow Cytometry

The binding of the peptide antibodies to the *S. pyogenes* was analysed by flow cytometry. Bacteria were grown in Todd-Hewitt broth (THB) with 1% neopeptone overnight and washed twice in PBS. Thereafter, bacteria (3×10$^7$ colony forming units; cfu) were pre-incubated with 100 µl of Fc blocker for 15 min at RT followed by addition of the peptide antibodies at a concentration of 10 mg/ml. After 30 min incubation at RT, the bacteria were washed twice in PBS followed by incubation with a FITC-conjugated anti-mouse IgG (diluted 1/50 in PBS with 2% BSA), total volume of 100 µl, was added for another 30 minutes at RT. The bacteria were washed and incubated in 300 µl of 1% formaldehyde (in PBS) and for 15 minutes at RT and then transferred to ice until reading in a FACS Calibur Flow Cytometer 1 (Becton Dickinson, USA).

The FITC-conjugated anti-mouse IgG was added separately as a negative control for each strain analysed and in addition, a non-specific mouse IgG was included as a control.

Procedure for GAS Skin Challenge

*S. pyogenes* 2031 (emm1), 88/30 (emm97) and 5448AP (emm1) were cultured overnight in THB with 1% Neopeptone (THBN), washed twice in THBN and resuspended in 25% of the original volume. The inoculum dose (CFU/ml) was determined by optical density at 600 nm and plating out 10-fold dilutions of bacterial suspensions on 2% horse blood THB agar. Following overnight incubation at 37° C., colony counts were determined. Two weeks post final immunization, immunized and control mice were challenged with selected GAS strain via the skin route of infection, as described previously (19).

Molecular Dynamics (MD) Simulations

Molecular dynamics (MD) simulations of peptides p*17 and P145 were performed to examine possible molecular basis of their immunogenicity. Their sequences, with a C-terminal Cysteine attached, were submitted to PEP-FOLD server (20) to construct initial structural models. These models were used as starting points for MD simulations, which were carried out in GROMACS 5 (21). All residues were parameterized with Amber ff14SB force field (22).

Each peptide was placed in a dodecahedral box with a minimal distance of 1.2 nm between the solute and box edge, followed by solvation with TIP3P water molecules (23). Salt ions were then added to a concentration of 0.15 M to balance ionic charge in the system. Energy minimizations were carried out with steepest descent integrator and conjugate gradient algorithm sequentially to achieve a maximum force of less than 500 kJ mol$^{-1}$ nm$^{-1}$ on any atom. The Verlet cutoff scheme (24) was used to evaluate short-range, non-bonded interactions, with both van der Waals and electrostatic interactions truncated at 0.8 nm. Long-range electrostatic interactions were treated by the particle mesh Ewald (PME) method (25, 26). The temperature was maintained at 298 K using a velocity rescaling thermostat (27) with a coupling constant of 0.1 ps, while the pressure was maintained at 1.0 atm using a Berendsen barostat (28), with a coupling constant of 1 ps.

Simulations were performed with a time step of 2 fs, and all bonds involving hydrogen atoms were constrained by a parallel linear constraint solver (P-LINCS) (29). Each system was equilibrated under a constant volume (NVT) ensemble for 100 ps and a constant pressure (NPT) ensemble for 100 ps. A harmonic position restraint with a force constant of 1000 kJ mol$^{-1}$ nm$^{-2}$ was applied to all the heavy atoms of non-solvent molecules. After equilibration, production MD simulations were conducted for 100 ns for each system without any constraints. Three replicate MD runs were performed for each system by varying the random seed for initial velocity generation. Analyses of MD trajectories were performed by inbuilt programs of GROMACS 5 on the final 40 ns of each 100-ns run to allow for equilibrium.

Statistical Analysis.

The mean and standard error was calculated using standard formulae. Mann-Whitney tests were used to compare the antibody titers between two groups. Unless stated otherwise, P values were corrected using the Bonferroni method for multiple comparisons. ANOVA with the Tukey's post hoc method was used to determine the significance between all the treated and control cohorts at each time point.

Results

Our goal was to design a superior peptide immunogen against GAS as compared to p145 using iterative rounds of selection of mutant sequences within the minimal 12 amino-acid epitope within p145 (Table 1). Initially, we designed a mutant peptide library (L1) to ask whether the antigenicity of p145 could be increased with single mutations. We sought to identify mutations that would enhance antigenicity but without creating sequences that would resemble known human proteins.

Figure 1A:
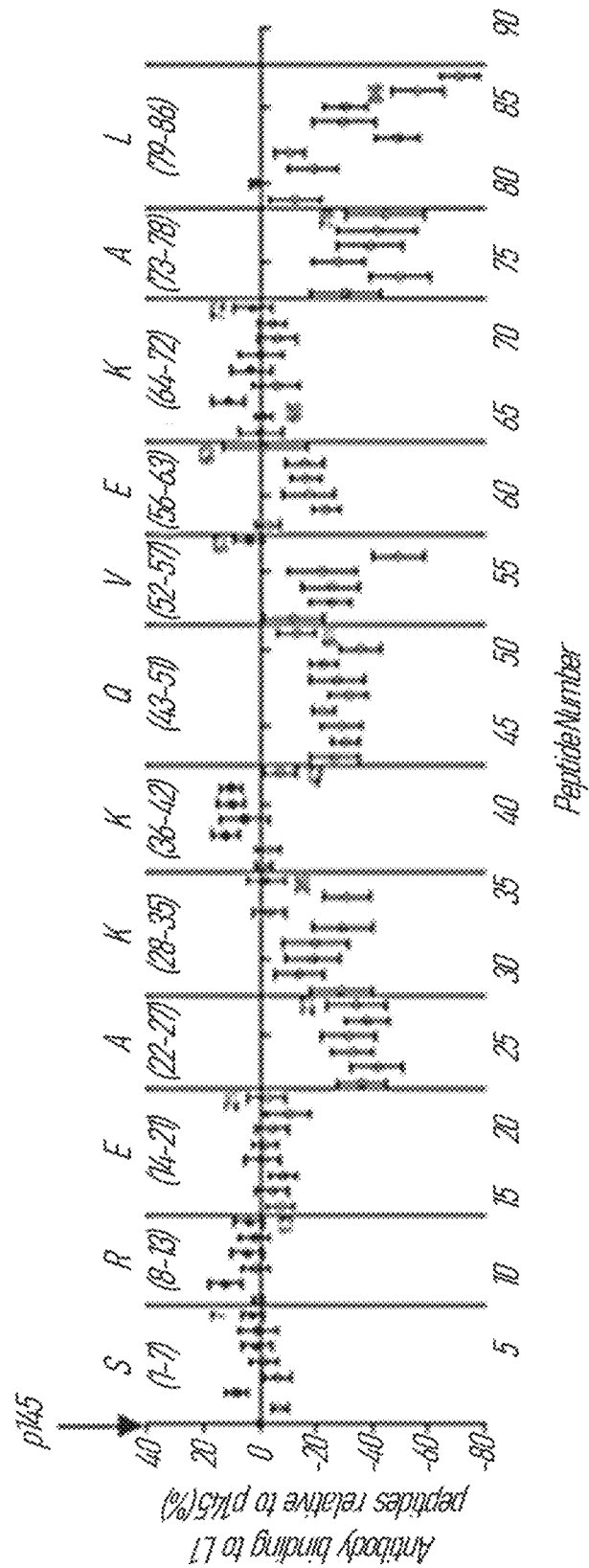
FIG. 1: Designing of peptide libraries: (A) Recognition of various p145 variant peptides by p145 antisera: (A) A peptide library consisting of 86 variants of p145 was screened with p145 antisera. The p145 antiserum was raised in B10.D2 mice and the ability of p145 antiserum to bind each peptide was determined using ELISA. The minimal epitope sequence from within the p145 is at the top of the graph with numbers of peptide sequences undergoing mutation in each amino acid are represented in the parentheses below. The vertical lines separate the peptides based on mutation in the same position. The Peptide 87 is a non-specific control peptide (pNS). (B) Identification of immunodominant peptides within the p145 variants library: Peptide-inhibition ELISAs were performed to identify the immunodominant peptides within the pool of p145 variants. Selected peptides at a concentration of 0.25 µg/ml were incubated with p145 antisera. The serum was then used in an ELISA against immobilised p145. Antigen (p145)-specific serum was collected from hyper-immunised B10.D2 mice. Data for each bar are Means±SEM. (C) Designing of peptide library 2 (L2) with two alterations: The selected 7 peptides were utilised to design a new peptide library with two amino acids substitutions at positions that were identified to enhance immunogenicity of parent p145. The resulting peptides demonstrating mutations at various positions within the p145 minimal epitope are shown. The sequences of peptides 1, 5, 6, 11, 13, 40, 66, and 72 correspond to SEQ ID NOs: 25, 29, 30, 35, 37, 64, 90, and 96 respectively as set forth in Table 3.

In L1, one amino acid was altered at a time and the amino acid substitutions were selected based on their physico-chemical properties relevant to keeping the peptide folded as an alpha helix (5,11 30). The resulting library consisted of 86 variants of p145 plus the original p145 (Table 3). In addition, a non-specific peptide (pNS [#87],) was included as control. The binding of p145 antisera to each peptide was analysed using ELISA. In these studies, to ensure that the same amount of each peptide was bound to the plate, we used biotinylated peptides, which were attached to the plates via streptavidin. A four amino acid peptide linker was placed between the mutant peptide and biotin to ensure sufficient space for antibody recognition. The antisera were obtained from p145-immunized B10.D2, BALB/c and outbred Quackenbush mice. For each of the three different mouse strains, the binding of antisera to the variant peptides ranged from being minimal to being slightly enhanced compared with their binding to p145 (FIG. 1A). Most substitutions resulted in reduced binding. Moreover, similar results were obtained with J8 or J8-DT antisera taken from B10.BR or BALB/c mice respectively (data not shown).

Figure 1B:
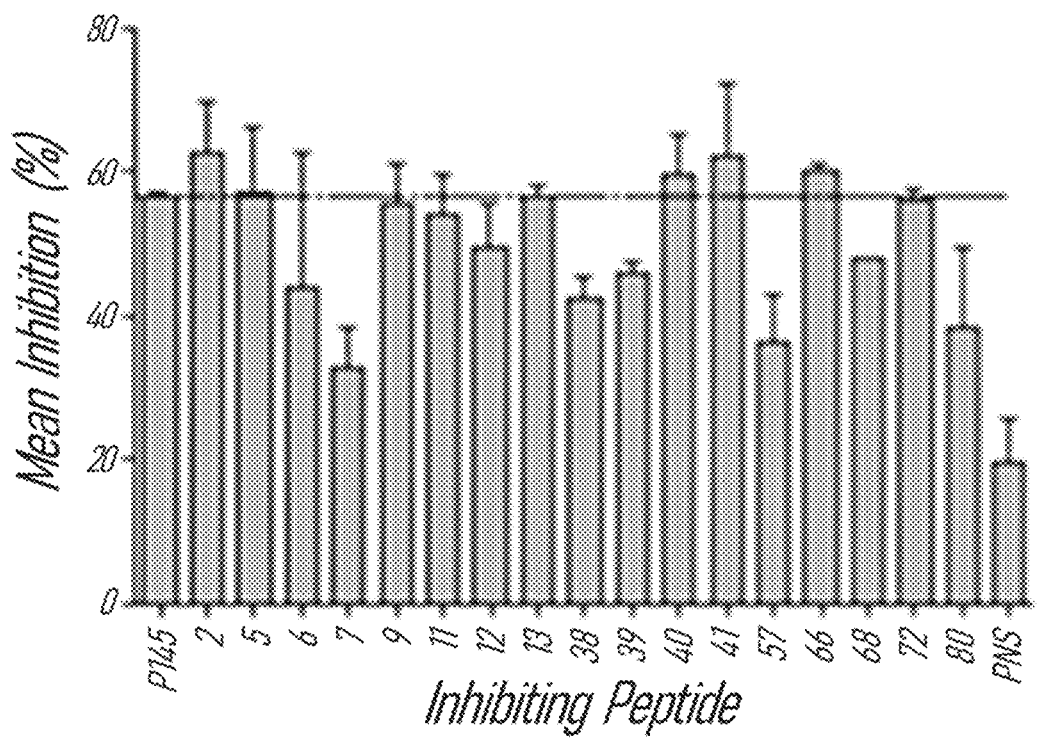

The non-specific peptide was recognized least well of all peptides. We identified 17 peptides to which the p145-specific antisera showed similar or better binding than to p145 and asked whether these peptides in solution could inhibit the binding of p145-specific antiserum to the parent p145 peptide. These peptides when tested in inhibition ELISA, at two different concentrations (0.25 µg/ml and 2.5 µg/ml), demonstrated a dose dependent response (FIG. 1 B and FIG. 6). At both the concentrations, peptides inhibited the binding of anti-p145 antibodies in solution to a comparable extent to p145, probably due to having retained folding similar to p145, however none were clearly superior (FIG. 1B and FIG. 6).

To avoid induction of human specific antibodies, we analysed whether the amino acid substitutions resulted in sequences that were closely related to human proteins using bioinformatics programs (BLASTP and Clustal Omega). Three peptides (2, 9 and 41) were eliminated from further consideration due to similarities (>50% sequence identity) with human proteins including rootletin (Ciliary rootlet coiled-coil protein), Dynactin 1, B-cell receptor associated protein 29, microtubule-actin cross linking factor 1 and myosin (heavy polypeptide 7B, cardiac muscle, beta, Isoform CRA_c). Hence, seven peptides emerged from the primary screen (5, 6, 11, 13, 40, 66, and 72), which involved mutations at four positions: S1E, S1V, R2N, R2D, K6N, K10R and K10M within the p145 minimal epitope (FIG. 1C).

Reasoning that single mutations in those peptides resulted in slightly enhanced recognition by p145-antisera, we then designed a second library, L2, which contained 18 peptides involving every possible combination of two mutations from the seven amino acid mutations identified above. This resulted in peptides designated p*1-18 (Table 2).

Figure 2A:
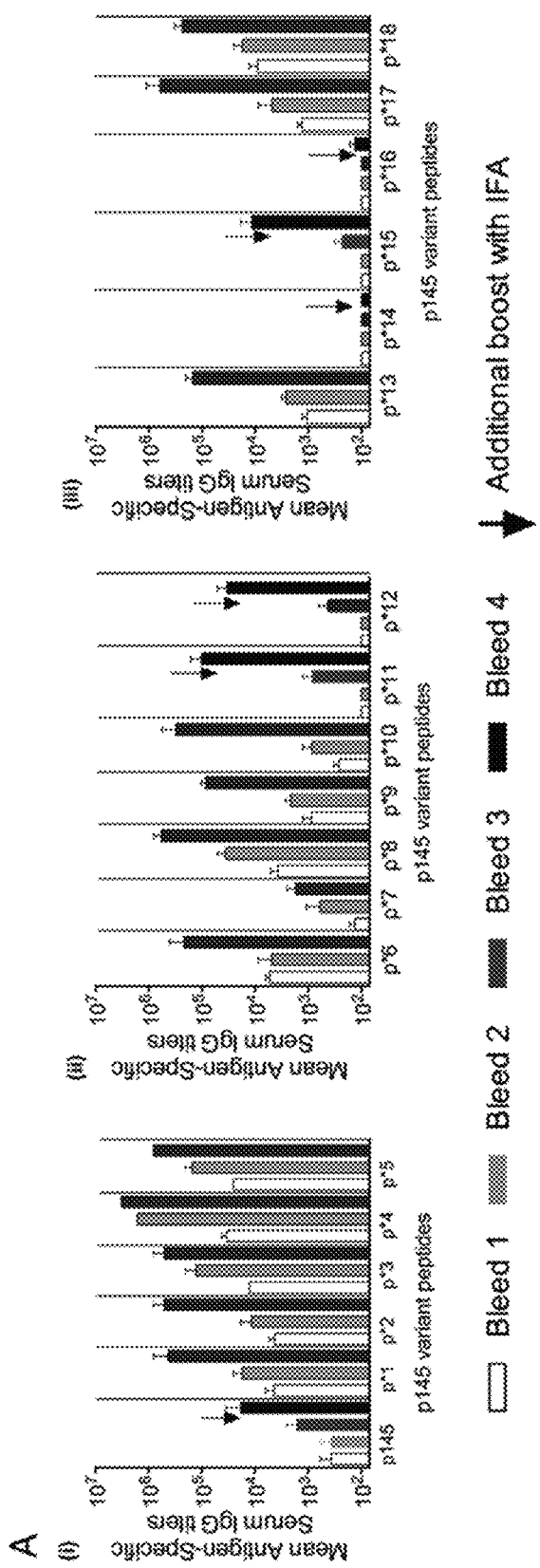
FIG. 2: Immune responses to doubly mutated peptides: (A) Immunogenicity of selected peptides in outbred Quackenbush mice showing ELISA titers to the immunising peptide: Cohorts of mice were subcutaneously immunized with peptide antigen formulated with adjuvant on days 0, 21 and 28. Mice in cohorts with antigen specific titers below 1000 were given an additional boost on day 35 (indicated as "). The mice were bled on days 20, 27, 34 and 41. Control mice received the original p145 or PBS. Antigen-specific serum IgG titers were determined using ELISA and Mean±SEM for peptides 1-5 (1 i), 6-12 (ii) and 13-18 (iii) are shown. (B): Binding of anti-peptide IgG to immobilised p145: The ability of affinity-purified peptide-specific serum IgG to bind increasing concentrations of p145 peptide was determined by ELISA. The peptide p145, immobilised on ELISA plates, was incubated with different peptide specific purified serum IgG from outbred Quackenbush mice. The antibody binding at a concentration of 5 µg/ml are shown for (i) peptides 1-5 and (ii) peptides 6-10 (iii) peptides 11-13 and (iv) peptides 15-18. Mean absorbance (450 nm)±SEM are shown. ANOVA with the Holm-Sidak's multiple comparison tests was used to calculate significance in comparison to p145.

We investigated the immunogenicity of these doubly mutated peptides in outbred (Quackenbush) mice. The immunogenicity of the peptides varied but all except p*14 and p*16 generated antibodies to the immunizing peptide with most giving titers between 1 105 and 106 after three immunizations (FIG. 2A). All peptides, except p*14, p*15 and p*16 were significantly more immunogenic than p145. The most immunogenic peptide was p*17. Antibodies to all peptides, except p*14 and p*16 were then affinity-purified using the immunizing peptide and we ascertained the relative binding of each of the antibodies to titrating concentrations of p145 peptide immobilized on plastic. Each plate was incubated with purified antibodies at 5 µg/ml.

Figure 2B:
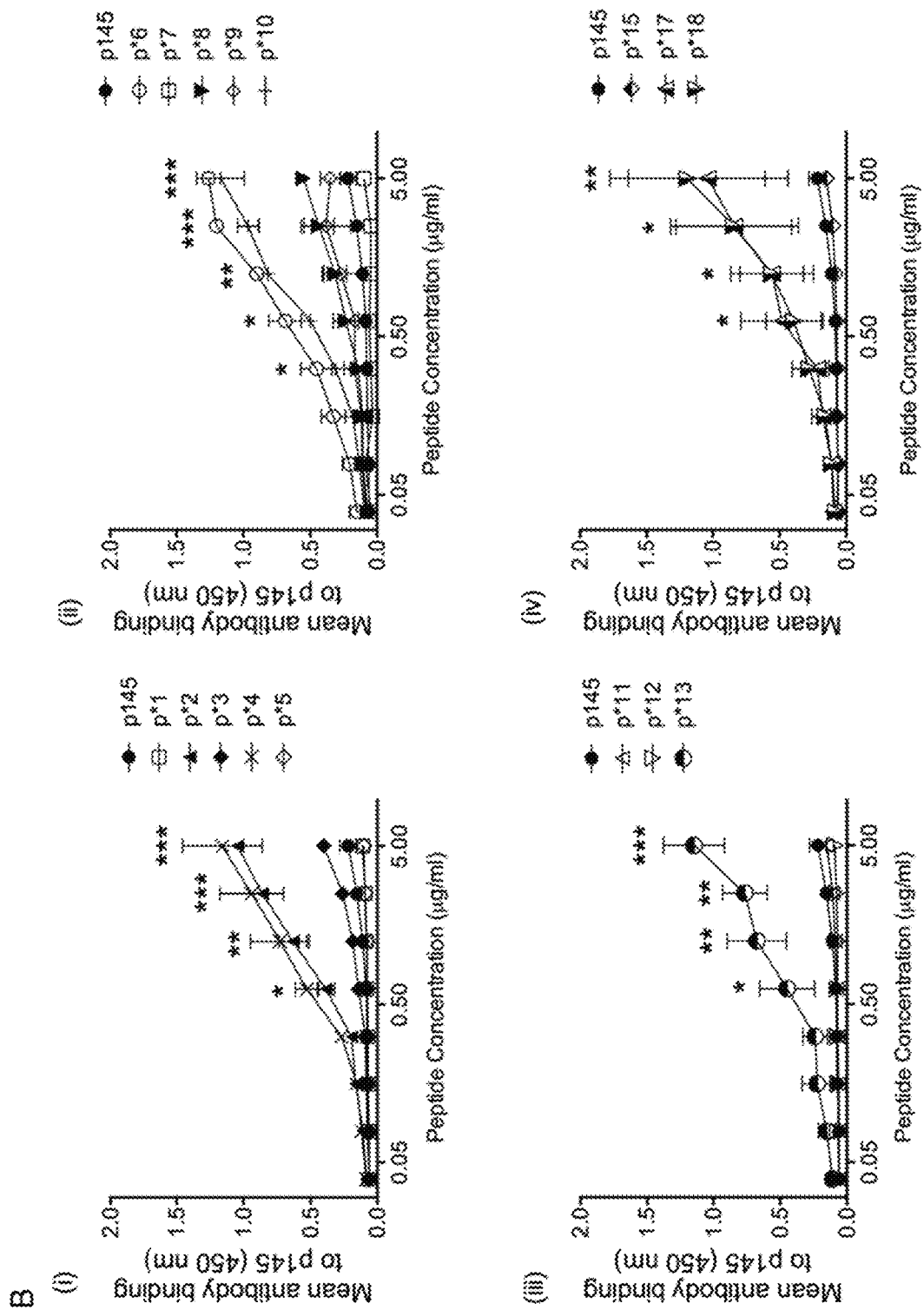

Antibodies induced by seven peptides (p*2, p*4, p*6, p*10, p*13, p*17, and p*18) showed higher affinity, binding significantly more strongly to immobilised p145 than did p145-induced antibodies (FIG. 2B). We noted that five of these seven peptides (p*4, p*10, p*13, p*17 and p*18) carried a K10 mutation. We then used flow cytometry to investigate the binding of affinity purified antibodies, each at the same concentration, to the surface of streptococci expressing different emm proteins—2031 (emm1) and 88/30 (emm97), both containing the exact same p145 sequence.

Figure 3:
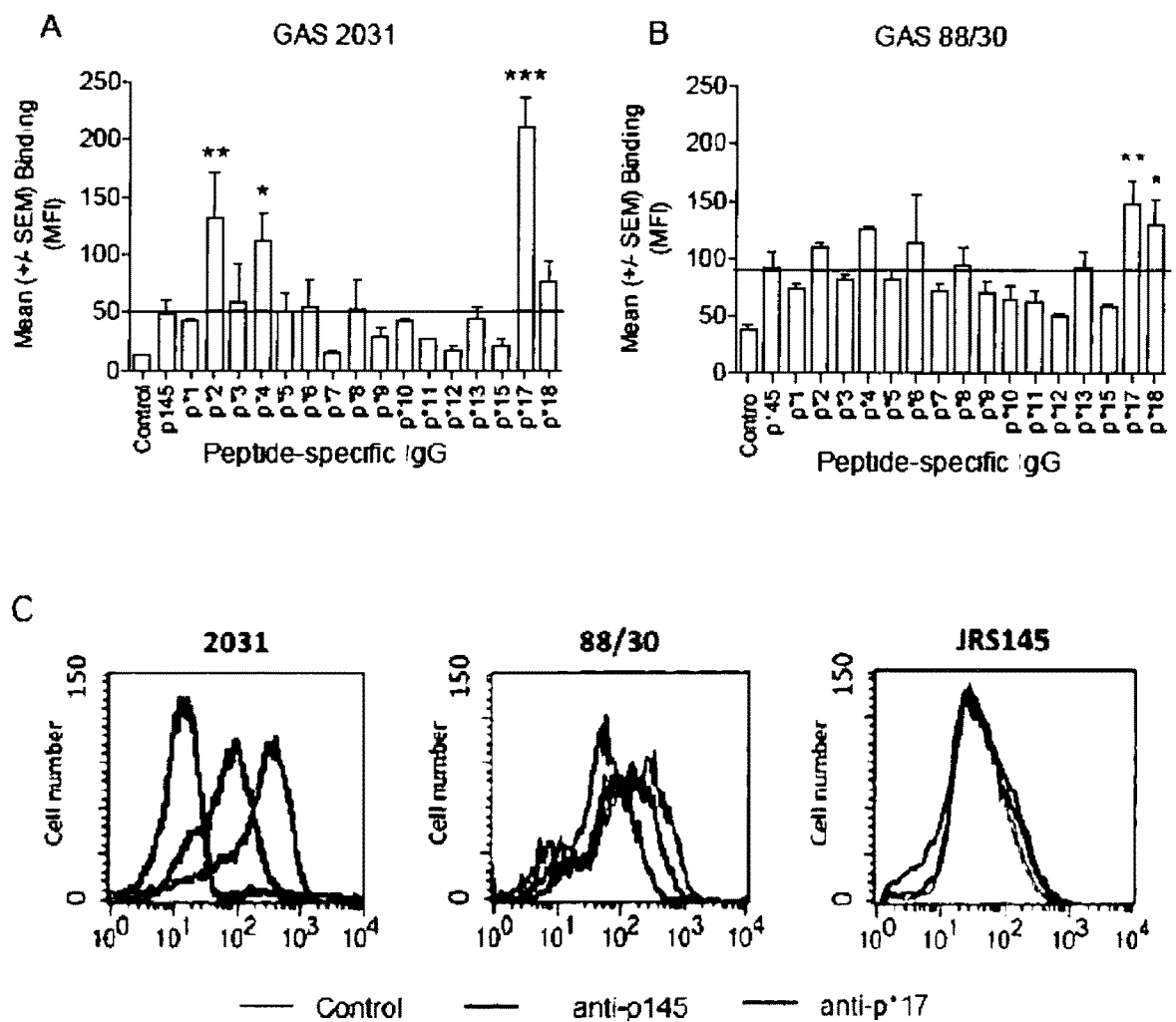
FIG. 3: Binding efficiency of peptide specific antibodies to the surface of GAS: To determine the ability of the peptide-specific serum IgG to bind to whole bacteria, flow cytometry analysis was performed using two GAS strains (A) 2031 (emm1) and (B) 88/30 (emm97). Following incubation with anti-peptide antibodies, FITC conjugated anti-mouse IgG was used to determine the binding of antibodies to GAS. The results are shown as Mean±SEM of mean fluorescence intensity (MFI) for 3 replicates in each group.

Antibodies to p*2, p*4, p*17, and p*18 bound to both GAS strains to a much higher extent as compared to p145-induced antibodies (FIG. 3A-B), with anti-p*17 IgG demonstrating the highest binding. For most peptide antisera there was a correlation between binding to p145 and binding to the bacterial surface, with antisera to p*17 showing the strongest binding to both p145 and streptococci (FIGS. 2B and 3). This antiserum was also tested against an emm-negative strain (JRS145). No binding was observed against this strain (FIG. 3C) confirming that the antibodies were recognizing an epitope within the M protein.

Out of the most effective peptides (p*2, p*4, p*17, and p*18), peptides *2 and *4 were not considered further because antibodies to both these peptides recognised alpha helical coil human proteins (FIG. 7). Thus two peptides, p*17 and p*18 remained for further consideration and we focused on p*17 due to its superior immunogenicity.

Having shown that p*17 was more immunogenic than p145, that antibodies to p*17 demonstrated a higher affinity to p145 than antibodies induced by p145 itself and that they bound different strains of streptococci more strongly than antibodies induced by p145, we asked whether p*17 would be a superior vaccine to p145. p145 conjugated to diphtheria toxoid (p145-DT) can protect against streptococcal skin challenge, but three doses of vaccine are required (Supplementary FIGS. 3A and B). p*17 was thus conjugated to diphtheria toxoid and compared in a head-to-head study with p145-DT, but using only a single dose of vaccine. We used conjugated peptides to provide a similar degree of T-cell help for the anti-peptide responses, enabling us to directly compare the immunogenicities of the peptides for B cells.

BALB/c mice were immunized subcutaneously with p*17-DT, p145-DT or PBS each formulated in Alum. Even though the immunogens were conjugated to DT, we noted that the p145-specific antibody titers induced by p*17-DT were significantly higher than those induced by p145-DT when measured three weeks post-vaccination (FIG. 4A). Mice were then challenged via the skin route with the 2031 (emm1) or 88/30 (emm97) strains of GAS to determine vaccine efficacy. Again, no protection was afforded by vaccination with a single dose of p145-DT against 2031 or 88/30 GAS (FIGS. 4B and D). However, vaccination with p*17-DT resulted in 100-1000 fold reduction in skin bacterial burden six days after challenge as compared to mice vaccinated with p145-DT (FIGS. 4 B and D). Moreover, p*17-DT vaccination resulted in sterile protection from bacteraemia due to 2031 GAS in mice (>10,000-fold reduction in bacterial blood burden compared to mice vaccinated with p145-DT) (FIG. 4C). In addition, the p*17-DT vaccinated cohort completely resolved the systemic infection, due to 88/30, by day 6 post infection, whereas the p145 and PBS immunised cohorts still carried significantly higher bacteremia (FIG. 4E).

Protective ability of p*17-DT was further demonstrated in 1 another study utilising a CovR/S mutant strain. Single vaccination with p*17-DT induced high peptide specific titers (FIG. 8C) and resulted in >90% reduction in skin bacterial burden in comparison to PBS control cohort (FIG. 8D). Moreover, the level of protection was significantly better compared to that offered by heat-killed GAS (FIG. 8D).

Thus, p*17, a non-natural derivative of p145, can induce superior antibodies reactive against p145 in terms of titers and affinity than can p145 itself, and is a significantly superior immunogen to p145 in terms of inducing antibodies that recognize streptococci and protect against them. To ask whether significant structural differences existed between p145 and p*17 that may explain this discrepancy, we used molecular dynamic (MD) simulations to analyse the peptides. The simulations revealed that the helix in p145 breaks between position 12 and 14, probably due to the disruptive effect of the positively charged Ks at positions 12 and 13 (FIG. 5A). p*17 has a non-charged asparagine (N) at position 13 facilitating the folding of the helix. The data also demonstrate that p145 peptide was less likely to adopt a helical structure than p*17 (helicity percentage of <50 vs<80; FIG. 5B) and also showed larger flexibility (RMS fluctuation; FIG. 5 C).

In further experiments according to the schedule in FIG. 9, intramuscular immunization with p*17 alone or together with S2 peptide was investigated. Mice were immunized three (3) times with p*17-DT+K4S2-DT/Alum and intranasal challenge with 5448AP (CovR/S MT strain). FIG. 10 shows immunogenicity following i.m. immunisation with p*17-based vaccines. BALB/c mice (n=15/group; female, 4-6 weeks old) were immunised i.m. with p*17-DT/Alum, p*17-DT+K4S2-DT/Alum and PBS/Alum on days 0, 21 and 42. One week post last boost serum and saliva samples were collected and p*17-specific IgG (A & C) and IgA (B & D) antibody responses were measured by ELISA and are represented as mean±SEM. The titers are in comparison to the control cohort that received only PBS/Alum.

FIG. 11 shows protection following intranasal infection. Two weeks after last vaccine boost, the mice were infected intranasally with covR/S mutant GAS (5448AP). On days 1-3 nasal shedding (NS) were collected. Bacterial burden in NS were determined by pressing the nares of each mouse onto columbia blood agar (CBA) plates containing 5% defibrinated horse-blood and exhaled particles were streaked out. On days 1-3 NS were collected and represented as the log transformed mean±SEM from each individual day (A) and as cumulative CFUs from all three days combined (B). The percent reduction in bacterial burden the nasal shedding is shown in FIG. 12.

FIG. 13 shows protection following intranasal infection. In addition to NS on days 1-3 throat swabs (TS) were collected. For throat swabs, swab applicators were placed in sterile PBS to dampen, mice were then immobilized and throats were swabbed. Swab applicator was then suspended in PBS, serially diluted and dot-plated in duplicate on CBA plates containing 5% defibrinated horse-blood. On days 1-3 NS were collected and represented as the log transformed mean cfu/ml±SEM from each individual day (A) and as cumulative CFUs from all three days combined (B). FIG. 14 shows the reduction in bacterial burden in throat swabs.

FIG. 15 shows protection following intranasal infection. On day 3 post-infection all surviving mice were euthanised and NALT, lungs, spleen and blood samples were collected to determine GAS bacterial burden, data represented as the log transformed mean cfu/ml±SEM (A) and as percent reduction in comparison to PBS/Alum control (B).

We further observed that 3×i.m. immunisations with p*17-DT/Alum protected against intranasal challenge with GAS. There was 70%-90% reduction in bacterial load in nasal sheddings and throat swabs respectively. In addition there was greater than 70% reduction in the systemic bacterial burden. This was despite the fact that these mice did not induce serum or salivary IgA. Interestingly we saw an induction of salivary IgG following i.m. immunisation. For determination of antibody responses we performed semi-quantitative analysis (ELISA) which were defined as the end point titers. In the experiments that utilised intramuscular vaccination with p*17-DT (with or without K4S2), the mucosal IgA responses were undetectable whereas the mucosal IgG responses were at least 10 times higher.

Structural comparisons of J8 peptide, p145 and p*17 were performed that suggest differences between J8 and p*17 peptides that further support the enhanced immunogenicity of p*17. J8 is 28-mer whereas p*17 is a 20-mer peptide. The two peptides share 10 amino acids, which are derived from native peptide p145 (FIG. 16), streptococcal amino acids shown in bold. The MD simulation studies comparing J8 and p*17 demonstrated that both peptides fold as a helix, however, J8 is more flexible in comparison to p*17. We believe that the overall tertiary structure of p*17 renders it more stable, facilitating a better interaction with host molecules. Moreover, the amino acid composition of p*17 (more similar to the strep sequence than J8) likely induces antibodies recognising the native structure of the organism better than J8.

DISCUSSION

Development of peptide vaccines would be enormously facilitated by technologies that increase the immunogenicity of peptides. Very few studies have used selective amino acid substitutions to modify immunogenicity and where tested these have focused on epitope modifications to augment stimulation of CD8+ T cells, where the results have been mixed. Here, we describe a strategy to significantly enhance the immunogenicity of a complex 12-amino acid helical synthetic peptide from *S. pyogenes*. A number of doubly modified peptides demonstrated significantly enhanced immunogenicity in terms of inducing antibodies to the immunizing peptide and to the parent peptide with some antisera also showing enhanced binding to the surface of streptococci. The peptide with the antiserum that bound most strongly to both the parent peptide and the organism (anti-p*17) was tested as a vaccine to prevent streptococcal infection where we observed that a single immunization resulted in significantly enhanced protection from skin and invasive disease (more than 100-fold reduction in the bioburden of skin streptococci and a >10,000-fold reduction to blood bacterial-burden).

We designed p*17 based on our initial observations of antigenicity of a peptide library of 86 peptides with one amino acid change in each peptide. Four amino acids from the 12 amino acids of the minimal helical epitope were relevant to the construction of peptides that were recognized at least as well as the parent sequence. Even though these singly mutated peptides showed minimal improved recognition over the parent peptide, p145, by anti-p145 antisera, new peptides with two mutations were far superior as immunogens than p145. But more surprisingly, the antibodies generated by these doubly mutated peptides recognized p145 with significantly higher affinity than antibodies induced by p145 itself. Furthermore, a number of peptide antisera recognized the surface of streptococci more avidly than antibodies induced by p145 vaccination.

Even more so, the protective efficacy of one such peptide, p*17, shows that this peptide is a superior vaccine candidate. Single immunisation with p*17 induced high levels of self and p145-specific antibodies, which were protective against multiple GAS strains. Additionally, the peptide also protected against a hypervirulent GAS strain that is responsible for invasive infections globally. Currently, the minimal epitope within p145, displayed within a yeast helical peptide and referred to as J8, is a leading vaccine candidate for streptococci (12). This vaccine candidate also requires three doses to induce protection against skin disease (19).

MD simulations revealed that p*17 is more likely to fold as a helix than p145 and has greater stability. The enhanced stability is likely to have made it more immunogenic than p145 and more likely to induce antibodies that recognize the native structure of the organism, where the epitope is held as a helix. The conformational binding of p*17 antibodies to other epitopes along the M protein that are distinct from the p145 sequence could also, in part, account for the enhanced efficacy of p*17. However, it is curious that the anti-p*17 antibodies recognize p145 better than antibodies raised to p145 itself. It is possible that anti-p*17 antibodies can fold p145 into a helix.

We have found that of the seven variant peptides that induced anti-p145 antibodies of both higher titer and higher affinity, four (p*10, p*13, p*17 and p*18) contained mutations at positions and/or of the minimal epitope such that the two positions were not both occupied by charged amino acids. These positions in the minimal epitope correspond to positions f and c in the heptad motif which come together on the hydrophilic side of the helical peptide; this is likely to render these structures more stable. We have not performed MD simulations for the other peptides to confirm this as our focus was on the most immunogenic one that did not share sequence homology with human proteins (p*17).

We also hypothesize that protection at the mucosal surface is due to induction of salivary IgG. IgG at the mucosal surface has been shown to prevent colonisation by agglutination and thereby clearance of bacteria (Roche et. al., Mucosal Immunol, 2015). Furthermore p*17-DT when combined with K4S2-DT was also able to induce salivary IgG and the combination vaccine was able to protect against hypervirulent CovR/S mutant GAS 5448AP significantly better than p*17-DT alone.

The MD simulation studies comparing J8 and p*17 demonstrated that both peptides fold as a helix, however, J8 is more flexible in comparison to p*17. We believe that the overall tertiary structure of p*17 renders it more stable, facilitating a better interaction with host molecules. Moreover, the amino acid composition of p*17 (more similar to the strep sequence than J8) likely induces antibodies recognising the native structure of the organism better than J8.

In conclusion we have defined a strategy to design peptides with significantly enhanced immunogenicity via a mechanism that may relate not to modifications of the interacting residues of the epitope with the immunoglobulin receptor, but with non-specific ionic forces between the epitope and B cell Ig receptor. The generic strategy that we describe could improve the immunogenicity of many complex peptide epitopes.

Throughout this specification, the aim has been to describe the preferred embodiments of the invention without limiting the invention to any one embodiment or specific collection of features. Various changes and modifications may be made to the embodiments described and illustrated herein without departing from the broad spirit and scope of the invention.

All computer programs, algorithms, patent and scientific literature referred to herein is incorporated herein by reference in their entirety.

REFERENCES

1. Davtyan, H., A. Ghochikyan, I. Petrushina, A. Hovakimyan, A. Davtyan, A. Poghosyan, A. M. Marleau, N. Movsesyan, A. Kiyatkin, S. Rasool, A. K. Larsen, P. J. Madsen, K. M. Wegener, D. K. Ditlevsen, D. H. Cribbs, L. O. Pedersen, and M. G. Agadjanyan. 2013 Immunogenicity, efficacy, safety, and mechanism of action of epitope vaccine (Lu AF20513) for Alzheimer's disease: prelude to a clinical trial. *The Journal of neuroscience: the official journal of the Society for Neuroscience* 33: 4923-4934.
2. Chen, A., B. Mann, G. Gao, R. Heath, J. King, J. Maissoneuve, M. Alderson, A. Tate, S. K. Hollingshead, R. K. Tweten, D. E. Briles, E. I. Tuomanen, and J. C. Paton. 2015. Multivalent Pneumococcal Protein Vaccines Comprising Pneumolysoid with Epitopes/Fragments of CbpA and/or PspA Elicit Strong and Broad Protection. *Clinical and vaccine immunology: CVI* 22: 1079-1089.
3. Dale, J. B., T. A. Penfound, B. Tamboura, S. O. Sow, J. P. Nataro, M. Tapia, and K. L. Kotloff. 2013. Potential coverage of a multivalent M protein-based group A streptococcal vaccine. *Vaccine* 31: 1576-1581.
4. Good, M. F., J. Branigan, G. Smith, and R. A. Houghten. 1990. Peptide immunization can elicit malaria protein-specific memory helper but not proliferative T cells. *Peptide research* 3: 110-115.
5. Cooper, J. A., W. Hayman, C. Reed, H. Kagawa, M. F. Good, and A. Saul. 1997. Mapping of conformational B cell epitopes within alpha-helical coiled coil proteins. *Molecular immunology* 34: 433-440.
6. Lee, Y., Y. S. Lee, S. Y. Cho, and H. J. Kwon. 2015. Perspective of Peptide Vaccine Composed of Epitope Peptide, CpG-DNA, and Liposome Complex Without Carriers. *Advances in protein chemistry and structural biology* 99: 75-97.
7. Skwarczynski, M., and I. Toth. 2014. Recent advances in peptide-based subunit nanovaccines. *Nanomedicine* 9: 2657-2669.
8. Zeng, W., S. Gauci, S. Ghosh, J. Walker, and D. C. Jackson. 2005. Characterisation of the antibody response to a totally synthetic immunocontraceptive peptide vaccine based on LHRH. *Vaccine* 23: 4427-4435.
9. Kashi, V. P., R. A. Jacob, R. A. Shamanna, M. Menon, A. Balasiddaiah, R. K. Varghese, M. Bachu, and U. Ranga. 2014. The grafting of universal T-helper epitopes enhances immunogenicity of HIV-1 Tat concurrently improving its safety profile. *PloS one* 9: e114155.
10. Dyall, R., W. B. Bowne, L. W. Weber, J. LeMaoult, P. Szabo, Y. Moroi, G. Piskun, J. J. Lewis, A. N. Houghton, and J. Nikolic-Zugic. 1998. Heteroclitic immunization induces tumor immunity. *J Exp Med* 188: 1553-1561.
11. Yxfeldt, G., G. Froman, P. A. Mardh, and M. E. Ward. 1994. Reactivity of antibodies to heteroclitic peptides based on the *Chlamydia trachomatis* major outer-membrane protein. *Microbiology* 140 (Pt 4): 815-821.
12. Good, M. F., M. Pandey, M. R. Batzloff, and G. J. Tyrrell. 2015. Strategic development of the conserved region of the M protein and other candidates as vaccines to prevent infection with group A streptococci. *Expert review of vaccines* 14: 1459-1470.
13. Brandt, E. R., W. A. Hayman, B. Currie, S. Pruksakorn, and M. F. Good. 1997. Human antibodies to the conserved region of the M protein: opsonization of heterologous strains of group A streptococci. *Vaccine* 15: 1805-1812.
14. Pandey, M., V. Ozberk, A. Calcutt, E. Langshaw, J. Powell, T. Rivera-Hernandez, M. F. Ho, Z. Philips, M. R. Batzloff, and M. F. Good. 2016. Streptococcal Immunity Is Constrained by Lack of Immunological Memory following a Single Episode of Pyoderma. *PLoS pathogens* 12: e1006122.
15. Batzloff, M. R., A. Fane, D. Gorton, M. Pandey, T. Rivera-Hernandez, A. Calcutt, G. Yeung, J. Hartas, L. Johnson, C. M. Rush, J. McCarthy, N. Ketheesan, and M. F. Good. 2016. Preclinical immunogenicity and safety of a Group A streptococcal M protein-based vaccine candidate. *Human vaccines & immunotherapeutics* 12: 3089-3096.

16. Batzloff, M. R., W. A. Hayman, M. R. Davies, M. Zeng, S. Pruksakorn, E. R. Brandt, and M. F. Good. 2003. Protection against group A *streptococcus* by immunization with J8-diphtheria toxoid: contribution of J8- and diphtheria toxoid-specific antibodies to protection. *J Infect Dis* 187: 1598-1608.
17. Brandt, E. R., K. S. Sriprakash, R. I. Hobb, W. A. Hayman, W. Zeng, M. R. Batzloff, D. C. Jackson, and M. F. Good. 2000. New multi-determinant strategy for a group A streptococcal vaccine designed for the Australian Aboriginal population. *Nat Med* 6: 455-459.
18. Dileepan, T., J. L. Linehan, J. J. Moon, M. Pepper, M. K. Jenkins, and P. P. Cleary. 2011. Robust antigen specific th17 T cell response to group A *Streptococcus* is dependent on IL-6 and intranasal route of infection. *PLoS pathogens* 7: e1002252.
19. Pandey, M., E. Langshaw, J. Hartas, A. Lam, M. R. Batzloff, and M. F. Good. 2015. A synthetic M protein peptide synergizes with a CXC chemokine protease to induce vaccine-mediated protection against virulent streptococcal pyoderma and bacteremia. *J Immunol* 194: 5915-5925.
20. Shen, Y., J. Maupetit, P. Derreumaux, and P. Tuffery. 2014. Improved PEP-FOLD Approach for Peptide and Miniprotein Structure Prediction. *J Chem Theory Comput* 10: 4745-4758.
21. Abraham, M. J. 2015. GROMACS: High performance molecular simulations through multi-level parallelism from laptops to supercomputers. *SoftwareX* 1-2: 19-25.
22. Maier, J. A., C. Martinez, K. Kasavajhala, L. Wickstrom, K. E. Hauser, and C. Simmerling. 2015. ff14SB: Improving the Accuracy of Protein Side Chain and Backbone Parameters from ff99SB. *J Chem Theory Comput* 11: 3696-3713.
23. Jorgensen, W. L., Chandrasekhar, J., Madura, J. D., Impey, R. W. & Klein, M. L. 1983. Comparison of simple potential functions for simulating liquid water. *J. Chem. Phys.* 79: 926-935.
24. Páll, S. H., B. 2013. A flexible algorithm for calculating pair interactions on SIMD architectures. *Comput. Phys. Commun.* 184: 2641-2650.
25. Darden, T., York, D. & Pedersen, L. 1993. Particle mesh Ewald: An N·log(N) method for Ewald sums in large systems. *J. Chem. Phys.* 98: 10089-10092.
26. Essmann, U. e. a. 1995. A smooth particle mesh Ewald method. *J. Chem. Phys.* 103: 8577-8593
27. Bussi, G., Donadio, D. & Parrinello, M. 2007. Canonical sampling through velocity rescaling. *J. Chem. Phys.* 126: 014101
28. Berendsen, H. J. C., Postma, J. P. M., Gunsteren, W. F. van, DiNola, A. & Haak, J. R. 1984. Molecular dynamics with coupling to an external bath. *J. Chem. Phys.* 81: 3684-3690
29. Hess, B. 2008. P-LINCS: A Parallel Linear Constraint Solver for Molecular Simulation. *J Chem Theory Comput* 4: 116-122.
30. Lupas, A., M. Van Dyke, and J. Stock. 1991. Predicting coiled coils from protein sequences. *Science* 252: 1162-1164.

TABLE 1 p145 and the minimal epitope

| Peptide | Sequence | Peptide length |
|---|---|---|
| p145 | LRRDLDASREAKKQVEKALE (SEQ ID NO: 3) | 20 amino acids |
| Minimal epitope* | SREAKKQVEKAL (SEQ ID NO: 4) | 12 amino acids |

*A 12-mer minimal B-cell epitope from within p145 (31).

TABLE 2

The L2* library with the sequence of individual peptides

| | | |
|---|---|---|
| p145 | LRRDLDA SREAKKQVEKAL E | (SEQ ID NO: 3) |
| p*1. | LRRDLDA ENEAKKQVEKAL E | (SEQ ID NO: 5) |
| p*2. | LRRDLDA EDEAKKQVEKAL E | (SEQ ID NO: 6) |
| p*3. | LRRDLDA EREAKNQVEKAL E | (SEQ ID NO: 7) |
| p*4. | LRRDLDA EREAKKQVERAL E | (SEQ ID NO: 8) |
| p*5. | LRRDLDA EREAKKQVEMAL E | (SEQ ID NO: 9) |
| p*6. | LRRDLDA VNEAKKQVEKAL E | (SEQ ID NO: 10) |
| p*7. | LRRDLDA VDEAKKQVEKAL E | (SEQ ID NO: 11) |
| p*8. | LRRDLDA VREAKNQVEKAL E | (SEQ ID NO: 12) |
| p*9. | LRRDLDA VREAKKQVERAL E | (SEQ ID NO: 13) |
| p*10. | LRRDLDA VREAKKQVEMAL E | (SEQ ID NO: 14) |
| p*11. | LRRDLDA SNEAKNQVEKAL E | (SEQ ID NO: 15) |
| p*12. | LRRDLDA SNEAKKQVERAL E | (SEQ ID NO: 16) |
| p*13. | LRRDLDA SNEAKKQVEMAL E | (SEQ ID NO: 17) |
| p*14. | LRRDLDA SDEAKNQVEKAL E | (SEQ ID NO: 18) |
| p*15. | LRRDLDA SDEAKKQVERAL E | (SEQ ID NO: 19) |
| p*16. | LRRDLDA SDEAKKQVEMAL E | (SEQ ID NO: 20) |
| p*17. | LRRDLDA SREAKNQVERAL E | (SEQ ID NO: 1) |
| p*18. | LRRDLDA SREAKNQVEMAL E | (SEQ ID NO: 21) |

*Each peptide in L2 library was designed with two amino acid alterations. The amino acids substituted in the original p145 sequence are underlined.

TABLE 3

The L1* peptide library including 86 variants of p145

| P145. | Biotin-SGSGLRRDLDASREAKKQVEKAL E | (SEQ ID NO: 113) |
|---|---|---|
| 1. | Biotin-SGSGLRRDLDA LREAKKQVEKAL E | (SEQ ID NO: 25) |
| 2. | Biotin-SGSGLRRDLDA AREAKKQVEKAL E | (SEQ ID NO: 26) |
| 3. | Biotin-SGSGLRRDLDA YREAKKQVEKAL E | (SEQ ID NO: 27) |

TABLE 3-continued

The L1* peptide library including 86 variants of p145

| | | |
|---|---|---|
| 4. | Biotin-SGSGLRRDLDA MREAKKQVEKAL E | (SEQ ID NO: 28) |
| 5. | Biotin-SGSGLRRDLDA EREAKKQVEKAL E | (SEQ ID NO: 29) |
| 6. | Biotin-SGSGLRRDLDA VREAKKQVEKAL E | (SEQ ID NO: 30) |
| 7. | Biotin-SGSGLRRDLDA IREAKKQVEKAL E | (SEQ ID NO: 31) |
| 8. | Biotin-SGSGLRRDLDA SEEAKKQVEKAL E | (SEQ ID NO: 32) |
| 9. | Biotin-SGSGLRRDLDA SQEAKKQVEKAL E | (SEQ ID NO: 33) |
| 10. | Biotin-SGSGLRRDLDA SKEAKKQVEKAL E | (SEQ ID NO: 34) |
| 11. | Biotin-SGSGLRRDLDA SNEAKKQVEKAL E | (SEQ ID NO: 35) |
| 12. | Biotin-SGSGLRRDLDA STEAKKQVEKAL E | (SEQ ID NO: 36) |
| 13. | Biotin-SGSGLRRDLDA SDEAKKQVEKAL E | (SEQ ID NO: 37) |
| 14. | Biotin-SGSGLRRDLDA SRNAKKQVEKAL E | (SEQ ID NO: 38) |
| 15. | Biotin-SGSGLRRDLDA SRKAKKQVEKAL E | (SEQ ID NO: 39) |
| 16. | Biotin-SGSGLRRDLDA SRRAKKQVEKAL E | (SEQ ID NO: 40) |
| 17. | Biotin-SGSGLRRDLDA SRDAKKQVEKAL E | (SEQ ID NO: 41) |
| 18. | Biotin-SGSGLRRDLDA SRQAKKQVEKAL E | (SEQ ID NO: 42) |
| 19. | Biotin-SGSGLRRDLDA SRAAKKQVEKAL E | (SEQ ID NO: 43) |
| 20. | Biotin-SGSGLRRDLDA SRSAKKQVEKAL E | (SEQ ID NO: 44) |
| 21. | Biotin-SGSGLRRDLDA SRTAKKQVEKAL E | (SEQ ID NO: 45) |
| 22. | Biotin-SGSGLRRDLDA SREEKKQVEKAL E | (SEQ ID NO: 46) |
| 23. | Biotin-SGSGLRRDLDA SREKKKQVEKAL E | (SEQ ID NO: 47) |
| 24. | Biotin-SGSGLRRDLDA SREQKKQVEKAL E | (SEQ ID NO: 48) |
| 25. | Biotin-SGSGLRRDLDA SRENKKQVEKAL E | (SEQ ID NO: 49) |
| 26. | Biotin-SGSGLRRDLDA SRERKKQVEKAL E | (SEQ ID NO: 50) |
| 27. | Biotin-SGSGLRRDLDA SREDKKQVEKAL E | (SEQ ID NO: 51) |
| 28. | Biotin-SGSGLRRDLDA SREALKQVEKAL E | (SEQ ID NO: 52) |
| 29. | Biotin-SGSGLRRDLDA SREAIKQVEKAL E | (SEQ ID NO: 53) |
| 30. | Biotin-SGSGLRRDLDA SREAMKQVEKAL E | (SEQ ID NO: 54) |
| 31. | Biotin-SGSGLRRDLDA SREAVKQVEKAL E | (SEQ ID NO: 55) |
| 32. | Biotin-SGSGLRRDLDA SREAYKQVEKAL E | (SEQ ID NO: 56) |
| 33. | Biotin-SGSGLRRDLDA SREAAKQVEKAL E | (SEQ ID NO: 57) |
| 34. | Biotin-SGSGLRRDLDA SREANKQVEKAL E | (SEQ ID NO: 58) |
| 35. | Biotin-SGSGLRRDLDA SREARKQVEKAL E | (SEQ ID NO: 59) |
| 36. | Biotin-SGSGLRRDLDA SREAKEQVEKAL E | (SEQ ID NO: 60) |
| 37. | Biotin-SGSGLRRDLDA SREAKDQVEKAL E | (SEQ ID NO: 61) |
| 38. | Biotin-SGSGLRRDLDA SREAKQQVEKAL E | (SEQ ID NO: 62) |
| 39. | Biotin-SGSGLRRDLDA SREAKAQVEKAL E | (SEQ ID NO: 63) |
| 40. | Biotin-SGSGLRRDLDA SREAKNQVEKAL E | (SEQ ID NO: 64) |
| 41. | Biotin-SGSGLRRDLDA SREAKRQVEKAL E | (SEQ ID NO: 65) |
| 42. | Biotin-SGSGLRRDLDA SREAKTQVEKAL E | (SEQ ID NO: 66) |

TABLE 3-continued

The L1* peptide library including 86 variants of p145

43. Biotin-SGSGLRRDLDA SREAKKEVEKAL E (SEQ ID NO: 67)
44. Biotin-SGSGLRRDLDA SREAKKDVEKAL E (SEQ ID NO: 68)
45. Biotin-SGSGLRRDLDA SREAKKKVEKAL E (SEQ ID NO: 69)
46. Biotin-SGSGLRRDLDA SREAKKNVEKAL E (SEQ ID NO: 70)
47. Biotin-SGSGLRRDLDA SREAKKRVEKAL E (SEQ ID NO: 71)
48. Biotin-SGSGLRRDLDA SREAKKAVEKAL E (SEQ ID NO: 72)
49. Biotin-SGSGLRRDLDA SREAKKSVEKAL E (SEQ ID NO: 73)
50. Biotin-SGSGLRRDLDA SREAKKTVEKAL E (SEQ ID NO: 74)
51. Biotin-SGSGLRRDLDA SREAKKHVEKAL E (SEQ ID NO: 75)
52. Biotin-SGSGLRRDLDA SREAKKQLEKAL E (SEQ ID NO: 76)
53. Biotin-SGSGLRRDLDA SREAKKQAEKAL E (SEQ ID NO: 77)
54. Biotin-SGSGLRRDLDA SREAKKQYEKAL E (SEQ ID NO: 78)
55. Biotin-SGSGLRRDLDA SREAKKQMEKAL E (SEQ ID NO: 79)
56. Biotin-SGSGLRRDLDA SREAKKQEEKAL E (SEQ ID NO: 80)
57. Biotin-SGSGLRRDLDA SREAKKQIEKAL E (SEQ ID NO: 81)
58. Biotin-SGSGLRRDLDA SREAKKQVQKAL E (SEQ ID NO: 82)
59. Biotin-SGSGLRRDLDA SREAKKQVKKAL E (SEQ ID NO: 83)
60. Biotin-SGSGLRRDLDA SREAKKQVNKAL E (SEQ ID NO: 84)
61. Biotin-SGSGLRRDLDA SREAKKQVRKAL E (SEQ ID NO: 85)
62. Biotin-SGSGLRRDLDA SREAKKQVTKAL E (SEQ ID NO: 86)
63. Biotin-SGSGLRRDLDA SREAKKQVDKAL E (SEQ ID NO: 87)
64. Biotin-SGSGLRRDLDA SREAKKQVEEAL E (SEQ ID NO: 88)
65. Biotin-SGSGLRRDLDA SREAKKQVENAL E (SEQ ID NO: 89)
66. Biotin-SGSGLRRDLDA SREAKKQVERAL E (SEQ ID NO: 90)
67. Biotin-SGSGLRRDLDA SREAKKQVEDAL E (SEQ ID NO: 91)
68. Biotin-SGSGLRRDLDA SREAKKQVEQAL E (SEQ ID NO: 92)
69. Biotin-SGSGLRRDLDA SREAKKQVEAAL E (SEQ ID NO: 93)
70. Biotin-SGSGLRRDLDA SREAKKQVESAL E (SEQ ID NO: 94)
71. Biotin-SGSGLRRDLDA SREAKKQVETAL E (SEQ ID NO: 95)
72. Biotin-SGSGLRRDLDA SREAKKQVEMAL E (SEQ ID NO: 96)
73. Biotin-SGSGLRRDLDA SREAKKQVEKEL E (SEQ ID NO: 97)
74. Biotin-SGSGLRRDLDA SREAKKQVEKKL E (SEQ ID NO: 98)
75. Biotin-SGSGLRRDLDA SREAKKQVEKQL E (SEQ ID NO: 99)
76. Biotin-SGSGLRRDLDA SREAKKQVEKNL E (SEQ ID NO: 100)
77. Biotin-SGSGLRRDLDA SREAKKQVEKRL E (SEQ ID NO: 101)
78. Biotin-SGSGLRRDLDA SREAKKQVEKDL E (SEQ ID NO: 102)
79. Biotin-SGSGLRRDLDA SREAKKQVEKAI E (SEQ ID NO: 103)
80. Biotin-SGSGLRRDLDA SREAKKQVEKAM E (SEQ ID NO: 104)
81. Biotin-SGSGLRRDLDA SREAKKQVEKAV E (SEQ ID NO: 105)

TABLE 3-continued

The L1* peptide library including 86 variants of p145

82. Biotin-SGSGLRRDLDA SREAKKQVEKAY E (SEQ ID NO: 106)

83. Biotin-SGSGLRRDLDA SREAKKQVEKAK E (SEQ ID NO: 107)

84. Biotin-SGSGLRRDLDA SREAKKQVEKAA E (SEQ ID NO: 108)

85. Biotin-SGSGLRRDLDA SREAKKQVEKAN E (SEQ ID NO: 109)

86. Biotin-SGSGLRRDLDA SREAKKQVEKAR E (SEQ ID NO: 110)

87. Biotin-SGSGEGKVSTLPLDIQIIAATMSK (SEQ ID NO: 111)

*The L1 library was designed with one amino acid substitution in each of the 86 variants of p145. The substituted amino acid is underlined. Biotin and the extra amino acids SGSG were included at the N-terminal end. Peptide 87 is a non-specific peptide (pNS) from *Schistosoma*.

---

The invention claimed is:

1. A method of eliciting a mucosal immune response to group A streptococcal bacteria in a mammal, said method including the step of intramuscularly administering to the mammal an isolated protein comprising:
   (a) the amino acid sequence of SEQ ID NO: 1;
   (b) the amino acid sequence of SEQ ID NO: 21;
   (c) the amino acid sequence of SEQ ID NO: 1 conjugated to a carrier protein; or
   (d) the amino acid sequence of SEQ ID NO: 21 conjugated to a carrier protein.

2. A method of inducing mucosal immunity against a group A streptococcal bacterial infection in a mammal, said method including the step of intramuscularly administering to the mammal an isolated protein comprising:
   (a) the amino acid sequence of SEQ ID NO: 1;
   (b) the amino acid sequence of SEQ ID NO: 21;
   (c) the amino acid sequence of SEQ ID NO: 1 conjugated to a carrier protein; or
   (d) the amino acid sequence of SEQ ID NO: 21 conjugated to a carrier protein.

3. A method of treating a group A streptococcal bacterial infection in a mammal by eliciting a mucosal immune response or inducing mucosal immunity against the group A streptococcal bacterial infection in the mammal, said method including the step of intramuscularly administering to the mammal an isolated protein comprising:
   (a) the amino acid sequence of SEQ ID NO: 1;
   (b) the amino acid sequence of SEQ ID NO: 21;
   (c) the amino acid sequence of SEQ ID NO: 1 conjugated to a carrier protein; or
   (d) the amino acid sequence of SEQ ID NO: 21 conjugated to a carrier protein.

4. The method of claim 1, which further includes administering to the mammal an isolated immunogenic fragment comprising an amino acid sequence selected from the group consisting of:
   (i) SEQ ID NO: 23;
   (ii) an amino acid sequence at least 90% identical to SEQ ID NO: 23;
   (iii) the SEQ ID NO: 23 or the amino acid sequence at least 90% identical to SEQ ID NO: 23 further consisting one or a plurality of lysine residues at its N-terminus and/or C-terminus;
   (iv) SEQ ID NO: 24; and
   (v) any one of (i) to (iv) conjugated to a carrier protein.

5. The method of claim 2, which further includes administering an isolated immunogenic fragment comprising an amino acid sequence selected from the group consisting of:
   (i) SEQ ID NO: 23;
   (ii) an amino acid sequence at least 90% identical to SEQ ID NO: 23;
   (iii) the SEQ ID NO: 23 or the amino acid sequence at least 90% identical to SEQ ID NO: 23 further consisting one or a plurality of lysine residues at an N-terminus and/or C-terminus thereof;
   (iv) SEQ ID NO: 24; and
   (v) any one of (i) to (iv) conjugated to a carrier protein.

6. The method of claim 3, which further includes administering an isolated immunogenic fragment comprising an amino acid sequence selected from the group consisting of:
   (i) SEQ ID NO: 23;
   (ii) an amino acid sequence at least 90% identical to SEQ ID NO: 23;
   (iii) the SEQ ID NO: 23 or the amino acid sequence at least 90% identical to SEQ ID NO: 23 further consisting one or a plurality of lysine residues at an N-terminus and/or C-terminus thereof;
   (iv) SEQ ID NO: 24; and
   (v) any one of (i) to (iv) conjugated to a carrier protein.

7. The method of claim 3, wherein a single immunization of the mammal with said isolated protein protects the mammal against group A streptococcal skin disease.

8. The method of claim 1, wherein the carrier protein is thyroglobulin, albumin, a toxin, or a toxoid.

9. The method of claim 2, wherein the carrier protein is thyroglobulin, albumin, a toxin, or a toxoid.

10. The method of claim 3, wherein the carrier protein is thyroglobulin, albumin, a toxin, or a toxoid.

11. The method of claim 1, wherein the carrier protein is diphtheria toxoid.

12. The method of claim 2, wherein the carrier protein is diphtheria toxoid.

13. The method of claim 3, wherein the carrier protein is diphtheria toxoid.

14. The method of claim 8, wherein the toxin is a diphtheria toxin, a tetanus toxin, a pertussis toxin, a *Pseudomonas* toxin, an *E. coli* toxin, a *Staphylococcus* toxin, or a *Streptococcus* toxin.

15. The method of claim 9, wherein the toxin is a diphtheria toxin, a tetanus toxin, a pertussis toxin, a *Pseudomonas* toxin, an *E. coli* toxin, a *Staphylococcus* toxin, or a *Streptococcus* toxin.

16. The method of claim 10, wherein the toxin is a diphtheria toxin, a tetanus toxin, a pertussis toxin, a *Pseudomonas* toxin, an *E. coli* toxin, a *Staphylococcus* toxin, or a *Streptococcus* toxin.

17. A method of ameliorating group A streptococcal skin infection, group A streptococcal intranasal infection, or invasive group A streptococcal infection in a mammal, said method including the step of parenterally administering to the mammal an isolated protein comprising:
 (a) the amino acid sequence of SEQ ID NO: 1;
 (b) the amino acid sequence of SEQ ID NO: 21;
 (c) the amino acid sequence of SEQ ID NO: 1 conjugated to a carrier protein; or
 (d) the amino acid sequence of SEQ ID NO: 21 conjugated to a carrier protein.

\* \* \* \* \*